US009958457B2

(12) United States Patent
Amir et al.

(10) Patent No.: US 9,958,457 B2
(45) Date of Patent: May 1, 2018

(54) DEVICE AND METHOD FOR DETECTION OF ANALYTES

(71) Applicant: Xcellcure, LLC, St. Louis, MO (US)

(72) Inventors: Leah Amir, St. Louis, MO (US); Gary Anderson, St. Louis, MO (US)

(73) Assignee: XCELLCURE, LLC, St. Louis, MO (US)

( * ) Notice: Subject to any disclaimer, the term of this patent is extended or adjusted under 35 U.S.C. 154(b) by 442 days.

(21) Appl. No.: 14/388,164

(22) PCT Filed: Mar. 26, 2013

(86) PCT No.: PCT/US2013/033916
§ 371 (c)(1),
(2) Date: Sep. 25, 2014

(87) PCT Pub. No.: WO2013/148708
PCT Pub. Date: Oct. 3, 2013

(65) Prior Publication Data
US 2015/0065372 A1 Mar. 5, 2015

Related U.S. Application Data

(60) Provisional application No. 61/790,686, filed on Mar. 15, 2013, provisional application No. 61/615,599, filed on Mar. 26, 2012.

(51) Int. Cl.
G01N 33/68 (2006.01)
C12Q 1/68 (2018.01)
G01N 33/543 (2006.01)

(52) U.S. Cl.
CPC ....... *G01N 33/6863* (2013.01); *C12Q 1/6883* (2013.01); *G01N 33/543* (2013.01); *G01N 33/6893* (2013.01); *G01N 2800/324* (2013.01); *G01N 2800/325* (2013.01); *G01N 2800/50* (2013.01)

(58) Field of Classification Search
None
See application file for complete search history.

(56) References Cited

U.S. PATENT DOCUMENTS

| 4,861,727 | A | 8/1989 | Hauenstein et al. |
| 2001/0004526 | A1 | 6/2001 | Everhart et al. |
| 2009/0197344 | A1 | 8/2009 | Villard-Saussine et al. |
| 2010/0240149 | A1 | 9/2010 | Nazareth et al. |
| 2011/0045514 | A1 | 2/2011 | Muntendam et al. |

FOREIGN PATENT DOCUMENTS

| CN | 1350641 A | 6/2000 |
| CN | 104755930 A | 7/2015 |
| EP | 0391359 A2 | 10/1990 |
| EP | 2201384 A2 | 6/2010 |
| EP | 2831586 A1 | 2/2015 |
| WO | WO 00/34781 A2 * | 11/1999 ............ G01N 33/53 |
| WO | 00/034781 A2 | 6/2000 |
| WO | 01/66124 A | 9/2001 |
| WO | 2008/113361 A1 | 9/2008 |
| WO | 2009/034470 A2 | 3/2009 |
| WO | 2013/148708 A1 | 10/2013 |

OTHER PUBLICATIONS

Blanchard-Dionne et al. (Optics Express, Aug. 1, 2011, vol. 19, No. 16, pp. 1-6).*
Saskia et al. (Journal of Molecular and cellular Cardiology, Vo.45, 2008, pp. 446-452).*
De Jager, S.C., et al. "CCL3 (MIP-1α) levels are elevated during acute coronary syndromes and show strong prognostic power for future ischemic events", Journal of Molecular and Cellular Cardiology, Academic Press, GB, vol. 45, No. 3, Sep. 1, 2008, pp. 446-452.
Supplementary Partial European Search Report from corresponding European Patent Application No. 13769064.0, dated Sep. 10, 2015, pp. 1-5.
De Jager, S.C., et al., "Chemokines CCL3/MIP1α, CCL5/RANTES and CCL18/PARC are independent risk predictors of short-term mortality in patients with acute coronary syndrome," PLoS ONE, vol. 7, No. 9, Sep. 21, 2012, pp. 1-10.
Correia, L.C., et al., "Prognostic value of cytokines and chemokines in addition to the GRACE Score in non-ST-elevation acute coronary syndrome," Clinica Chimica Acta, Elsevier BV, Amsterdam, NL, vol. 411, No. 7-8, Apr. 2, 2010, pp. 540-545.
Supplementary European Search Report and European Search Opinion from corresponding European Patent Application No. 13769064.0, dated Jan. 4, 2016, pp. 1-15.
Office Action dated from U.S. Appl. No. 12/677,437, dated Apr. 25, 2012, pp. 1-8.
Ardigo, D., et al., "Circulating chemokines accurately identify individuals with clinically significant atherosclerotic heart disease," Physiological Genomics, vol. 31, No. 3, pp. 402-409 (2007).
Aukrust, P., et al., "Elevated circulating levels of C—C chemokines in patients with congestive heart failure," Circulation, vol. 97, No. 12, pp. 1136-1143 (1998).
De Jager, S.C., et al., "Plasma chemokine profiling of myocardial infarction patients by a fluorescence microsphere based multiplex assay reveals multiple sensitive chemokine markers," Circulation, vol. 112, No. 17, pp. U161-U162, 78th Annual Scientific Session of the American Heart Association (2005).
Parissis, J., et al., "Plasma profiles of peripheral monocyte-related inflammatory markers in patients with arterial hypertension, correlations with plasma edothelin-1," International Journal of Cardiology, vol. 83, No. 1, pp. 13-21 (2002).
Vandervelde, S., et al., "Stem cell-related cardiac gene expression early after murine myocardial infarction," Cardiovascular Research, vol. 73, No. 4, pp. 783-793 (2007).

(Continued)

*Primary Examiner* — Lisa V Cook
(74) *Attorney, Agent, or Firm* — Polsinelli PC

(57) ABSTRACT

A detection device and associated systems and methods for detecting analytes from a multiplex reaction are described. In particular, a device for conducting at least one detection reaction using a modified ELISA method including a surface with a detection region and a reference region, a detection sensor, and a light source. The detection device may include a complementary metal-oxide-semiconductor (CMOS) image sensor. The device may be used to measure and report discrete quantities or combinations of discrete analytes, providing information to aid in the prognosis and/or diagnosis of altered states of health in vertebrates.

9 Claims, 51 Drawing Sheets

(56) References Cited

OTHER PUBLICATIONS

CN First Office Action dated Nov. 30, 2015 from CN corresponding application No. 201380030197.7, pp. 1-4.
International Search Report and Written Opinion from WO2013/148708 dated Jun. 14, 2013, pp. 1-2.
Parissis, et al., "Serum profiles of C—C chemokines in acute myocardial infarction: Possible implication in postinfarction left ventricular remodeling," Journal of Interferon and Cytokine Research, 2002, vol. 22, pp. 223-229.
De Jager, S.C., 2005, Journal of Immunological Methods, 300: 124-135.
Office Action dated Oct. 29, 2012, from U.S. Appl. No. 12/677,437, pp. 1-9.
Office Action dated Feb. 5, 2015, from U.S. Appl. No. 12/677,437, pp. 1-8.
Office Action dated Apr. 4, 2013, from U.S. Appl. No. 12/677,437, pp. 1-9.
Advisory Action dated Aug. 6, 2013, from U.S. Appl. No. 12/677,437, pp. 1-3.
Notice of Allowance dated May 8, 2015, from U.S. Appl. No. 12/677,437, pp. 1-5.
Office Action from EP Patent Application No. 08830897.8 dated Dec. 17, 2012, pp. 1-5.
Summons to Oral Proceedings for EP Application No. 08830897.8, dated Sep. 18, 2013, pp. 1-3.
China Office Action related to Application No. 201380030197.7, dated Aug. 3, 2016, 3 pages.

* cited by examiner

DEVICE AND METHOD FOR DETECTION OF ANALYTES

INCORPORATION BY REFERENCE

This application claims the benefit of U.S. Provisional Patent Application Ser. No. 61/615,599, filed Mar. 26, 2012 and U.S. Provisional Patent Application Ser. No. 61/790,686, filed Mar. 15, 2013, each of which is hereby incorporated by reference in their entirety.

FIELD OF INVENTION

This invention relates generally to devices, systems, and methods for detecting analytes in a bodily fluid sample.

BACKGROUND

Current systems and devices for determining the concentration of analytes in a sample are either suitable for measuring a single analyte per sample, or use equipment that is not suitable for portable, battery-operated use. In order to most efficiently use the information that can be gleaned from biomarkers, there is a need for a system that is fast, portable, and that is capable of detecting more than one analyte at a time. Such a system may be used in conjunction with different biomarkers to provide information necessary for accurate prognosis and diagnosis.

There is a need, therefore, for a device that is capable of using ambient or low-level light, that is capable of operating by battery or other portable power source, and that is capable of providing information on more than one biomarker from a single biological sample in less than hour.

SUMMARY OF THE INVENTION

In one embodiment, a system for detecting one or more analyses in a sample and diagnosing a condition includes a device, a computing device with one or more processors, a memory, a CRM encoded with an analyte detection application, and a display.

The device includes a surface to conduct at least one detection reaction, with a detection region and a reference region; one or more detection sensors to sense light associated with the detection region; one or more reference sensors to sense light associated with the reference region; and at least one light source to illuminate the detection region and the reference region.

The memory includes a calibration database including one or more calibration sets, each calibration set including a conversion between a combined sensor readout and a concentration of an analyte and a diagnostic database comprising one or more threshold values and one or more diagnostic rules.

The CRM encoded with an analyte detection application includes a plurality of modules executable by the one or more processors. The modules include a control module to control the operation of the device and to coordinate the function of the plurality of modules; a balanced detection module to control the operation of the one or more sensors and/or light sources of the device; an analyte detection module to process combined output signals received from the balanced detection module; a post-processing module to further analyze the analyte concentrations calculated by the analyte detection module; a diagnostic module to compare the entries of the diagnostic array and to determine a condition of a patient according to one or more diagnostic rules defined within the diagnostic database stored in memory; and a GUI module to generate one or more forms to receive input to the system and/or display output from the system.

In another embodiment, a device for the detection of one or more analytes in a sample obtained from a patient includes a surface to conduct at least one detection reaction; one or more detection sensors to sense light associated with the detection region; one or more reference sensors to sense light associated with the reference region; and at least one light source to illuminate the detection region and the reference region.

The surface to conduct at least one detection reaction includes a detection region comprising one or more epitope capture agents, wherein each epitope capture agent is configured to bind exclusively to one of the at least one analytes and a reference region.

The one or more detection sensors and the one or more reference sensors are operated using a balanced sensor method.

Other aspects of the invention are described in detail below.

Analysis of total CCR3 and CCR5 surface expression in all PBMCs also showed a dramatic up-regulation of CCR3 and CCR5 expression, indicating that the increase in CCR3 and CCR5 expression is only partly caused by CD3+ and CD14+ positive cells (G,H,I). *P<0.05, **P<0.01 and #P<0.001.

Figure 5:
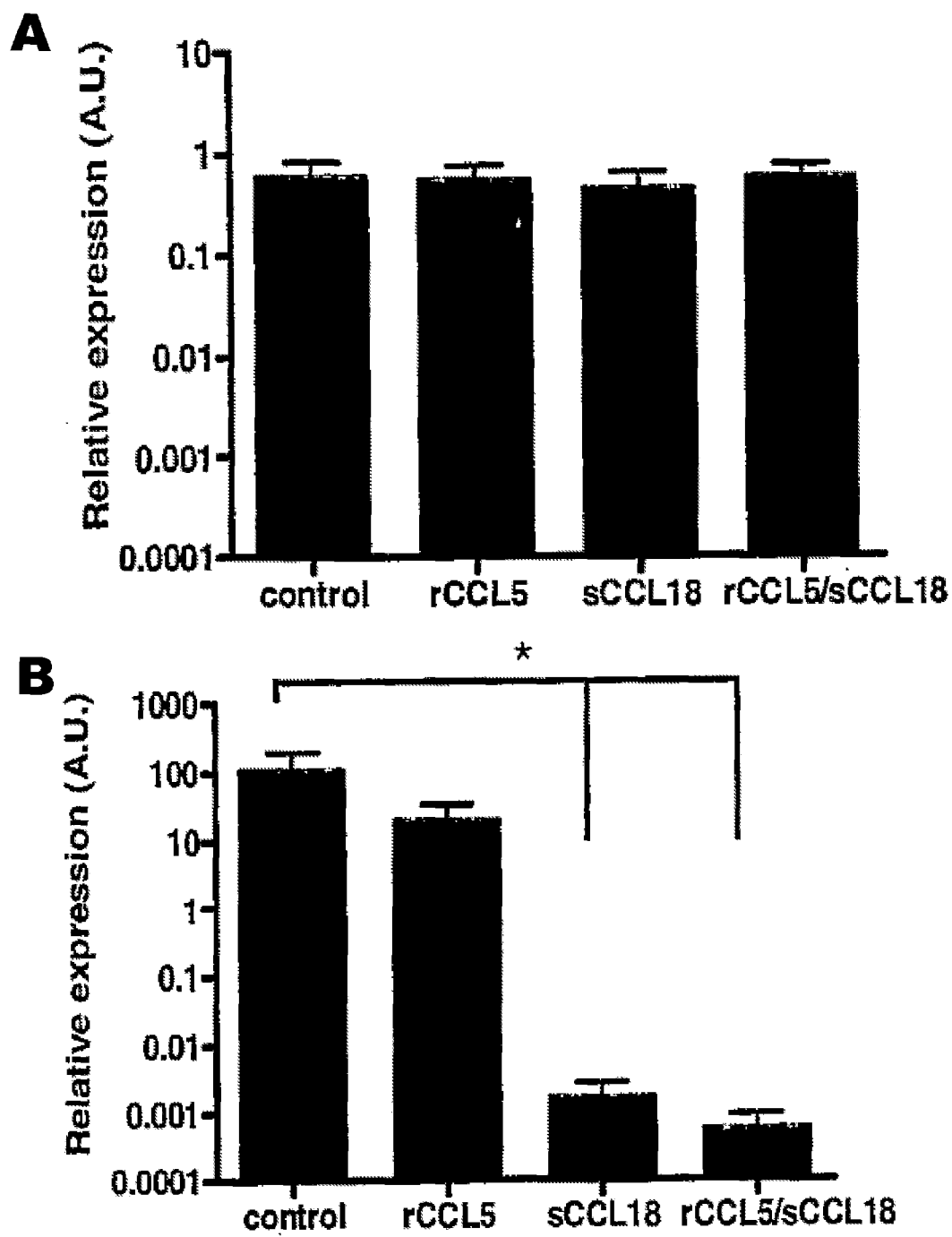
Figure 5:
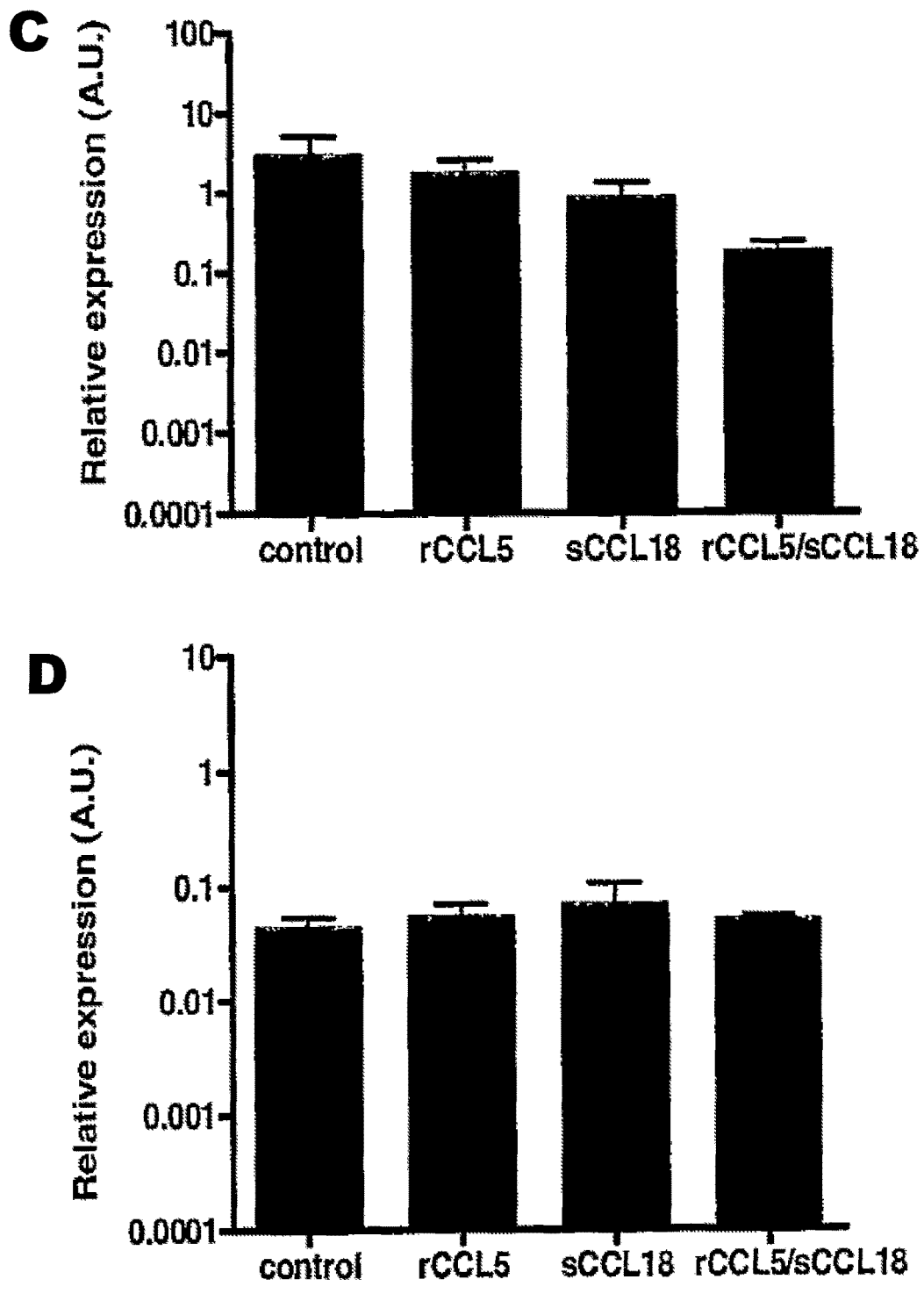

FIG. 5 depicts the effects of stimulating PBMCs with rCCL5 and sCCL18 on CCR1, CCR3, CCR4 and CCR5 expression. Stimulation of PBMCs for 6 hours with rCCL5 and sCCL18 showed no significant differences in CCR1 (A), CCR4 (C) and CCR5 (D) mRNA expression. CCR3 expression was markedly down-regulated after stimulation with sCCL18, but not with rCCL5 (B). Values represent mean±SEM, *P<0.01, N.S.=non-significant, rCCL5=recombinant CCL5, sCCL18=synthetic CCL18.

Figure 6:
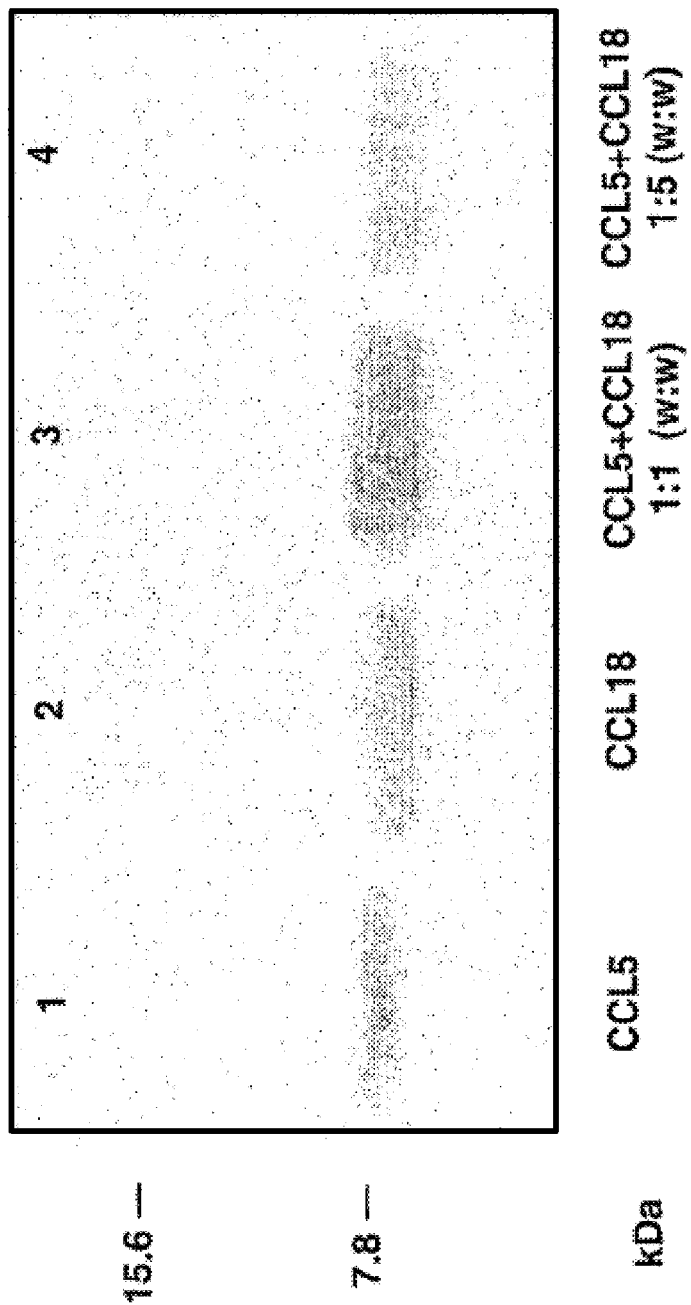

FIG. 6 depicts assessment of heterophilic interaction between CCL5 and CCL18 on PAGE (18%). Lanes 1 and 2 show reference mobility of rCCL5 (7,851 kDa) and sCCL18 (7,855 kDa), both chemokines showed a poor tendency to form 15.6 kDa homodimers. Lanes 3 and 4 were loaded with mixtures of rCCL5 and sCCL18 in a 1:1 and 1:5 ratio (weight:weight), respectively, at which dimers have been crosslinked by incubation for 30 min at RT with 25 mM paraformaldehyde. Note the slightly higher electrophoretic mobility and slightly more yellowish staining of CCL18 monomer and dimer. The extent of dimer formation was not altered after co-incubation and subsequent crosslinking of CCL5 and CCL18, indicating that CCL5 and CCL18 are probably not engaged in any significant heterophilic cross-interaction even at supra-physiological concentrations. The total protein load per lane was constant (2 μg).

Figure 7:
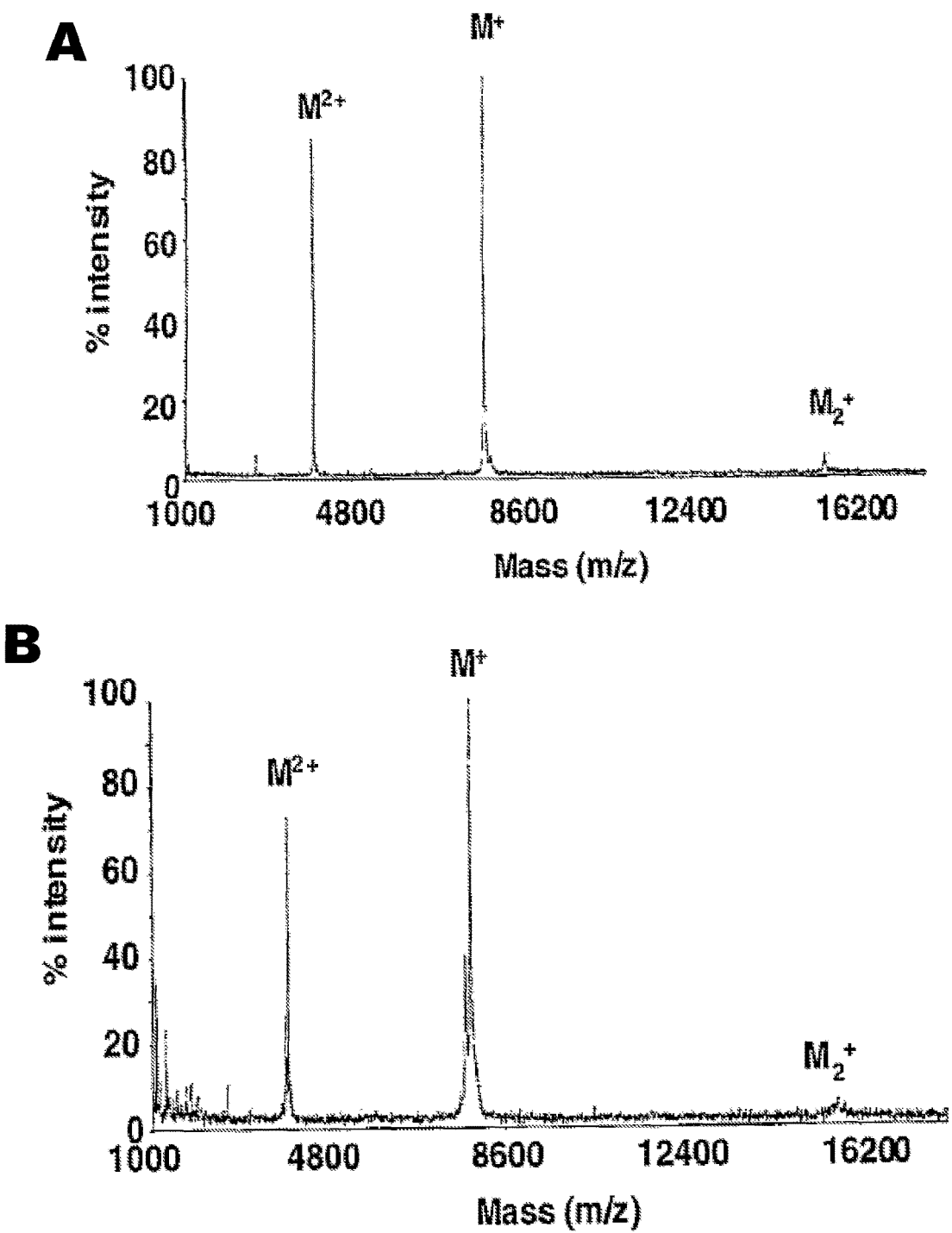
Figure 7:
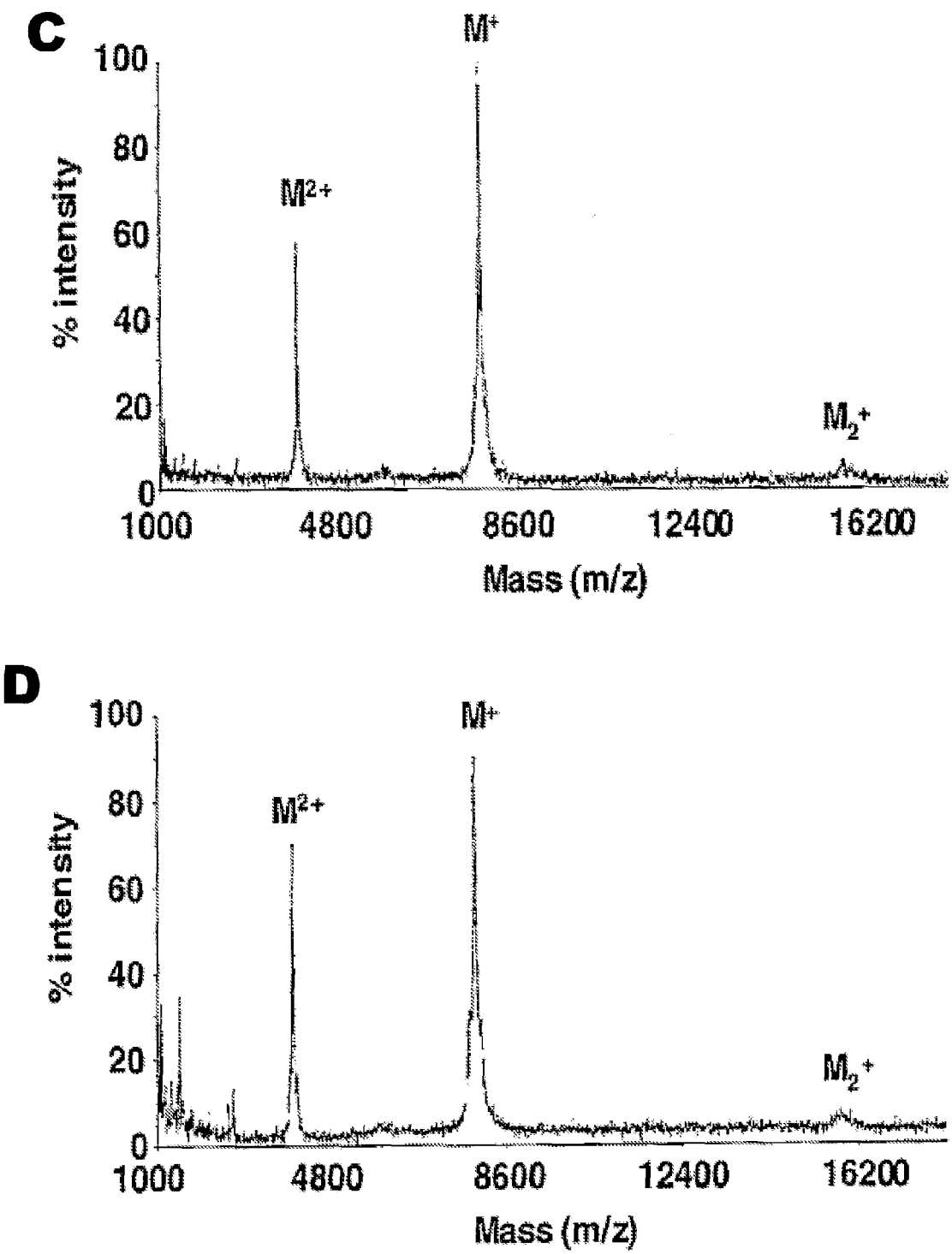

FIG. 7 depicts results of MALDI-TOF MS analysis. The PAGE analysis was corroborated by MALDI-TOF MS analysis: CCL5 and CCL18 (10 pmol/μl) gave mass peaks at approximately 7,860 Da (M+; theoretical mass of CCL5 and CCL18 7,851 and 7,855 Da, respectively), with only minor peaks at approximately 15,730 Da, illustrating the low tendency to form homodimers (M2+) (A,B). MALDI-TOF mass spectrometry of CCL18 that had been pre-incubated with CCL5 at a 1:1 and 1:5 w:w ratio (total concentration 10 pmol/μl) in 50 mM HEPES/0.1 mM EDTA with paraformaldehyde gave an essentially similar pattern and dimer formation was equally marginal at both ratios (C,D).

Figure 8:
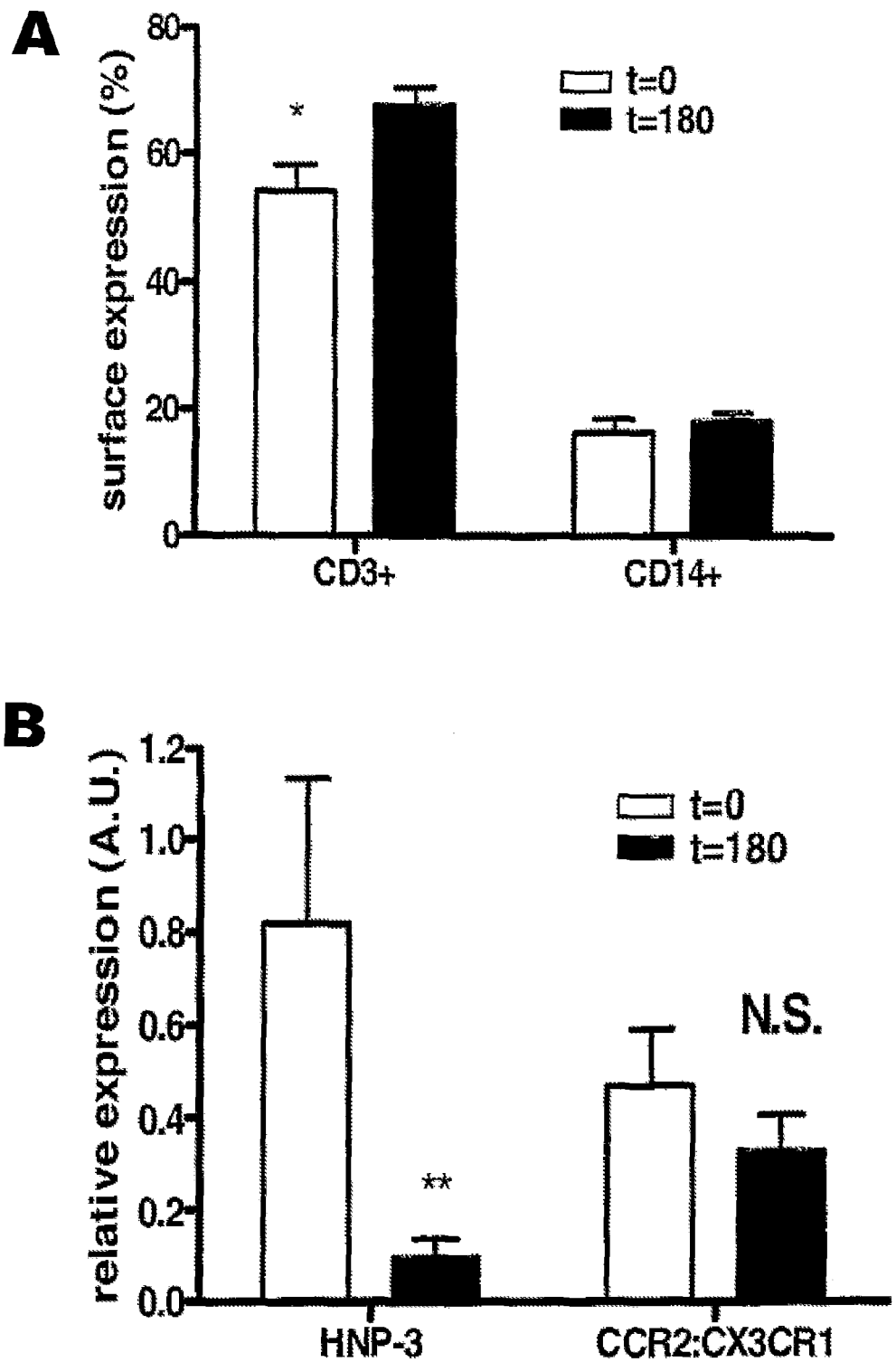

FIG. 8 graphically depicts total levels of CD14+ cells. Total levels of CD 14+ cells (monocytes and neutrophils) did not differ between t=0 and t=180, whereas CD3+ cells showed a small (11.8%), albeit significant decrease at baseline (A). At the mRNA level, an increase of HNP-3+ neutrophils was observed, suggestive of enhanced post-ischemic neutrophil release. However, the CCR2:CX3CR1 expression ratio, a measure of monocyte subset profile, was not differentially regulated (B). Values represent mean±SEM, *P=0.01, **P<0.001 and N.S.=non-significant.

Figure 9:
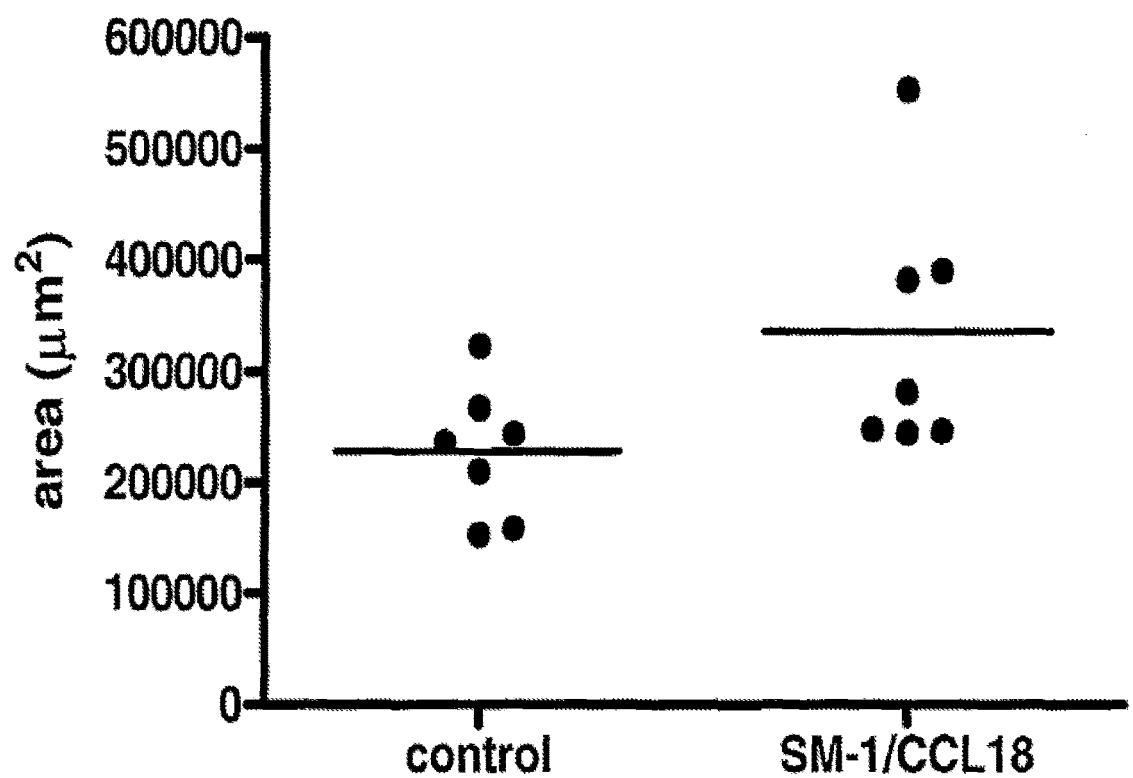
Figure 10:
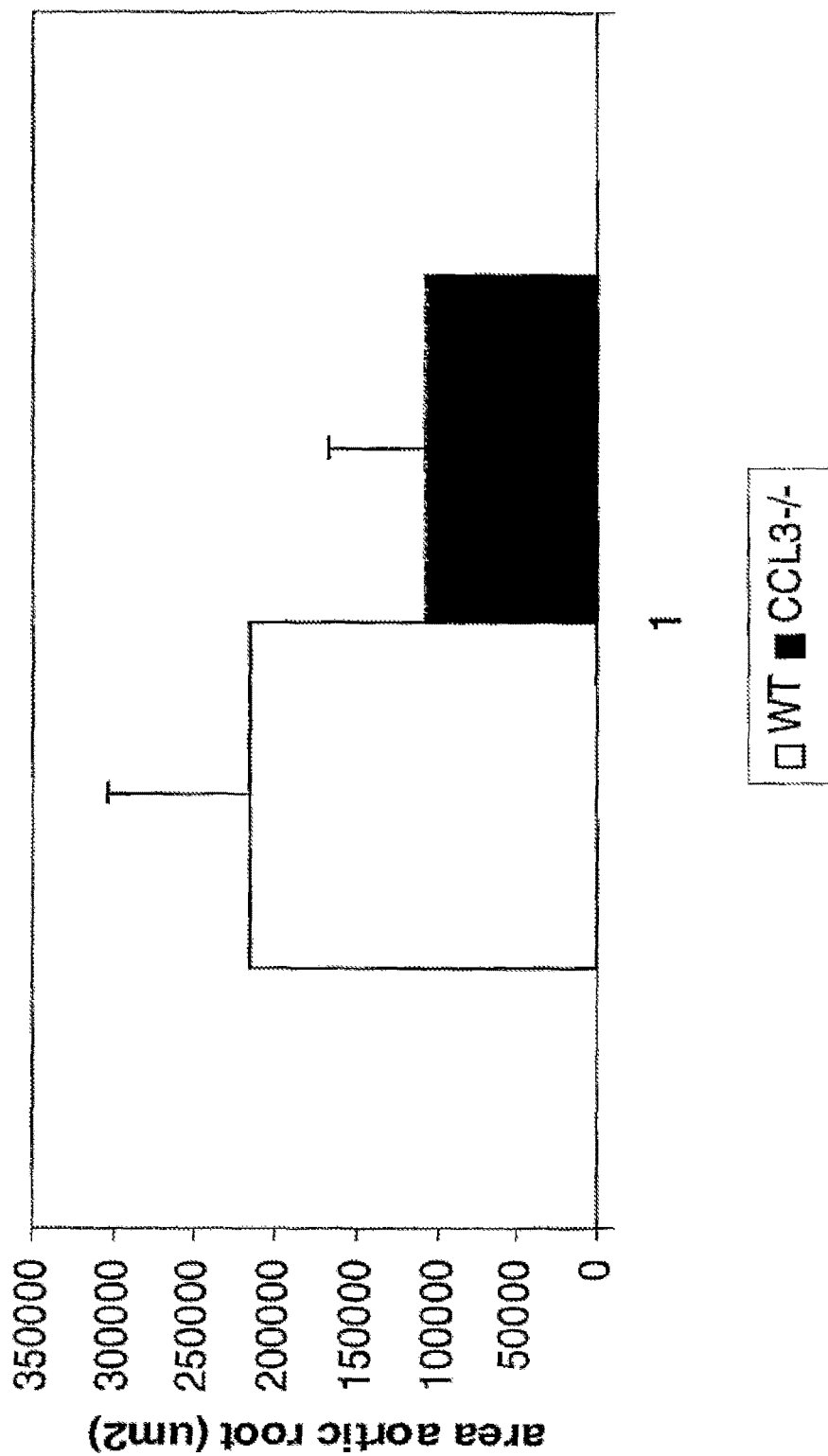

FIG. 9 depicts a graph demonstrating that a transient exposure of mice to elevated levels of CCL18 in the circulation (as effected by repeated administration of recombinant CCL18 protein) will aggravate the development of atherosclerosis and thereby enhance the risk of cardiovascular disease FIG. 10 depicts a graph demonstrating that atherosclerotic plaque development in the aortic sinus of hyperlimidemic (LDLr$^{-/-}$) mice with a deficiency of CCL3 is sharply reduced. WT=wildtype; CCL3$^{-/-}$=hyperlimidemic mice. Y-axis=atherosclerotic plaque development, reported as area aortic root (μm$^2$).

Figure 11:
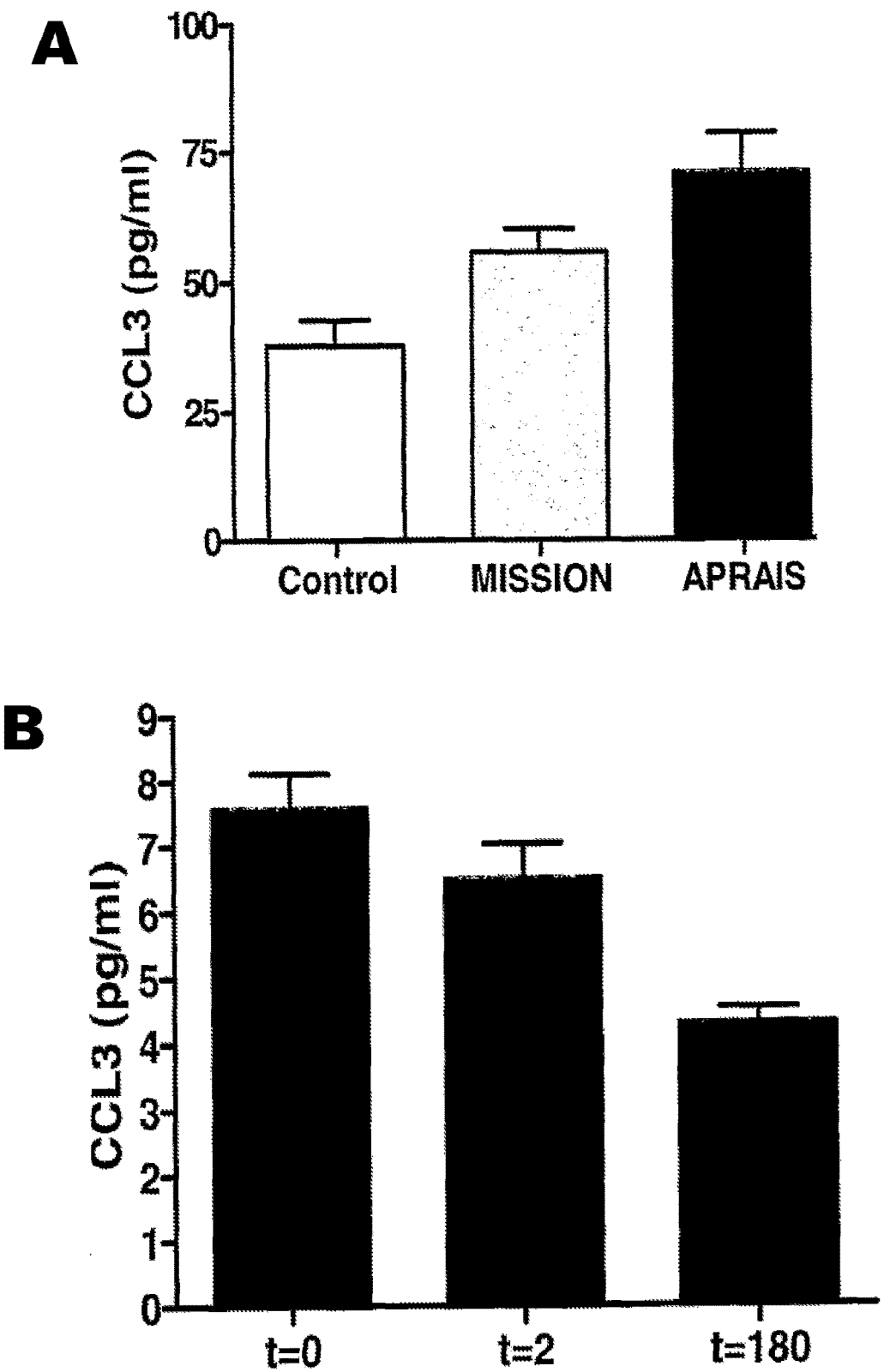

FIG. 11 graphically depicts levels of circulating CCL3 levels (y-axis). Circulating CCL3 levels in APRAIS were comparable with those seen in patients from the MISSION! cohort (A). Temporal CCL3 monitoring performed in the APRAIS cohort of patients with unstable angina pectoris clearly shows the transient increase of CCL3 during ischemia, since levels were significantly lowered at t=180 compared to t=0 (B). *P=0.03 and **P<0.001.

Figure 12:
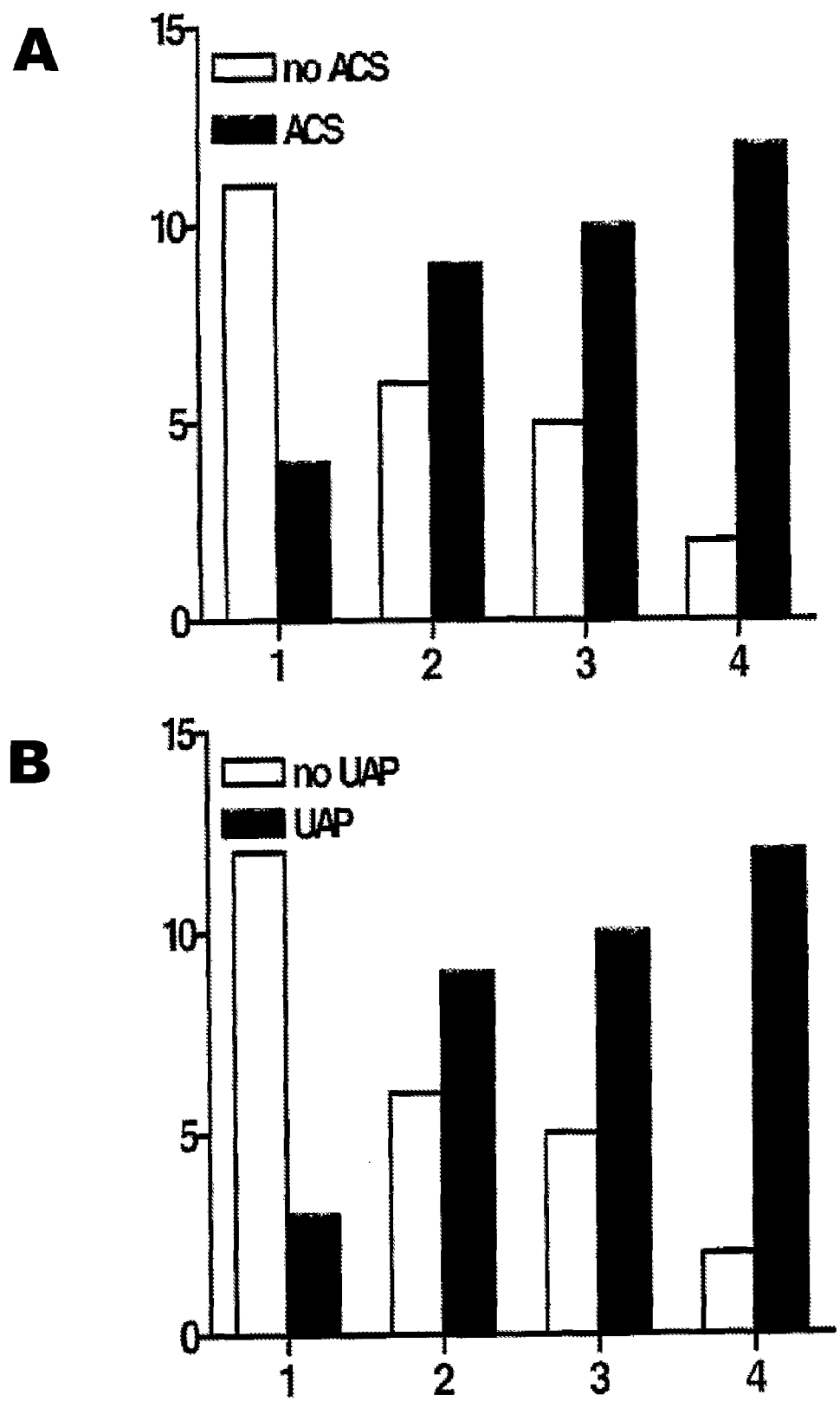

FIG. 12 graphically depicts upper quartile levels of CCL3. Upper quartile levels of CCL3 at baseline are predictive for the occurrence of acute coronary syndromes during follow-up (A). Furthermore, upper quartile levels were also indicative of recurrent ischemic symptoms during or directly after hospitalisation (B). *P=0.01 and **P<0.01.

Figure 13:
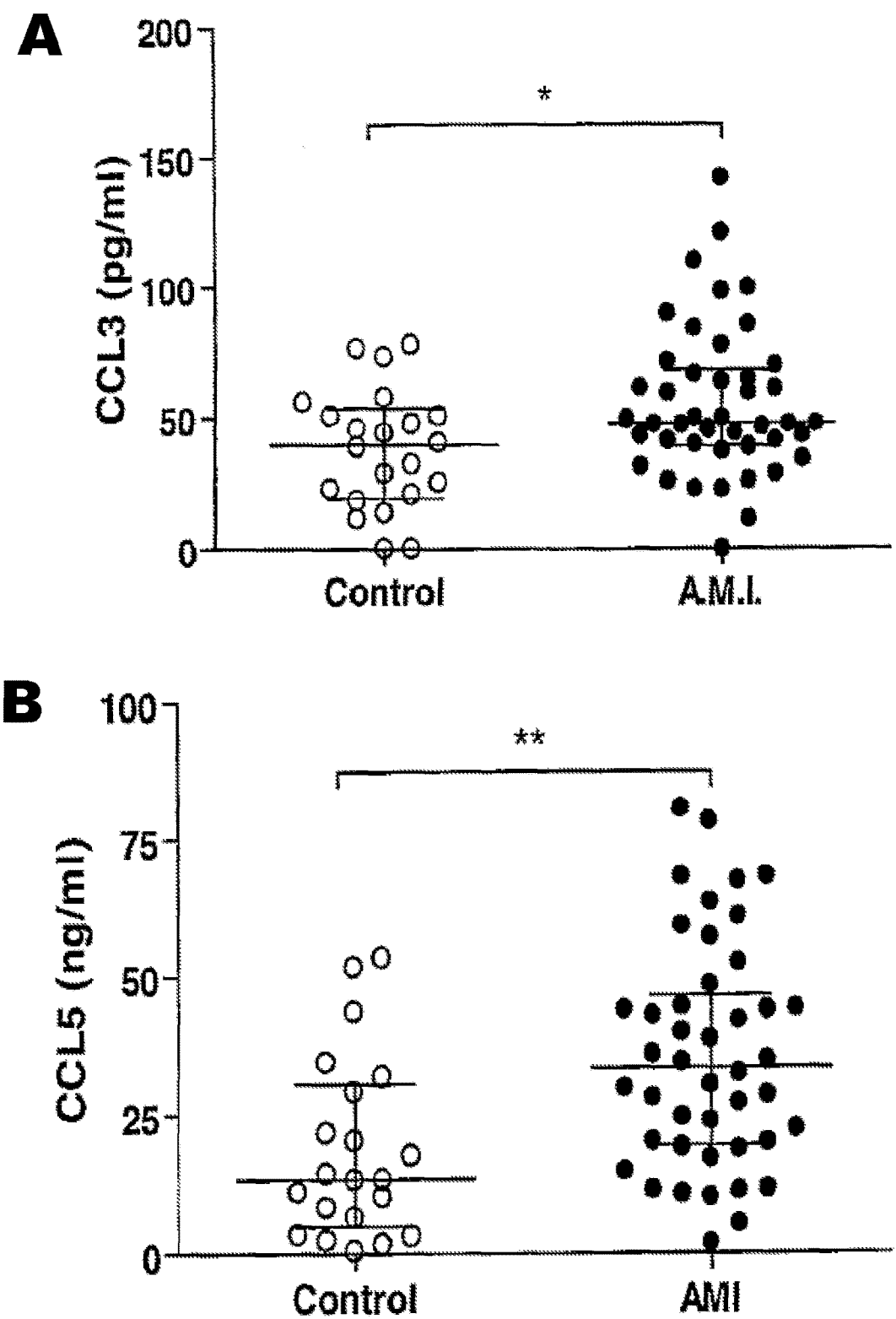
Figure 13:
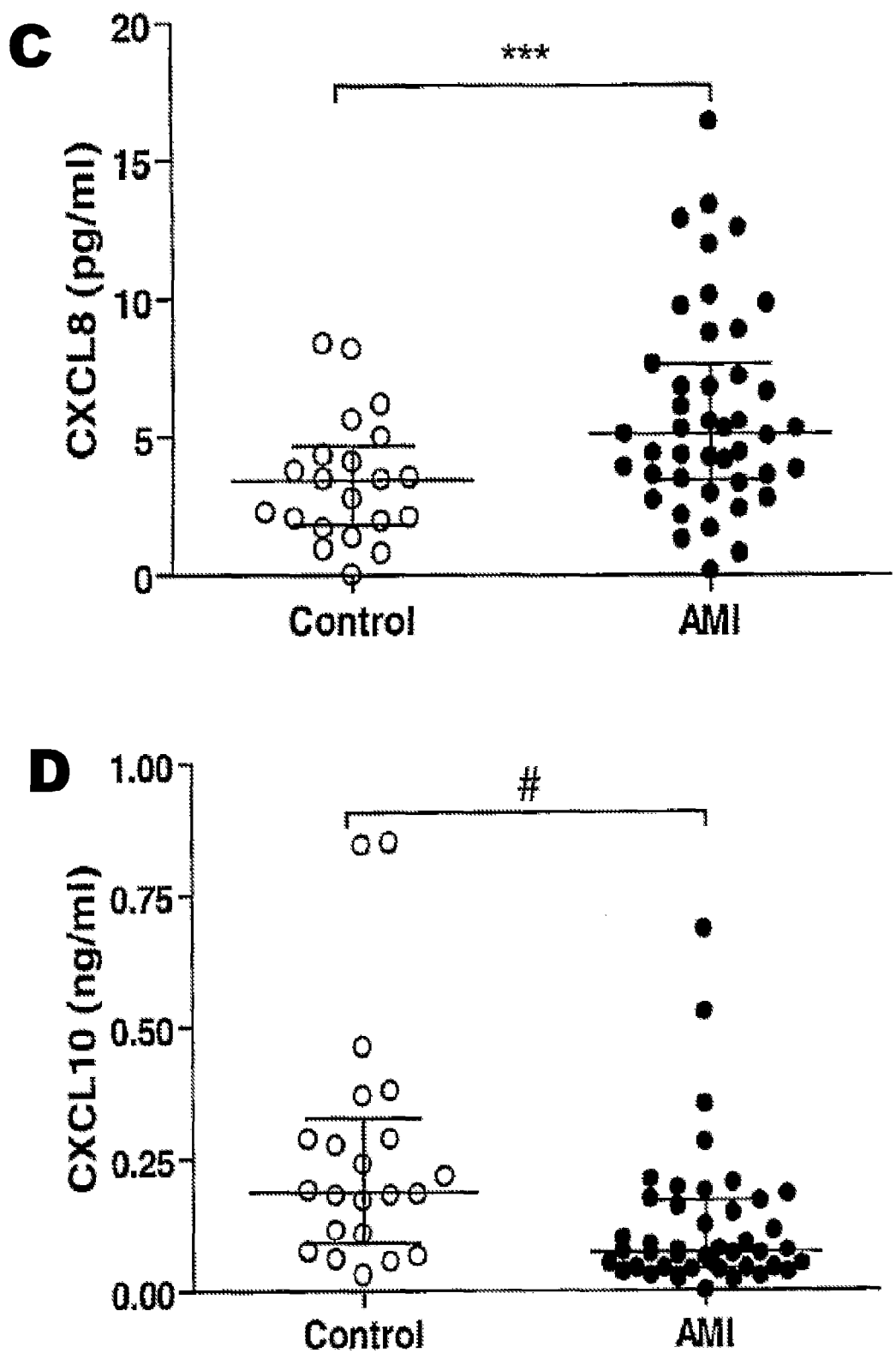

FIG. 13 graphically depicts levels of various chemokines. Plasma levels of CCL3 (A), CCL5 (B) and CXCL8 (C) were significantly elevated in AMI patients (●) versus controls (○), whereas CXCL10 (D) showed the opposite pattern. *P=0.025, P=0.006, *P=0.02 and #P=0.004.

Figure 14:
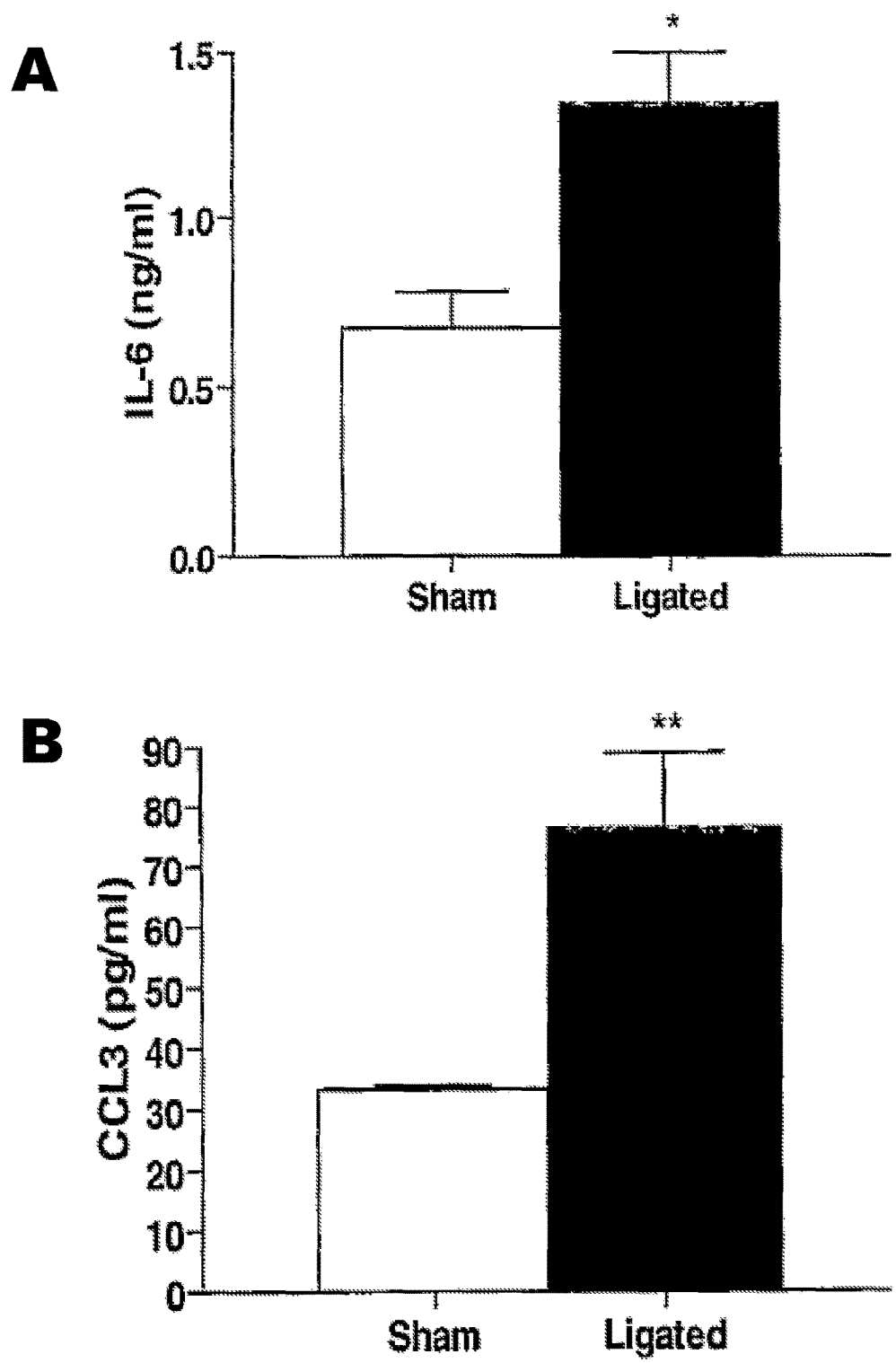

FIG. 14 graphically depicts assessment of IL-6, CCL3 and CXCL10 levels in LAD ligated or sham operated mice. Cardiac ischemia induced significantly elevated levels of IL-6, and CCL3, (A,B). On the other hand, CXCL10 displayed an inversed pattern (C). *P=0.007, P=0.02, and *P=0.03.

Figure 15:
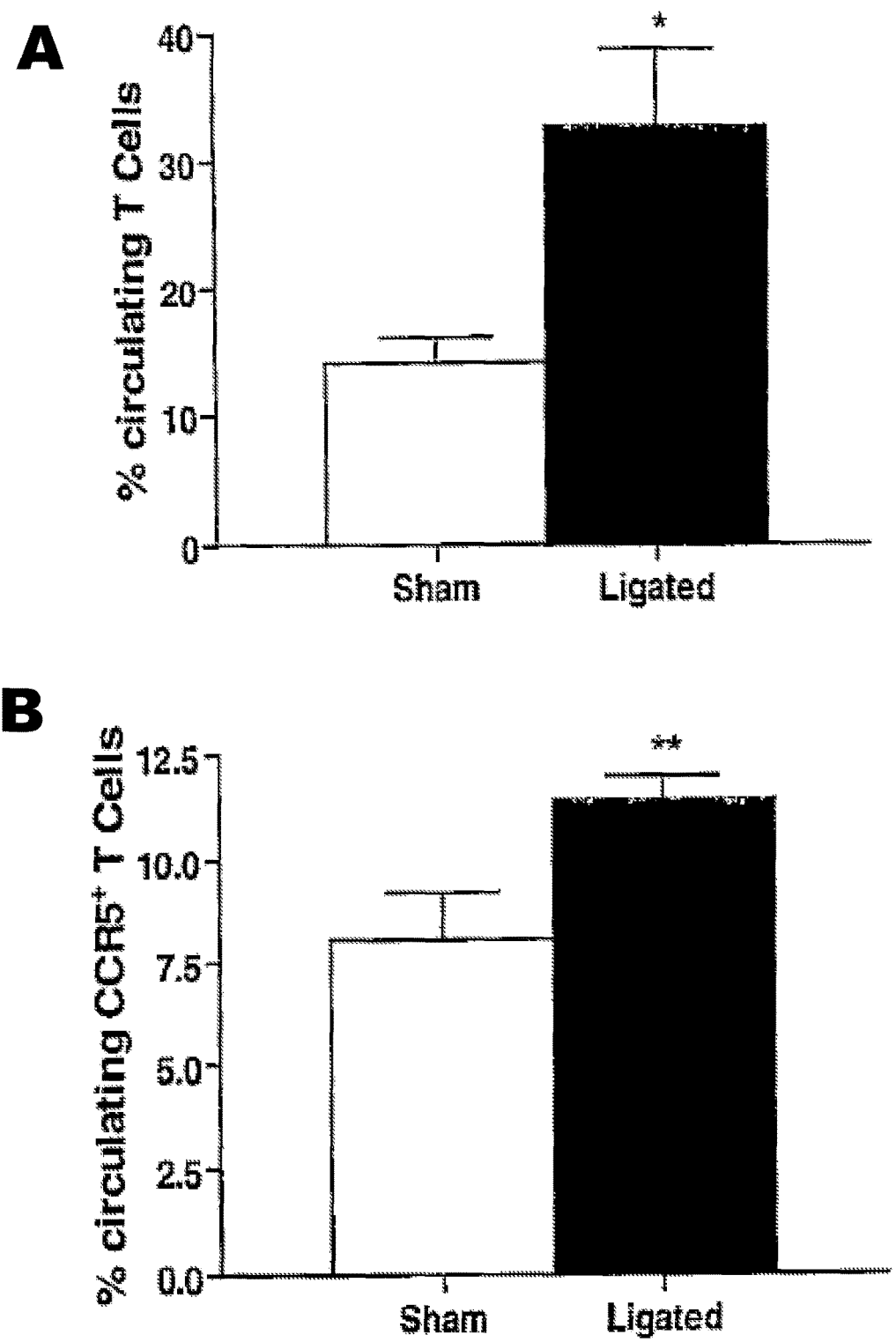
Figure 15:
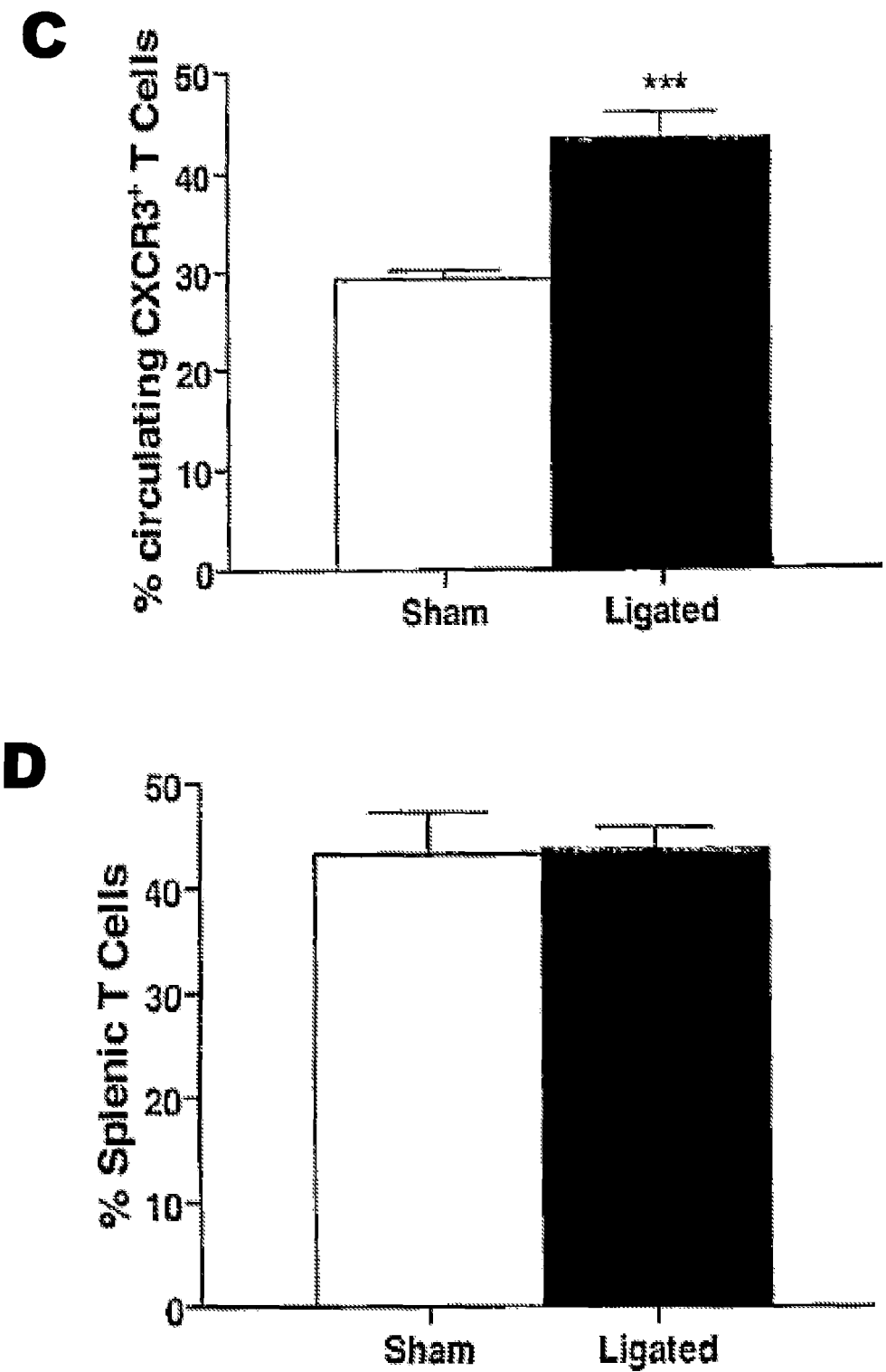
Figure 15:
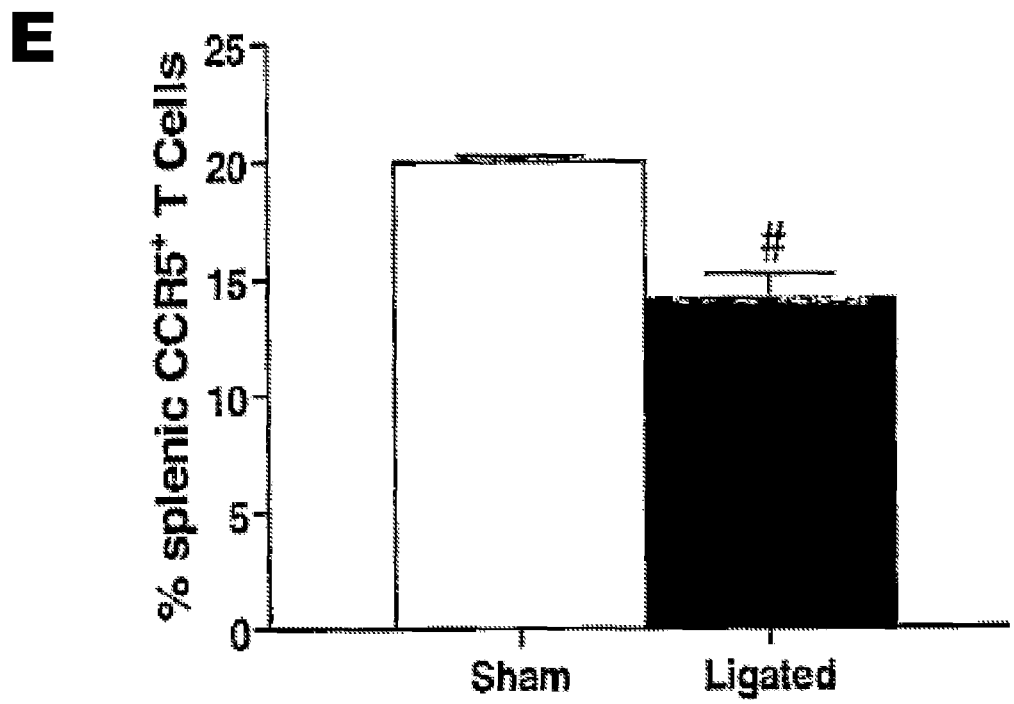
Figure 15:
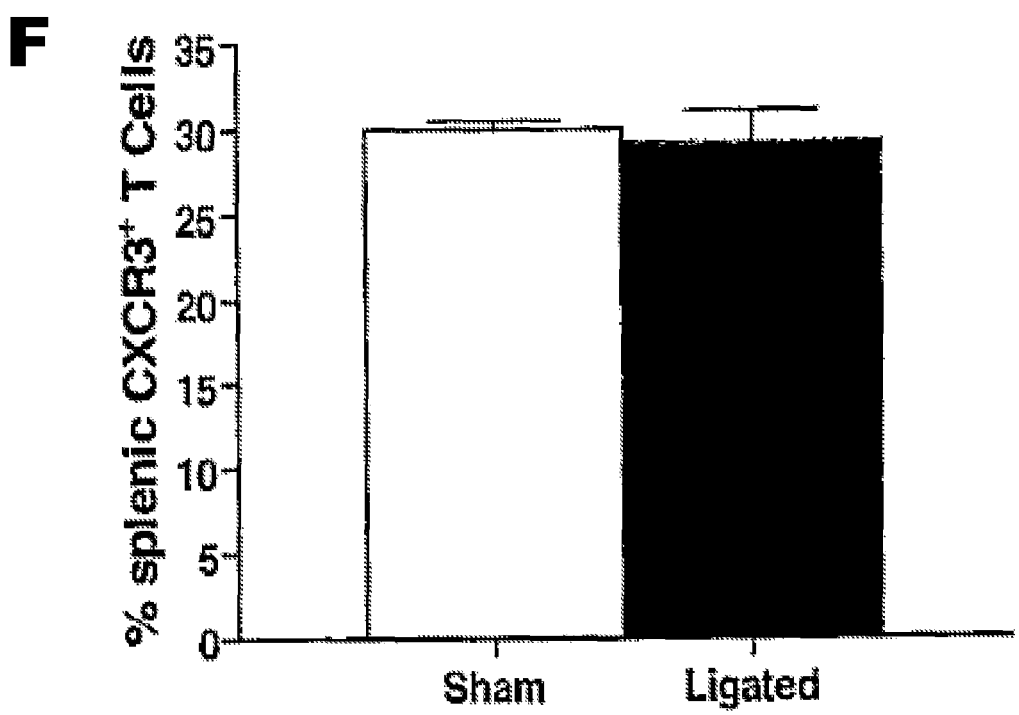

FIG. 15 depicts graphs demonstrating that ligated mice displayed a significant increase in the percentage of circulating T-cells with a concomitant enrichment in the CCR5+ and CXCR3+ subsets (A-C). The increase in circulating T-cells was accompanied by a decrease in CCR5+ splenic T-cells (E), whereas no effects on total (D) or CXCR3+ splenic T-cells was apparent (F). *P=0.04, P-0.02, *P=0.04 and #P=0.004.

Figure 16:
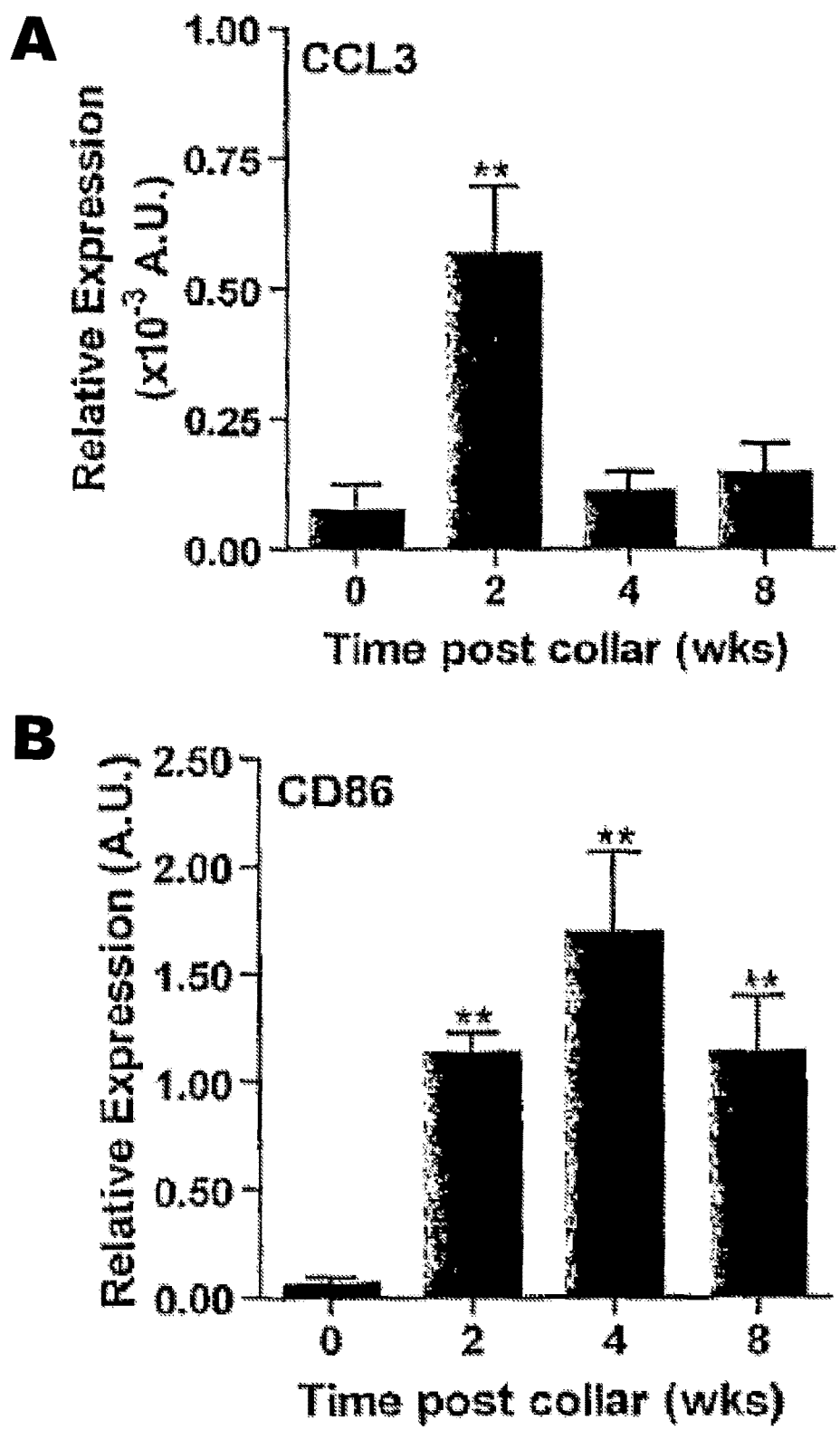
Figure 16C:
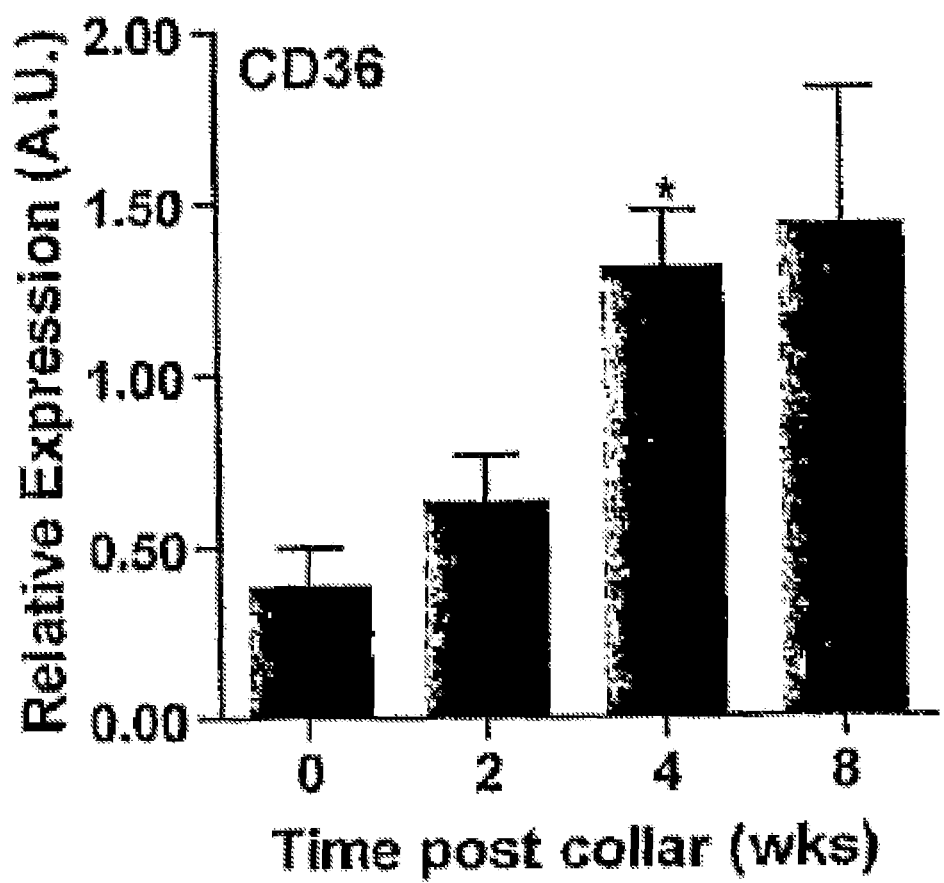

FIG. 16 depicts temporal profiling of CCL3, CD86 and CD36 expression in collar induced carotid artery plaque model. Collar induced carotid artery plaques showed increased CCL3 production 2 weeks after collar placement (A). Rapid and steady induction was observed for the macrophage marker CD68 (B), while CD36 induction was somewhat delayed (C). **p<0.01 compared to base line (t=0).

Figure 17:
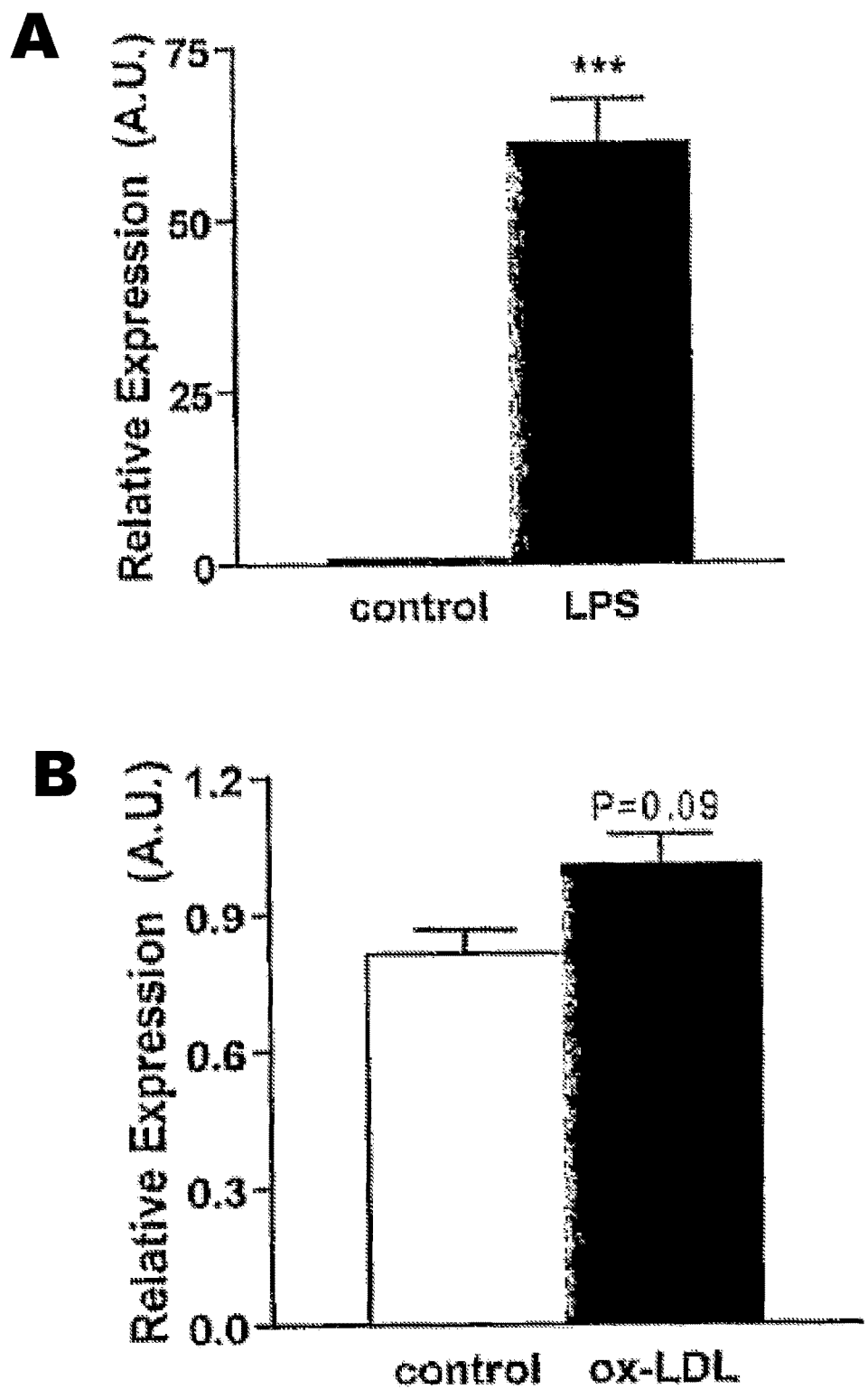

FIG. 17 depicts CCL3 expression in macrophages is strongly upregulated upon LPS (50 ng/ml) (A) but not ox-LDL (10 ug/ml) (B) stimulation. LPS induced CCL3 response in vivo is ablated in CCL3$^{-/-}$ chimeras (C, black bars)) ***p<0.001.

Figure 18A:
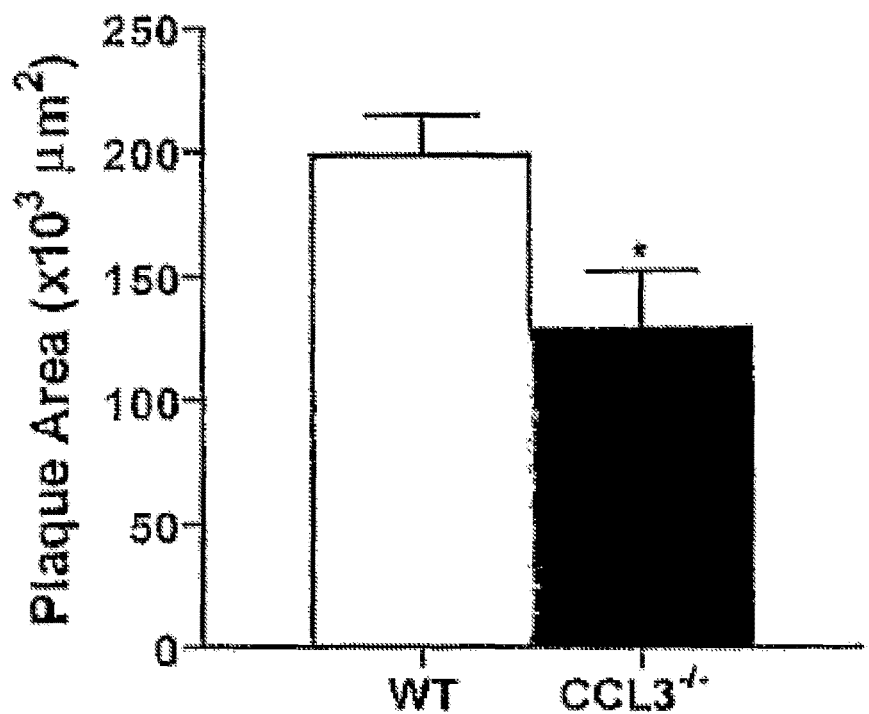
Figure 18A:
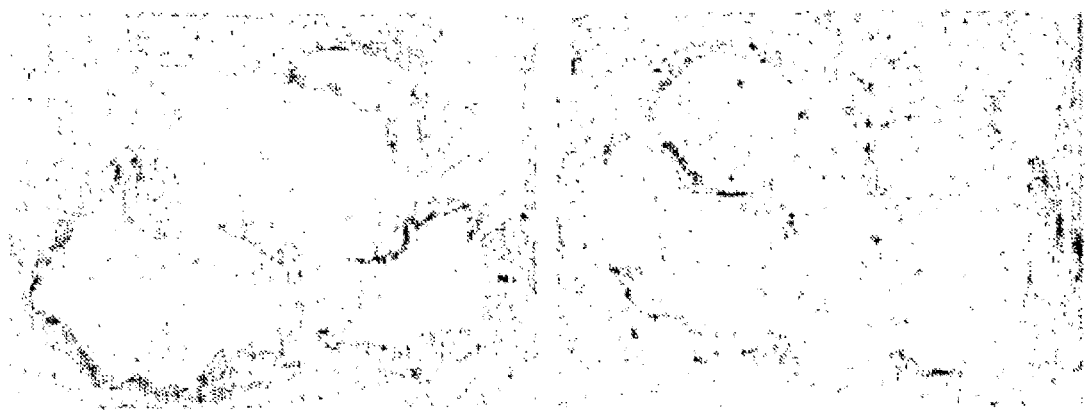
Figure 18:
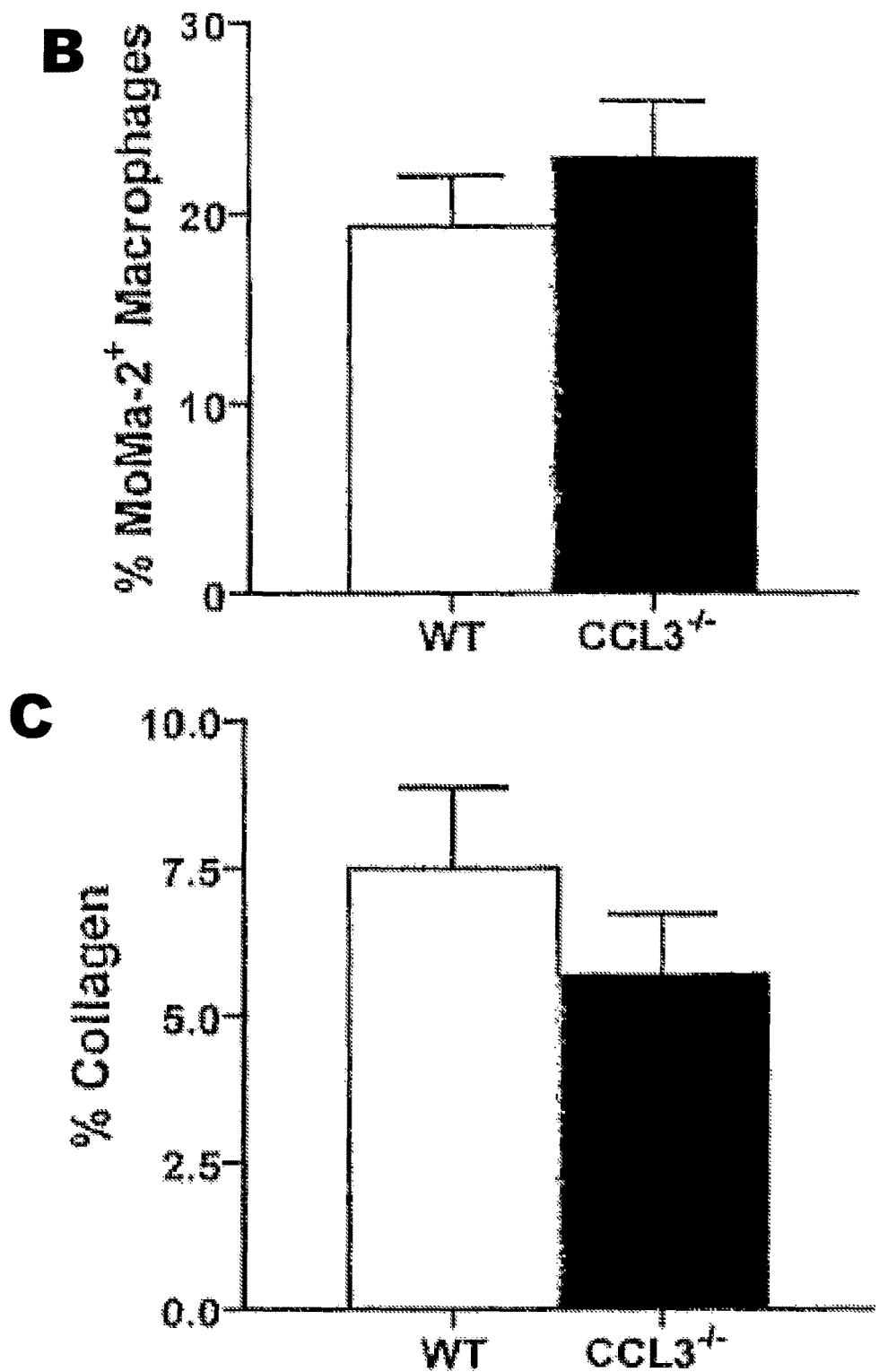
Figure 18:
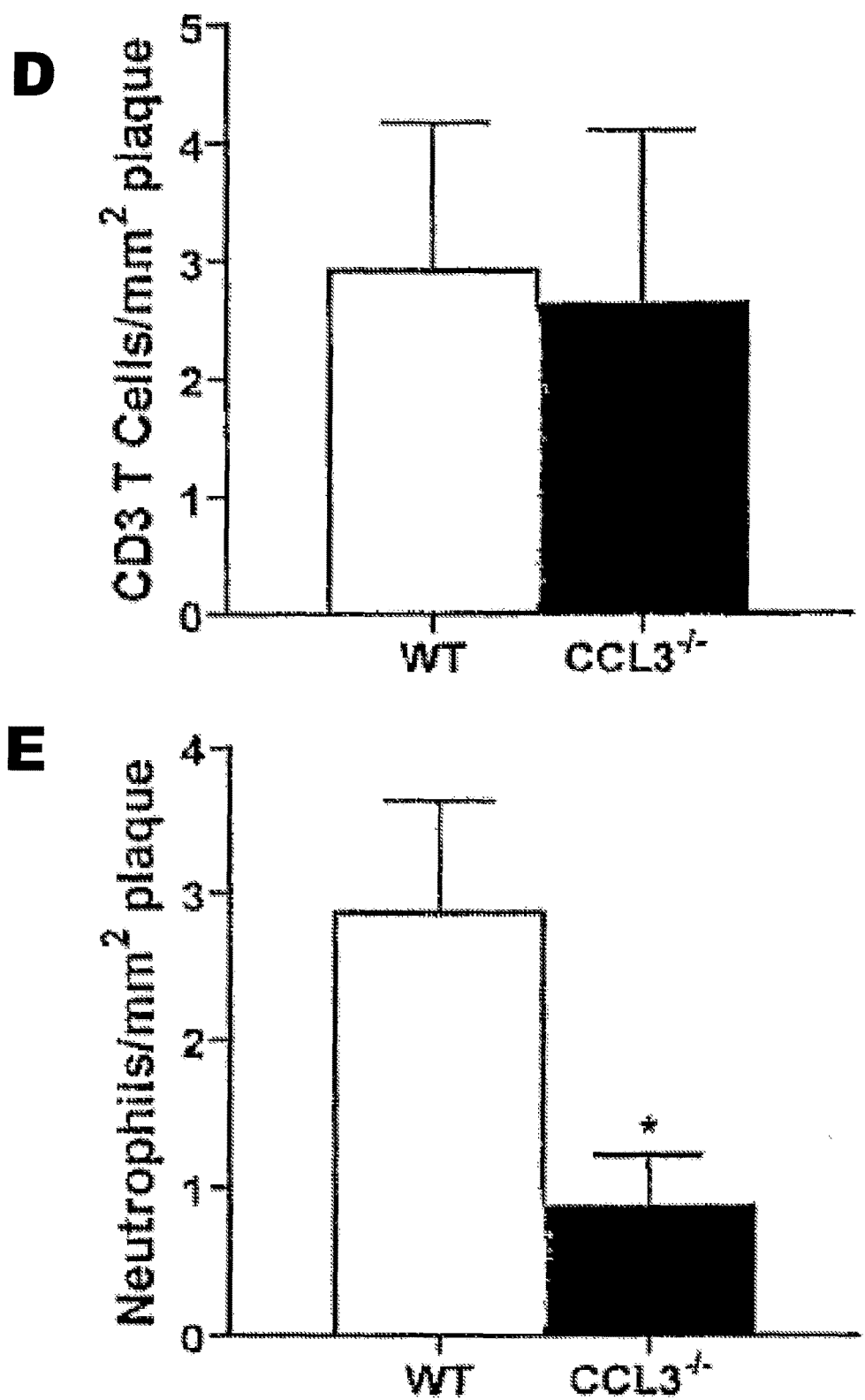

FIG. 18 depicts atherosclerotic lesions were significantly smaller in CCL3$^{-/-}$ chimeras compared to WT controls (A with representative pictures). Macrophages (B), collagen (C) and T cell content (D) was similar between WT and CCL3$^{-/-}$ chimeras. Neutrophil influx (E) and adhesion (F) was significantly attenuated in CCL3$^{-/-}$ chimeras. White bars represent WT controls and black bars CCL3$^{-/-}$ chimeras. *p<0.05, **p<0.01.

Figure 19:
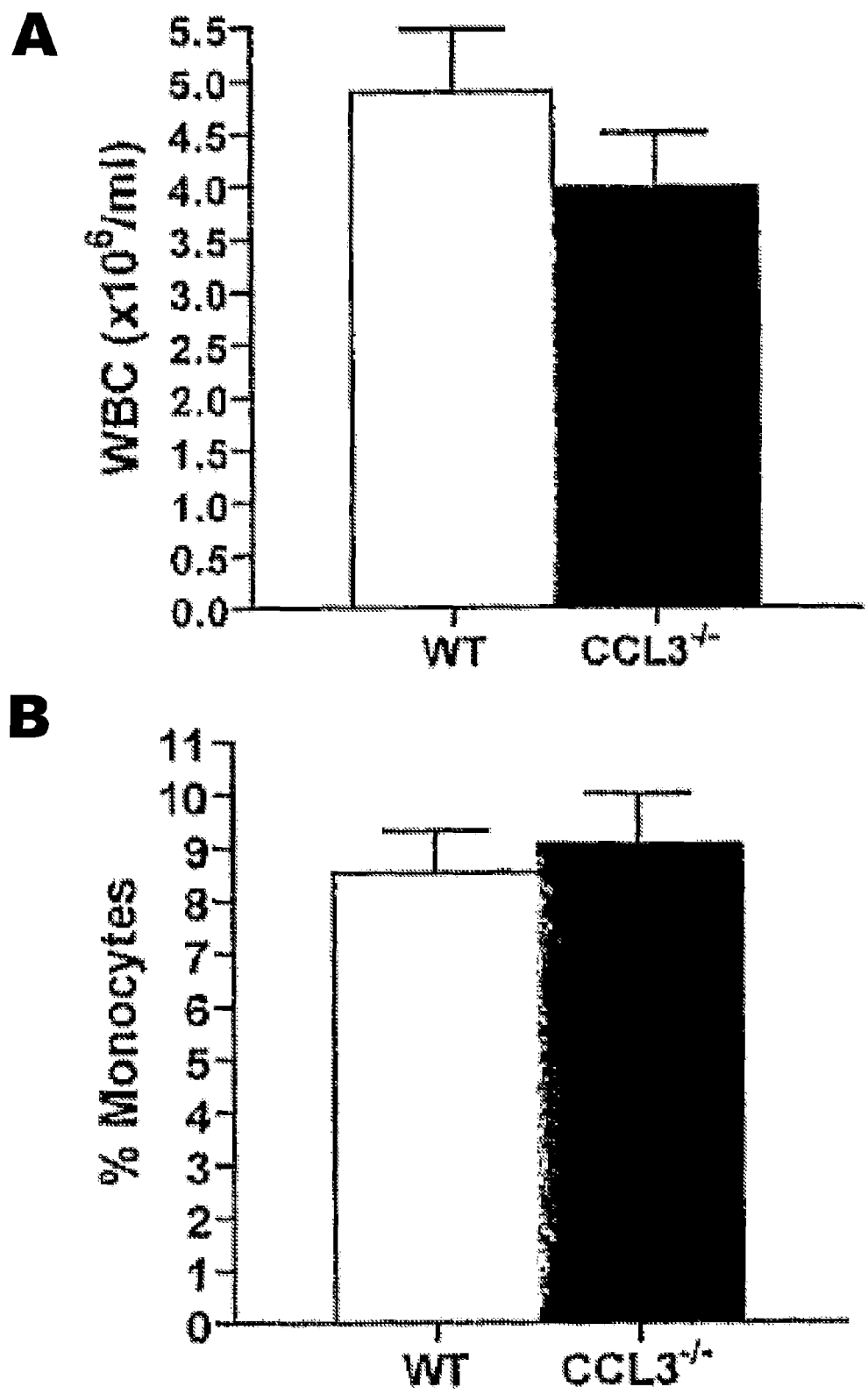

FIG. 19 depicts total number of white blood cells (A; WBC) and percent monocytes (B) was not different in CCL3$^{-/-}$ mice, whereas neutrophil numbers (C) were significantly decreased. White bars represent WT and black bars CCL3$^{-/-}$ chimeras. p<0.01, *p<0.001.

Figure 20:
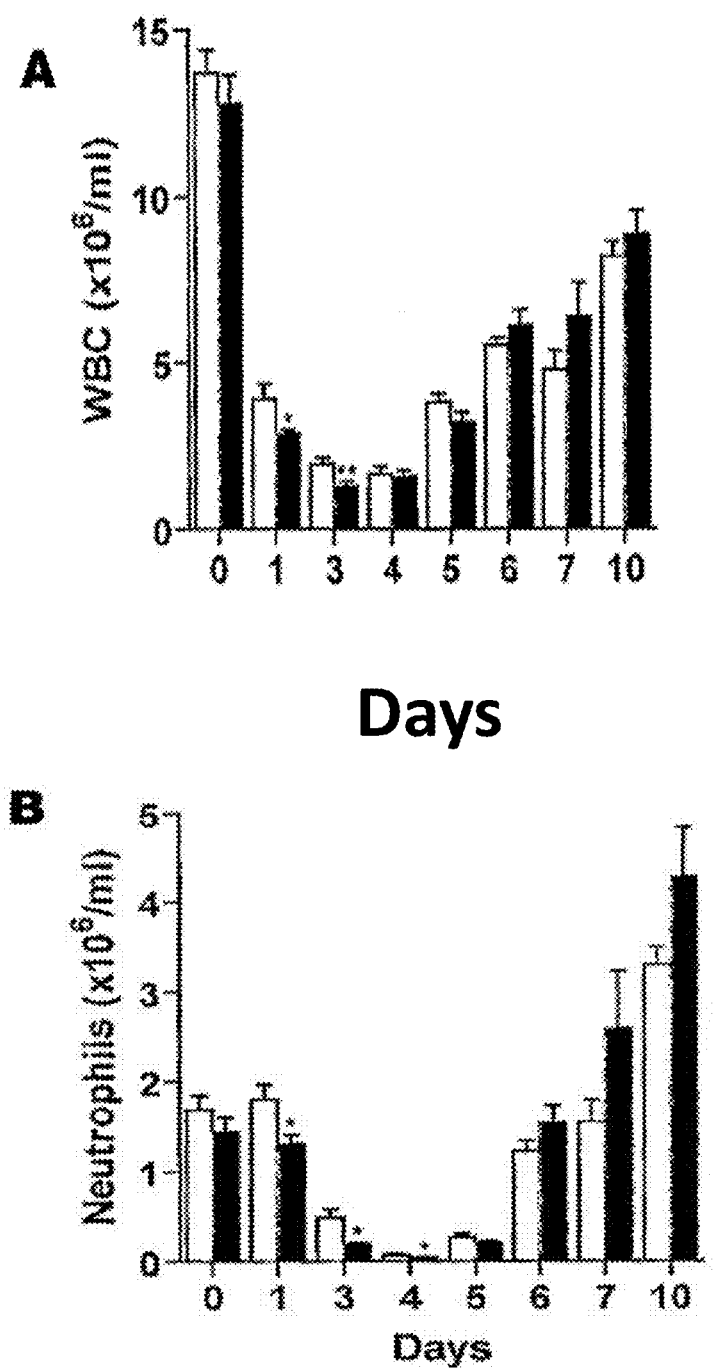
Figure 20:
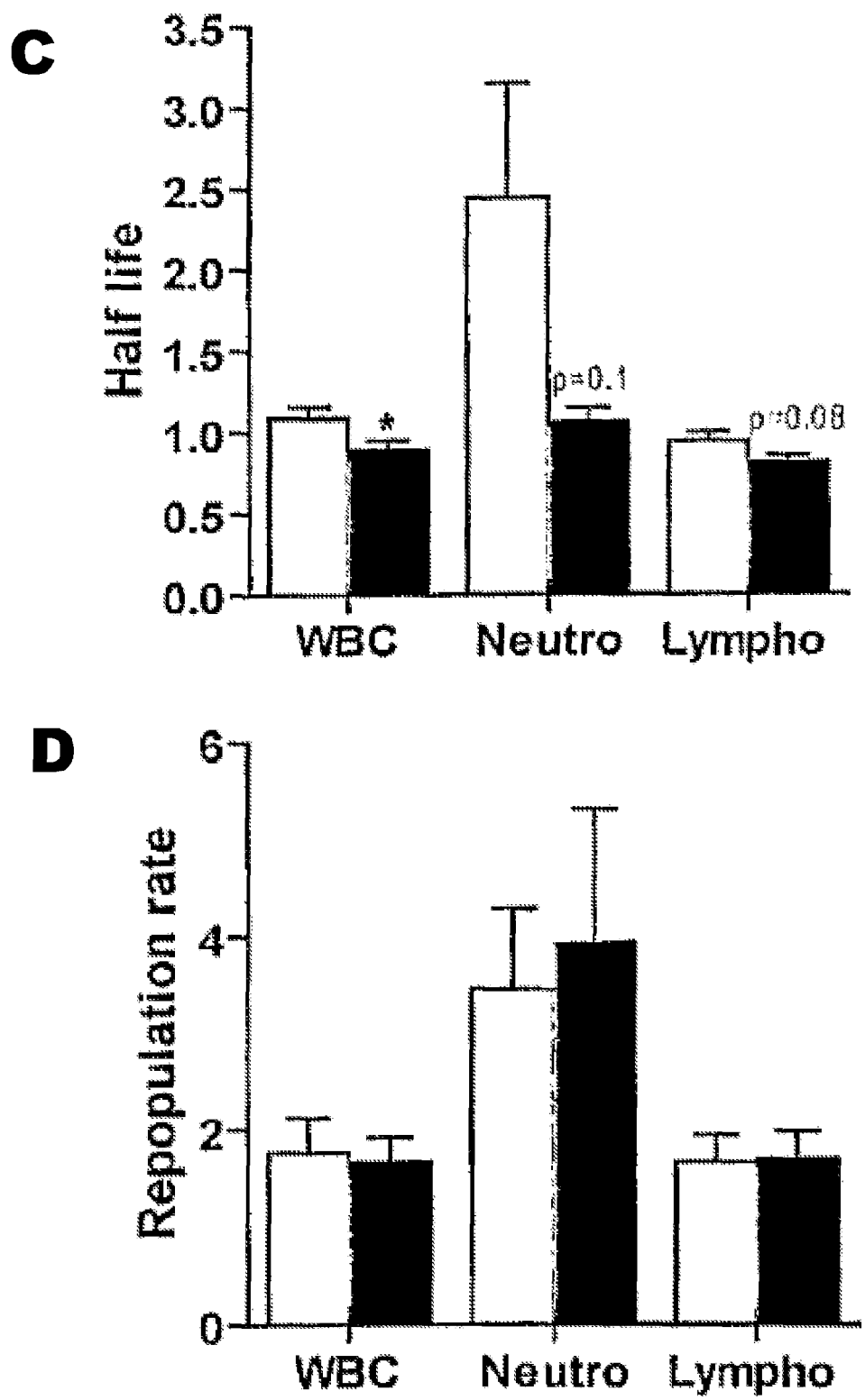

FIG. 20 depicts kinetics of cyclophosphamide induced transient leukopenia (A; WBC on y-axis) and neutropenia (B; neutrophil count on y-axis) in control (white bars) and CCL3$^{-/-}$ mice (black bars). Elimination of neutrophils is accelerated in CCL3$^{-/-}$ chimeras (C), while repopulation is similar (D). Black bars represent WT mice and white bars represent CCL3$^{-/-}$ mice. *p<0.05. **p<0.01.

Figure 21:
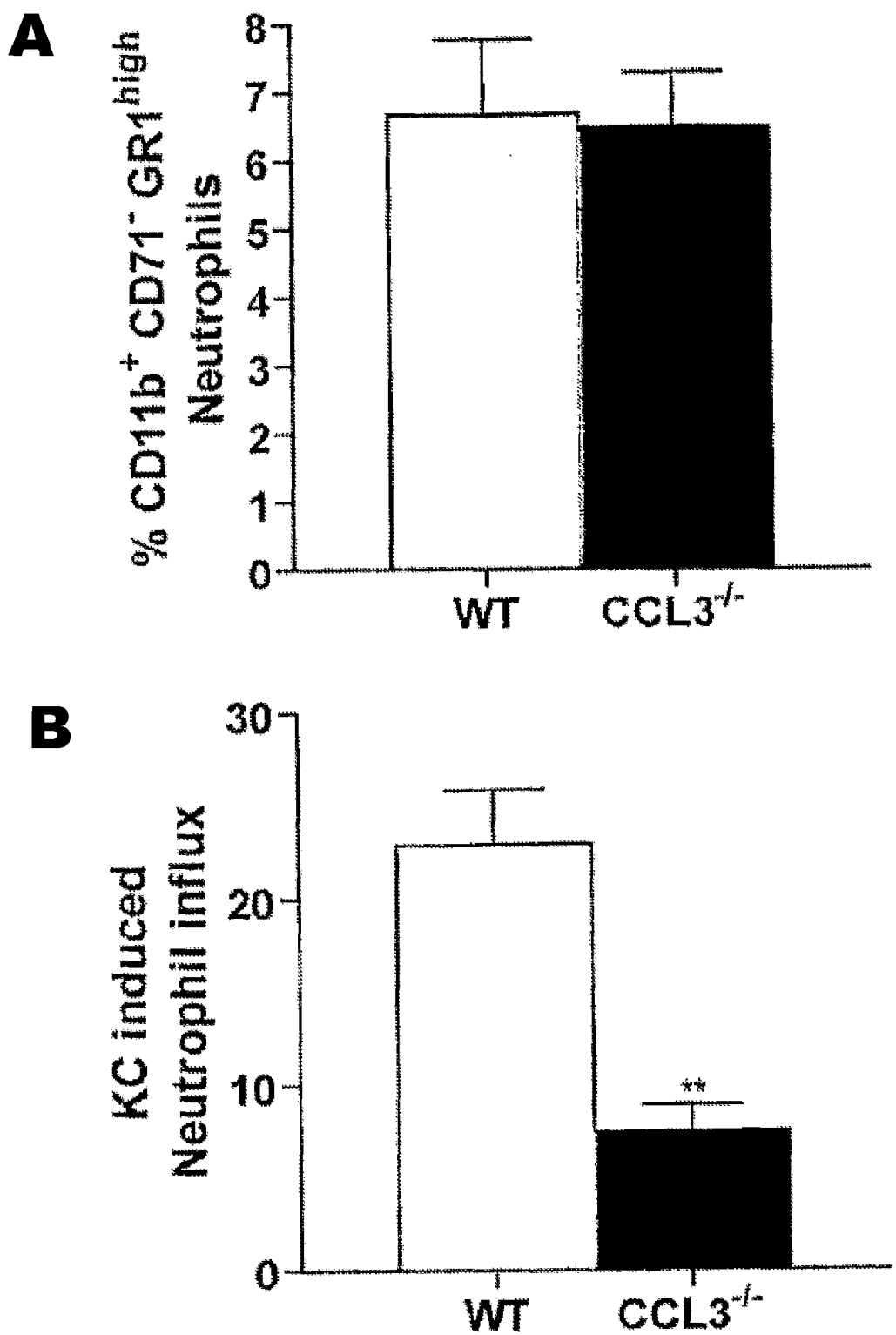
Figure 22:
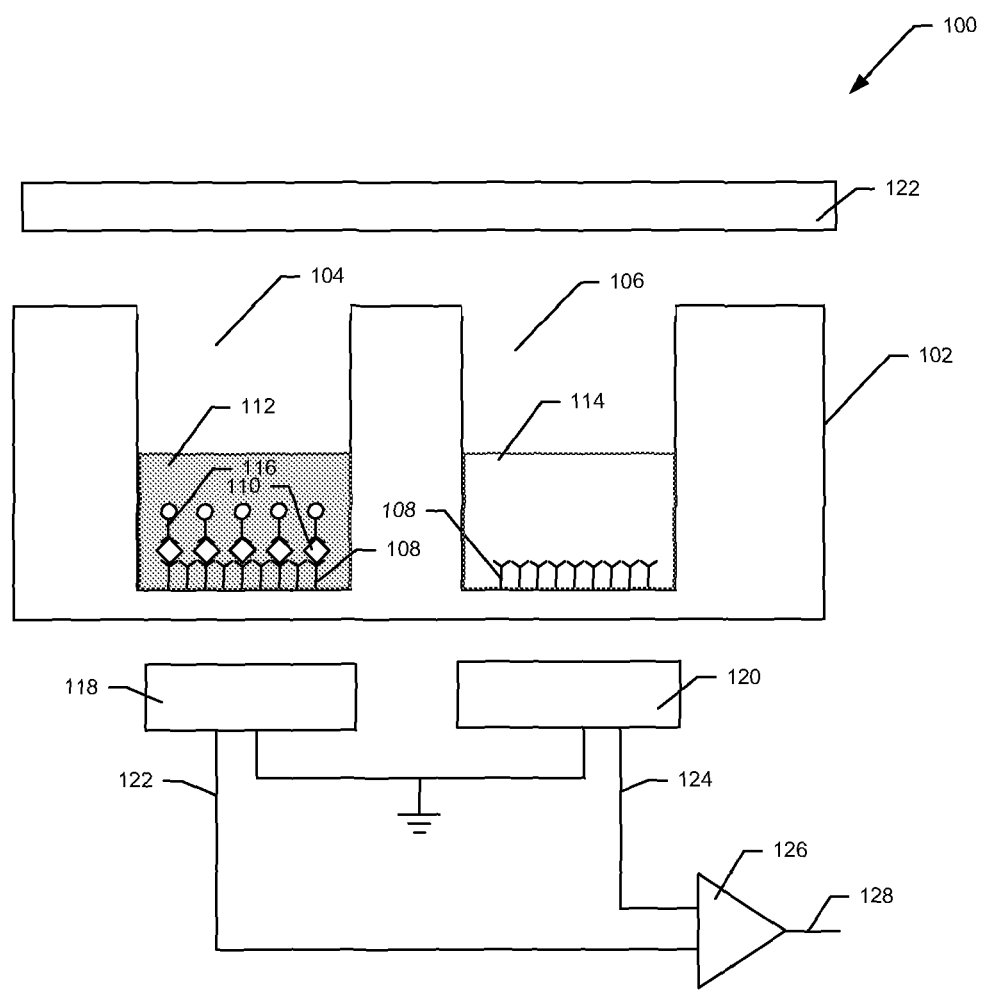

FIG. 21 depicts intra peritoneal injection of KC did not affect circulating CD11b+ CD71-Gr1$^{high}$ neutrophil numbers in WT and CCL3$^{-/-}$ mice (A). KC elicited induction of neutrophil influx to the peritoneal cavity was ≈2.5 times lower in CCL3$^{-/-}$ mice compared to WT mice (B). White bars represent WT mice and black bars represent CCL3$^{-/-}$ mice. **p=0.003, FIG. 22 is a schematic illustration of the device.

Figure 23:
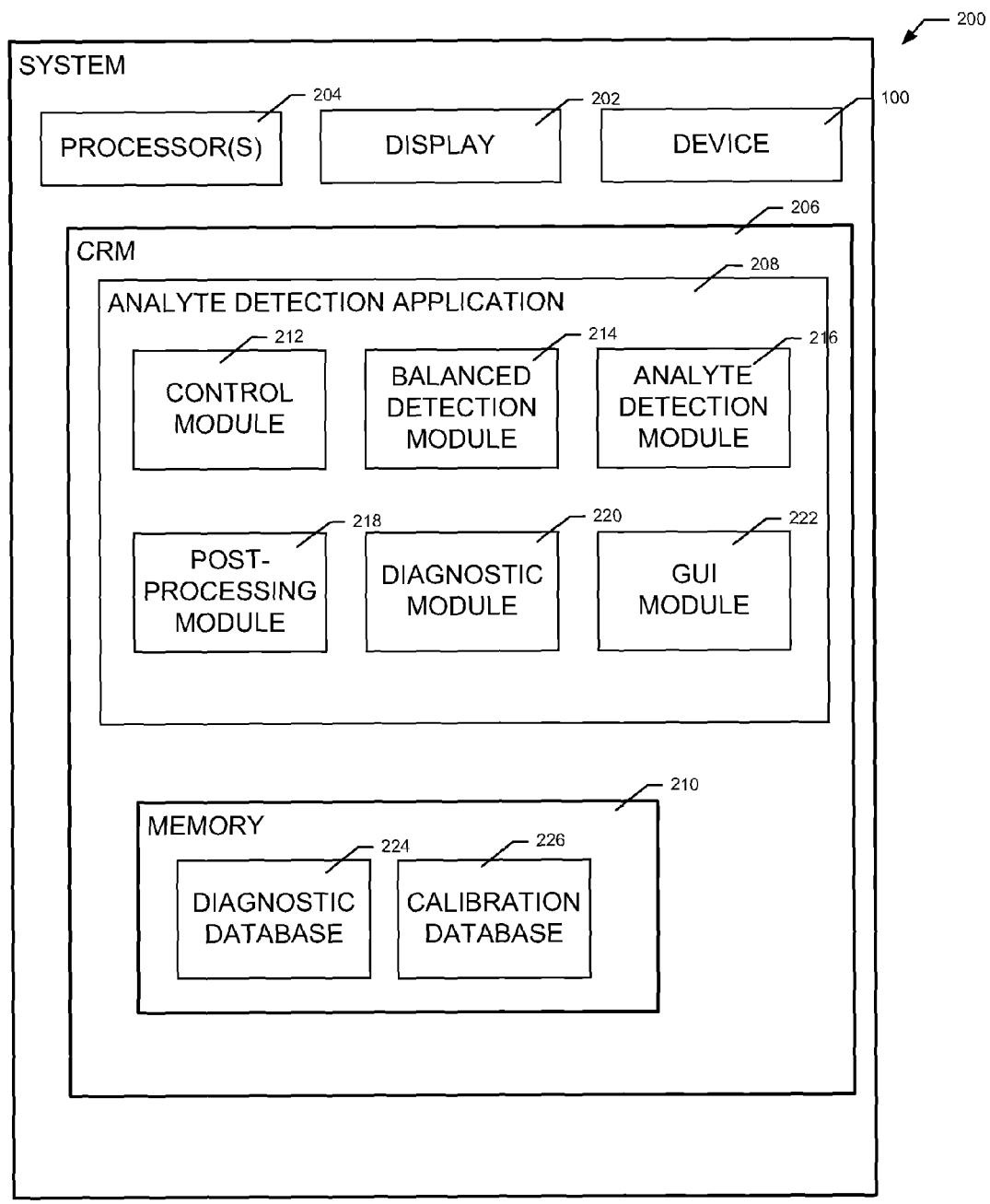

FIG. 23 is a block diagram illustrating the elements of a system.

Figure 24:
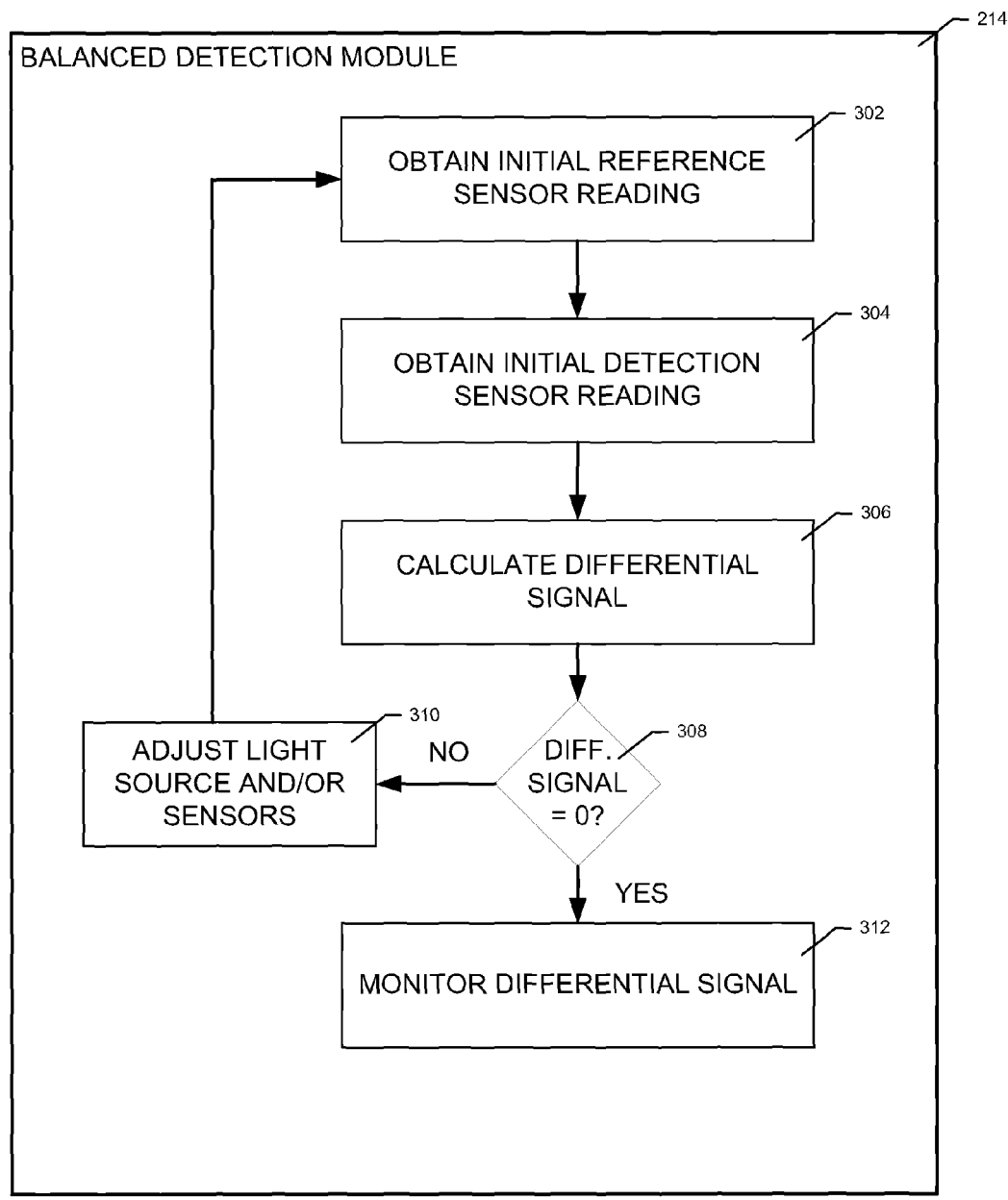

FIG. 24 is a flow chart illustrating the operation of the balanced detection module.

Figure 25:
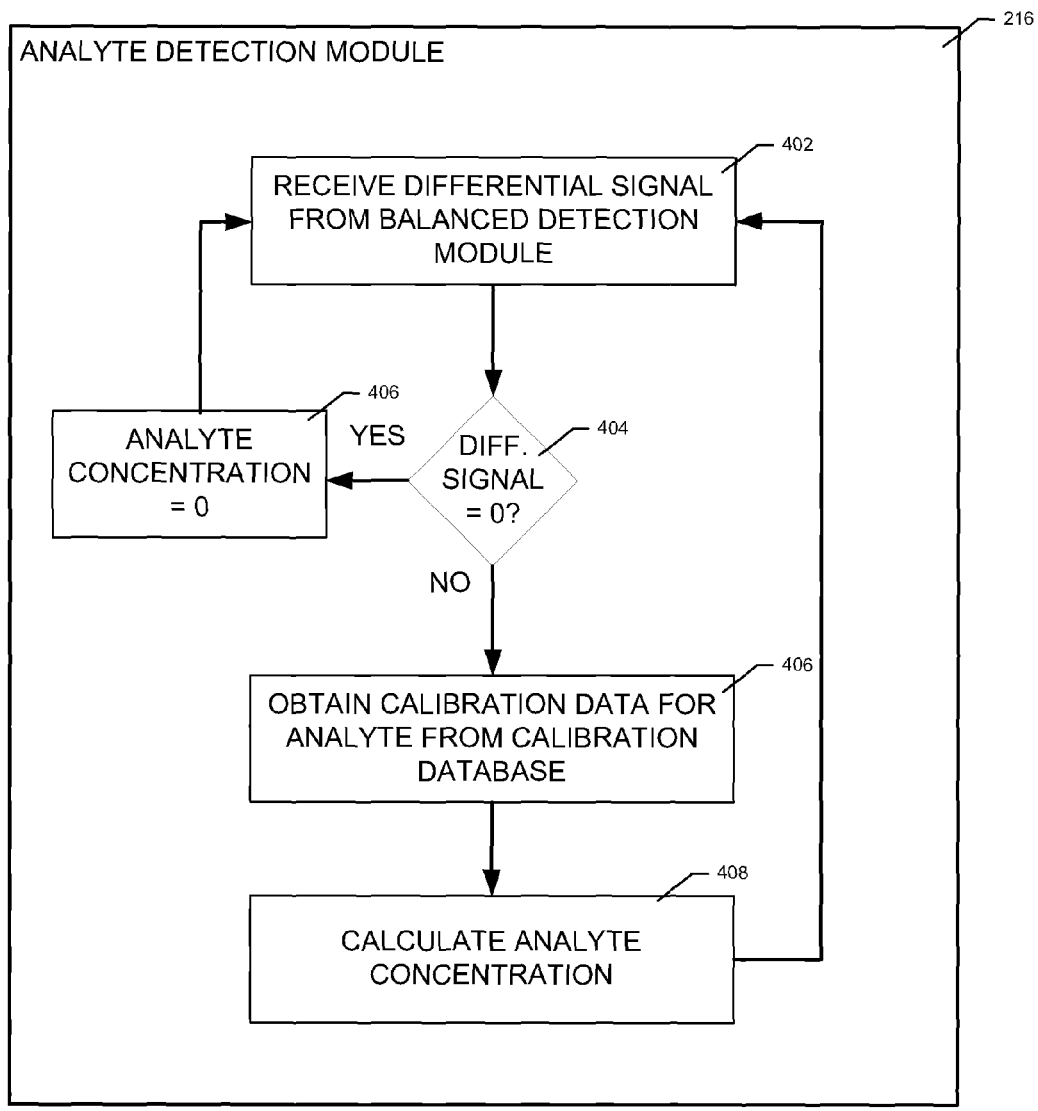

FIG. 25 is a flow chart illustrating the operation of the analyte detection module.

Figure 26:
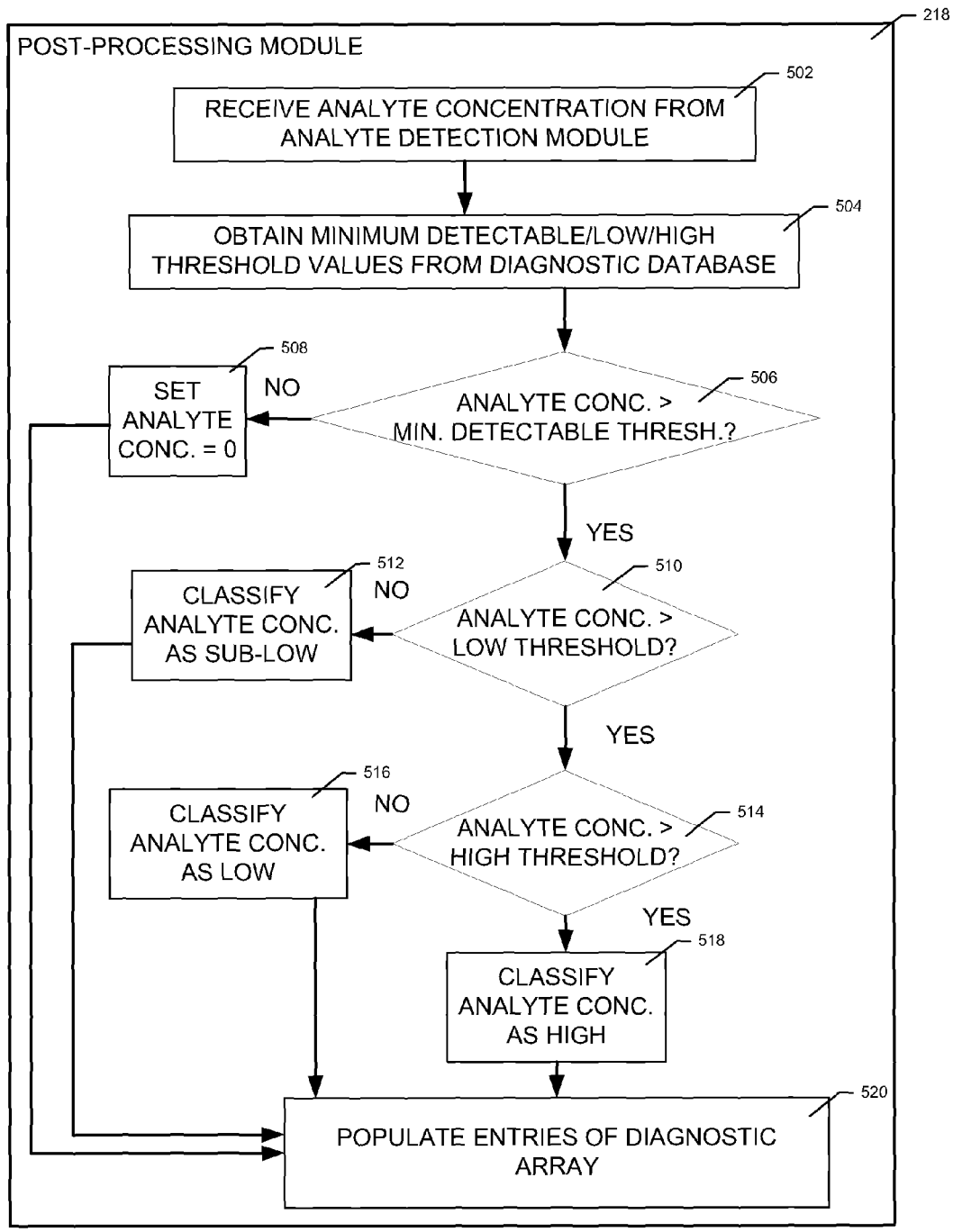

FIG. 26 is a flow chart illustrating the operation of the post-processing module.

Figure 27:
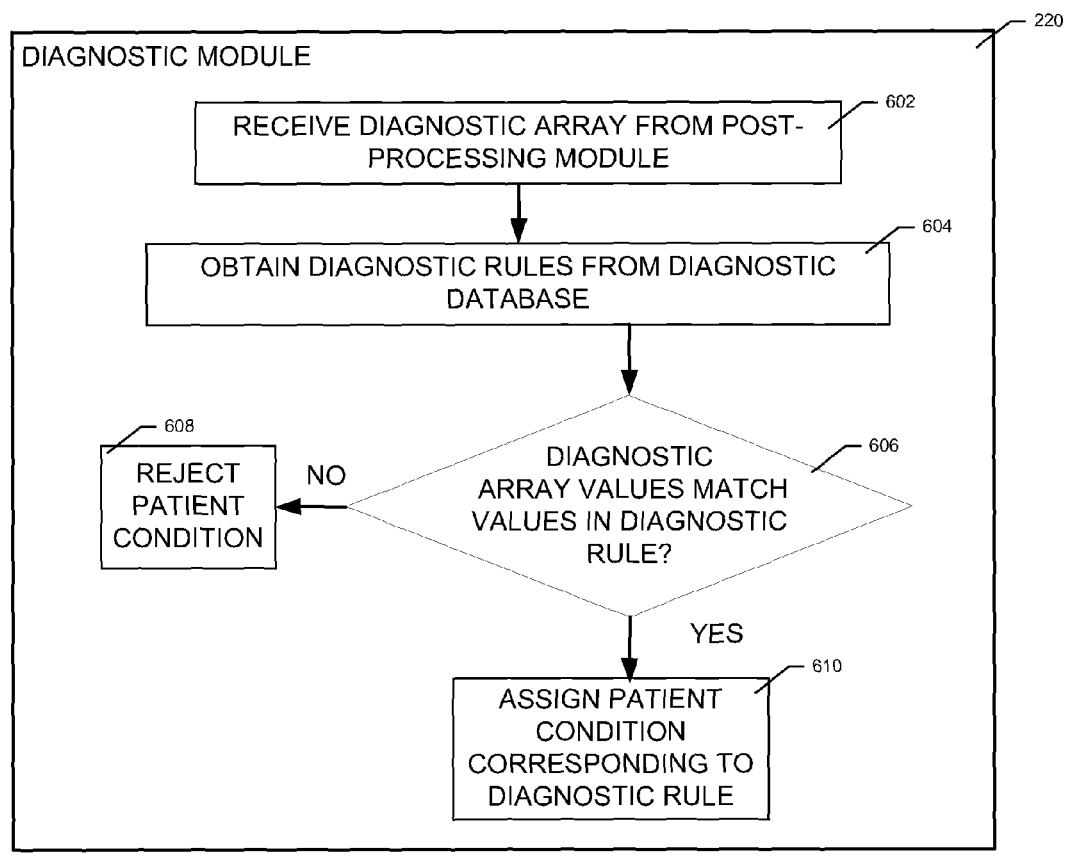

FIG. 27 is a flow chart illustrating the operation of the diagnostic module.

Figure 28:
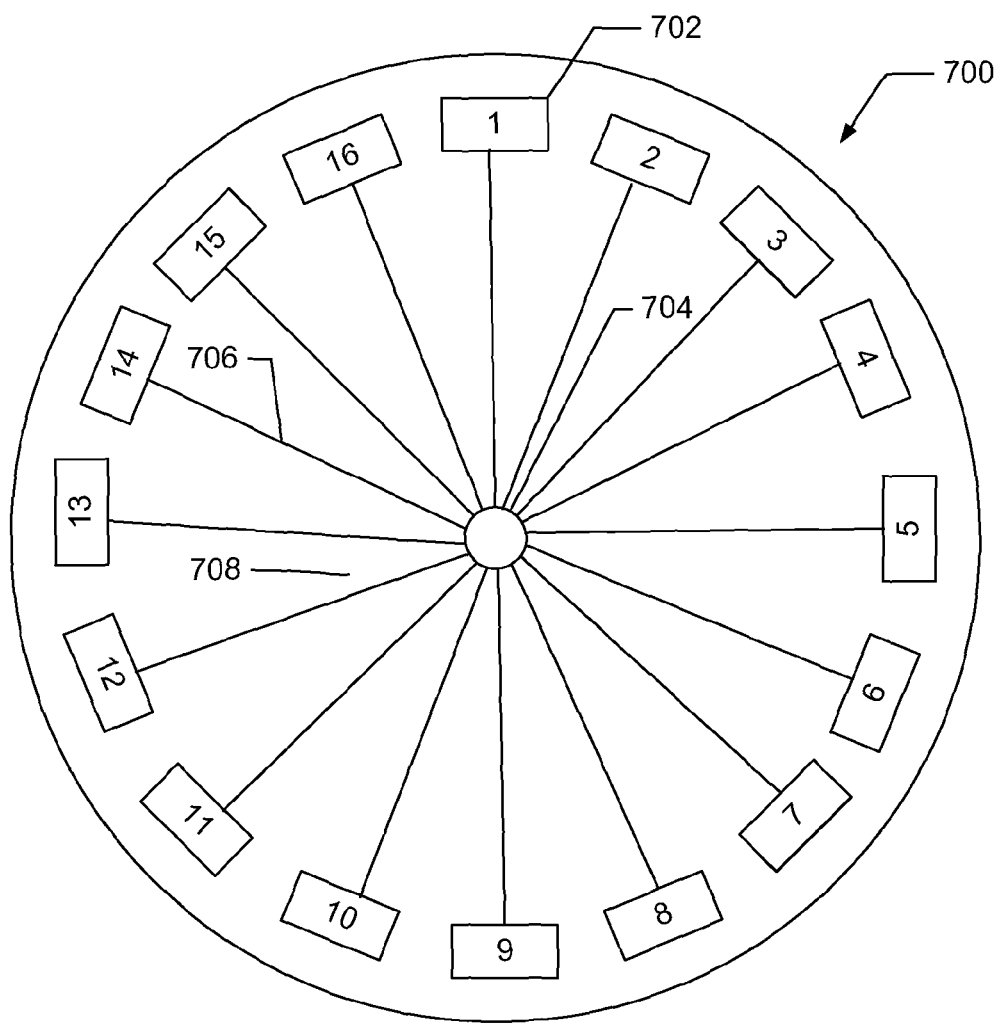

FIG. 28 is schematic illustration of a top view of a surface.

FIG. 29 is a schematic illustration of the device in an embodiment. (A) depicts an embodiment in an initial condition, and (B) depicts an embodiment during an enzymatic reaction.

Figure 30:
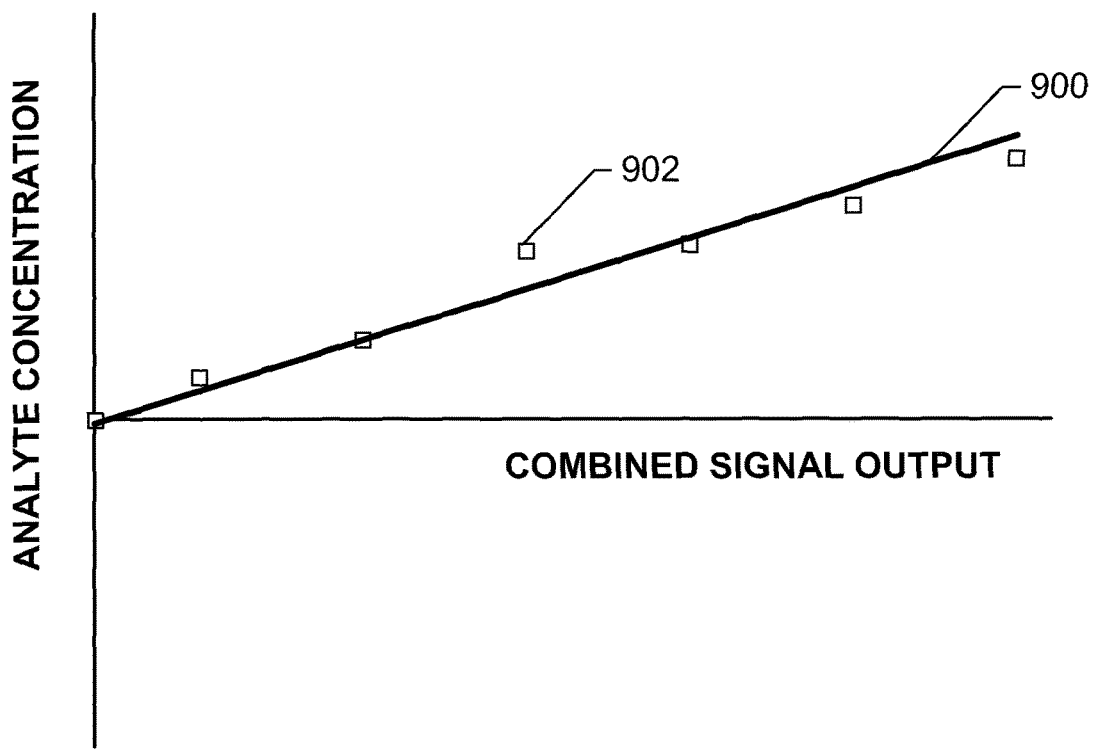

FIG. 30 is an illustrative example of an analyte calibration curve.

Corresponding reference characters and labels indicate corresponding elements among the views of the drawings. The headings used in the figures should not be interpreted to limit the scope of the claims.

DETAILED DESCRIPTION

Provided herein are devices, systems, and methods for detecting analytes from a multiplex reaction. The detection device may include a complementary metal-oxide-semiconductor (CMOS) image sensor. In an aspect the CMOS sensor may be designed to capture/measure balanced image detection resulting from a multiplex reaction of select microarrayed analytes to report discrete quantities of individual and/or combined target analytes resulting from a detection reaction. The detection reaction of multiplexed microarrayed analytes may be conducted using the device with the expectation of the device to measure and report discrete quantities or combinations of discrete analytes providing information to aid in the prognosis and/or diagnosis of altered states of health in vertebrates. Demonstrating the sensitivity of a multiplexing approach to detect quantities of target analytes in a bodily fluid, coupled with balanced image detection designed specifically to measure the results of a detection reaction proved the scientific principles to enable a CMOS based technology as a balanced image sensing detection, and quantification system for select analytes in a fluid medium.

Further this novel, lightweight, portable, low energy device designed to detect biomarkers of disease by multiplexing proteins and/or nucleic acids is also capable of utilizing low level ambient light and ambient temperature to detect the target analytes/biomarkers found in vertebrate bodily fluids. Claims within the scope of the patent include novel methods to multiplex a microarray of analytes, the combination of results providing information to prognose or to diagnose an altered state of health. Methods to measure said analytes is accomplished by adapting the principles of balanced detection capable of utilizing a low level of light supported by a low energy source. The detection method is capable of distinguishing the individual concentration of 1 target analyte, or the individual values of multiple target analytes, and through the use of software report a ratio of multiple analytes to each other and to standards. The balanced detection method enables a portable low cost light weight device capable of reporting on multiple analytes in a rapid manner by, in some embodiments, adapting an ELISA reaction or similar detection reaction. The balanced detection method may be adapted using CMOS chip(s) to image the low light difference between groups of pixels monitoring the designated reaction wells and non-reaction (reference) wells. The CMOS image sensing system incorporating a modified ELISA reaction, and low level lighting system detects either an individual or multiple analytes, and reports using a novel algorithm to provide an output in graphic form or discrete measurements of the target analytes.

The validation prototype of the balance detection adapted to capture and report an ELISA reaction of proteins, nucleic acid material, polysaccharides, or other substances which can be measured or detected by an enzymatic process demonstrates the substrate, ELISA reaction well, low level light, portability, stability, and low energy consumption. The prototype system incorporates an approach that is able to use minimal light, reduces time of the enzymatic reaction compared to standard laboratory methods, and is able to modulate ambient light to enable standardizing the control as needed in differing environments. All reactions are able to be conducted in ambient temperature.

Detailed descriptions of various aspects of the rapid detection devices, as well as associated systems and methods of using the devices are provided herein below.

I. Device

In various embodiments, a device for the rapid detection of one or more analytes from a bodily fluid sample is provided. The device may be configured to receive a bodily fluid sample and to further subject the sample to a detection reaction to detect the one or more analytes in the sample. The detection reaction, as described herein in detail below, includes multiple steps such as analyte capture and tagging of the captured analyte, but does not require other steps such as washing, thereby reducing the time required to detect each analyte. In addition, in certain embodiments, the detection reaction incorporates highly selective monoclonal antibodies, thereby providing for multiplex detection of more than one analyte from a single bodily fluid sample and further reducing the overall time required to detect the one or more analytes.

In various embodiments, the device may use a balanced sensor detection methodology to detect and/or quantify the one or more analytes using the difference in readings measured from one or more pairs of light sensors: a first light sensor situated near an analyte detection region and a second light sensor situated near a control or standard region. The balanced sensor detection methodology enhances the sensitivity of the device, providing the ability to detect the one or more analytes under a variety of lighting conditions including, but not limited to, low light or ambient light conditions.

The device in various embodiments incorporates multiplex analyte detection and provides valuable diagnostic information in a timely manner to inform decision making by the subject or the subject's physician in a variety of clinical, point-of-care, and/or home settings. The methods and elements of the device are capable of functioning at room temperature with minimal need for environmental control. In addition, the device is capable of obtaining measurements even in minimal light by modulating the ambient light to enable standardizing the control as needed in differing environments.

FIG. 22 is a schematic illustration of the device 100 in one embodiment. As illustrated in FIG. 22, the device 100 may include a surface 102 for conducting a detection reaction including, but not limited to, the modified ELISA method. The surface 102 may be provided with a detection region 104 and a reference region 106. The detection region 104 and a reference region 106 may be provided in a variety of forms without limitation including, but not limited to, depressions or wells as illustrated in FIG. 22. Both the detection region 104 and the reference region 106 may contain one or more epitope binding agents 108 for capturing one or more analytes 110 from within the sample.

In use, a sample 112 containing one or more analytes 110 may be introduced into the detection region 104, and a reference substance 114, which does not contain the one or more analytes 110 may be introduced into the reference region 106. Alternatively, a reference substance 114 may contain analytes in known amounts. In another alternative, the reference region 106 may comprise analyte in known amounts absorbed to the reference region. In still other embodiments, the reference region 106 may comprise known amounts of analyte absorbed in specific known locations (e.g. patterns) to the reference region. Within the detection region, the one or more analytes 110 may participate in a detection reaction which may alter the optical properties of the detection region 104. For example, the detection reaction may capture the one or more analytes 110 using the one or more epitope binding agents 108 and may further bind one or more tagged detection epitopes 116 to the captured analytes 110, thereby causing the formation of opaque reaction products that reduce the light transmission properties of the detection region 104.

The device 100 may further include a light source 122, a detection light sensor 118 and a reference light sensor 120. The light source 122 provides incoherent and/or coherent light to the detection region 104 and the reference region 106. The detection light sensor 118 and reference light sensor 120 are configured to detect light associated with the detection region 104 and the reference region 106, respectively. For example, the detection light sensor 118 may be situated near a side of the detection region 104 opposite to the light source 122 and may detect light transmitted through the detection region 104 as illustrated in FIG. 22. The reference light sensor 120 may be similarly situated near a side of the reference region 106 opposite to the light source 122 and may detect light transmitted through the reference region 106. Other arrangements of the light source 122, the detection light sensor 118 and the reference light sensor 120 are possible, as described further herein below.

In this embodiment, the detection signal 122 produced by the detection light sensor 118 may be compared to the reference signal 124 produced by the reference light sensor 120 using a signal comparison device 126, such as an op amp or differential amplifier as illustrated in FIG. 22. The combined signal 128, which may be a difference between the detection signal 122 and the reference signal 124 may be compared to a predetermined calibration rule to determine the presence and/or concentration of the one or more analytes 110 within the sample 112.

In various embodiments, a system (not shown) associated with the device 100 may be used to control the operation of the device 100, to collect the one or more combined signals 128, to process the one or more combined signals 128 to detect and/or quantify the one or more analytes 110 in the sample 112, to determine one or more conditions of a subject, and/or communicate one or more results to the system user including, but not limited to the concentration or concentration ratios of the one or more analytes 110, and/or the one or more conditions of the subject. Various embodiments of the system are described in detail herein below.

In various other embodiments, the device may implement the multiplex detection of the one or more analytes 110 through the incorporation of two or more epitope binding agents 108 within the detection region 104, where each of the epitope binding agents is selected to bind exclusively to a single analyte 110 that is different from the analytes 110 bound by each of the other epitope binding agents 108. In another embodiment, the device and the balanced sensor detection methodology for an ELISA reaction may be used with a Complementary Metal Oxide Semiconductor (CMOS) chip device that is portable and rapid at reading the multiplexing response to each of the multiple target analytes either discreetly or in a group of targeted analytes to create a disease specific ratio.

(a) Surface for a Detection Reaction

In an embodiment, the device comprises a surface for a detection reaction. Such a surface should allow for the detection of a difference in light between a reference location and a location comprising the detection reaction. By way of non-limiting example, the surface may be glass, plastic, nitrocellulose, indium, tin, cadmium, silica, poly (ethylene glycol)methacrylate graft polymer, or variations thereof. The surface material may be selected to be compatible with the particular composition or type of sample to be analyzed. In addition, the surface material may be selected to be compatible with a particular detection reaction and/or sensor configuration. For example, a transparent material may be selected if the sensors are configured to detect light transmitted through each spot or region within which a detection reaction occurs. In another example, a material such as polysterine may be used as the surface to facilitate the immobilization of epitope binding agent within a region used to conduct the detection reaction. The surface may be formed as a well, a spot, a concavity, a space, a peak, or other formations that allow for the detection of a difference in light between a reference location and a location comprising a detection reaction.

Generally speaking a surface for a detection reaction will be designed to hold or support a bodily fluid sample. Suitable bodily fluid samples may comprise blood (including whole blood, plasma, serum, or a combination thereof), urine, sputum, tears, cerebral spinal fluid, lymph, saliva, sweat, or other bodily fluids. Methods of collecting bodily fluid samples are known in the art. Typically a bodily fluid sample should comprise a volume of about 0.2 microliters to about 100 microliters or more.

A surface for a detection reaction may also comprise a means for a detection reaction. Generally speaking, a means for a detection reaction comprises one or more epitope binding agents (i.e. analyte binding agents) and a means for producing a change in light. The change in light may be a decrease in detectable light or an increase in detectable light. In one embodiment, the change in light may be created by the formation of an insoluble product that does not transmit light, and therefore, results in a decrease in detectable light. For instance, the insoluble product may be an epitope binding agent/analyte complex, an epitope binding agent/analyte/tagged detection agent complex, or an epitope binding agent/analyte/detection agent/tag specific for the detection agent complex. In other embodiments, the change in light may be created by the formation of a product that produces light, resulting in an increase in detectable light. Suitable light changes may include chemiluminescent reactions and fluorescent reactions.

The term "epitope binding agent" refers to a substance that is capable of binding to an analyte. Suitable epitope binding agents may include an antibody (e.g. a polyclonal antibody, a monoclonal antibody, a single chain antibody, an antibody fragment, etc.), an aptamer, a double-stranded DNA sequence, a ligand and a fragment of a ligand, a receptor and a fragment of a receptor, a polynucleotide, a coenzyme, a coregulator, an allosteric molecule, or an ion. In an exemplary embodiment, an epitope binding agent is an antibody.

An epitope binding agent may be absorbed or otherwise bound to the surface for a detection reaction using means known in the art.

The term "detection agent" refers to a substance that is capable of binding to an analyte. Suitable detection agents are equivalent to epitope binding agents, with the exception that for a given analyte, an epitope binding agent and a detection agent will not bind to the same epitope of the analyte. In an exemplary embodiment, an epitope binding agent is an antibody. Generally speaking, a detection agent is not absorbed to a surface. The term "tagged detection agent" refers to a detection agent that comprises a detectable tag. As used herein, a detectable tag is one which causes a change in light, as described above. For instance, a detectable tag may be a colorimetric substance.

In some embodiments, more than one epitope binding agent is utilized. For instance, two epitope binding agents may be utilized for a single analyte. Generally speaking, if two epitope binding agents are utilized, each epitope binding agent should recognize a distinct epitope of the analyte. In exemplary embodiments, one or more antibodies are utilized as epitope binding agents.

An analyte, as used herein, refers to a substance in a bodily fluid sample that may be measured as an indication of the health/disease state of a subject. As used herein, "analyte" is equivalent to "biomarker." For instance, an analyte may be a protein (e.g. a chemokine, an antibody, or other protein), a carbohydrate or carbohydrate moiety (e.g. a sugar, a starch, or a proteoglycan), a lipid or lipid moiety, a nucleotide or nucleotide sequence, or other biomolecule. An analyte may be extracellular, or the bodily fluid sample may be treated so as to release an intracellular analyte using means known in the art. Alternatively, an analyte may be present on the surface of a cell in a bodily fluid sample. Such samples may be treated so as to release the analyte from the cell membrane or cell surface using means known in the art.

A device of the invention may be used to measure more than one analyte. In such instances, a surface for a detection reaction may comprise multiple epitope binding agents, with different epitope binding agents directed to different analytes. In some embodiments, more than one antibody pairs may be utilized, with each antibody pair specific for a particular analyte. In exemplary embodiments, a device may measure more than one analyte in a multiplex format. That is, all of the more than one analytes may be measured in a single well. In further exemplary embodiments, more than one analyte may be measured in a multiplexed microarray-style reaction. For instance, in various embodiments, 2, 3, 4, 5, 6, 7, 8, 9, 10, 11, 12, 13 or more than 13 analytes may be detected in a multiplex reaction. As used herein, multiplex means the analytes are detected simultaneously in a single bodily fluid sample, as opposed to individual analytes being detected in several different samples, or at different times with a single sample.

For instance, for a device embodiment that incorporates a CMOS sensor, a) multiple detection antibodies or pre spotted substrates may be included to bind with target analytes, or the concavity of each space of the CMOS chip may be used. The reference location or controls may occur within the same reaction location using the balanced differential method and may be accomplished by the recognition software. The signal difference between analytes in the CMOS maintains the ability to simultaneously identify discrete target analytes by comparing to controls.

In another example, using a device embodiment that incorporates a CMOS sensor (or perhaps another multiplexing well approach) there may be multiple (e.g. 2, 3, 4, 5, 6, 7, 8, 9, 10, 11, 12, 13, or more than 13) analytes situated in a CMOS concavity well detected together, hence multiplexing a microarray of proteins. Comparatively there may be another concavity of the CMOS containing the controls for each target analyte in this example. In another embodiment, each concavity of the CMOS image sensor may be used for a single analyte and within the target analyte well its control for the target in an immediately adjacent well.

In addition, a competitive ELISA methodology with a known concentration of control may be conducted in this example. During the reaction, each analyte's location in the detection region will be compared to corresponding controls within each control's location, with each location within the same environmental conditions. For instance, the comparison may be between the individual analyte in the detection region and a standard well containing the multiple controls.

Individual analytes within a well/location are differentiated by the standardized spot location of the microarray within that well/location. The spatial orientation of the analytes will produce a pattern recognized by the voltage read out. A system that includes analysis software may be used to analyze the pattern to determine the concentration of each analyte in the sample.

FIG. 28 is a top view of a surface 700 in one embodiment. The surface may include one or more regions 702 within which a detection reaction may occur. For example, the region 702 labeled "1" in FIG. 28 may contain reagents suitable for the detection reaction for a first analyte, the region 702 labeled "2" may contain reagents suitable for the detection reaction for a second analyte, and so on. In another embodiment, a subset of the regions 702 may be detection regions used to conduct detection reactions for the analytes, and another subset of the regions 702 may be reference regions corresponding to the detection regions and used to implement the balanced sensor detection methodology. For example, the region 702 labeled "1" may be a detection region for a first analyte and the region 702 labeled "9" may be a reference region corresponding to the region labeled 702 labeled "1". Similarly, the regions labeled "2" and "10" may be a detection region and corresponding reference region for a second analyte and so on.

The shape of the surface 700 and the spatial arrangement of the regions 702 may be any known shape and arrangement without limitation. Non-limiting examples of suitable surface shapes include circular, square, and rectangular. Non-limiting examples of suitable arrangements of the regions 702 include circular or annular, rows and columns, and linear.

In addition, the pattern of detection regions and corresponding reference regions may be any known pattern without limitation. In one embodiment, the detection region may be diametrically opposite to its corresponding reference region in a circular arrangement of regions 702 as illustrated in FIG. 28. In another embodiment, the detection region and reference region may be immediately adjacent to one another. For example, the regions 702 labeled "1" and "2" in FIG. 28 may be the detection and reference regions for a first analyte If a known amount of analyte is added to the reference region, then separate wells (or equivalent) are needed for the detection region and the reference region. If, however, the reference region comprises known analyte that is "pre-spotted" in the reference region, the reference region may be in the same well (or equivalent) as the detection region. Stated another way, in one well (or equivalent), a device of the invention may comprise an absorbed epitope binding agent specific for an analyte, and in the same well (but in a different location within the well), the device may further comprise a known amount of the analyte in question. This allows for the detection reaction and the reference region to be exposed to the same sample, and eliminates the need for dividing up a sample.

Referring back to FIG. 28, the surface 700 may further include a sample introduction port 704 for the introduction of the sample to the surface 700. The sample introduction port may be a hole or conduit as illustrated in FIG. 28. Alternatively, the sample introduction port 704 may be a region of the surface 700 upon which a drop of the sample is placed. In one embodiment, the sample may move from the sample introduction port 704 to the regions 702 by any known means. In one embodiment, the sample may diffuse radially outward across the surface toward the regions 702 by diffusion or capillary action. In another embodiment, the surface may include microfluidic channels 706 to convey the sample from the sample introduction port 704 to each region 702. In yet another embodiment, the surface 700 may further include a conditioning region 708 containing reagents used to form a fluid substrate from the sample that is suitable for conducting the multiplex detection reactions within the regions 702.

(b) Sensor

The device further comprises one or more sensors in various embodiments. Generally speaking, the one or more sensors are used to measure the difference in light transmitted through or reflected from spots or regions within which detections reactions for the analytes and corresponding controls are conducted. Typically, the one or more sensors are compatible with the utilization of a balanced sensor detection methodology to detect a light difference between groups of pixels monitoring the designated reaction locations on the surface for a detection reaction and each designated reaction location's corresponding reference location.

Any light sensing device may be used as a sensor in various embodiments of the device without limitation. In one embodiment, the sensor may be a CMOS image sensor. In another embodiment, the sensor may be a photodiode pair. In still other alternatives, the sensor may be any sensor known in the art to be able to image the low light difference between groups of pixels monitoring the designated reaction locations on the surface for a detection reaction and reference locations.

Figure 29A:
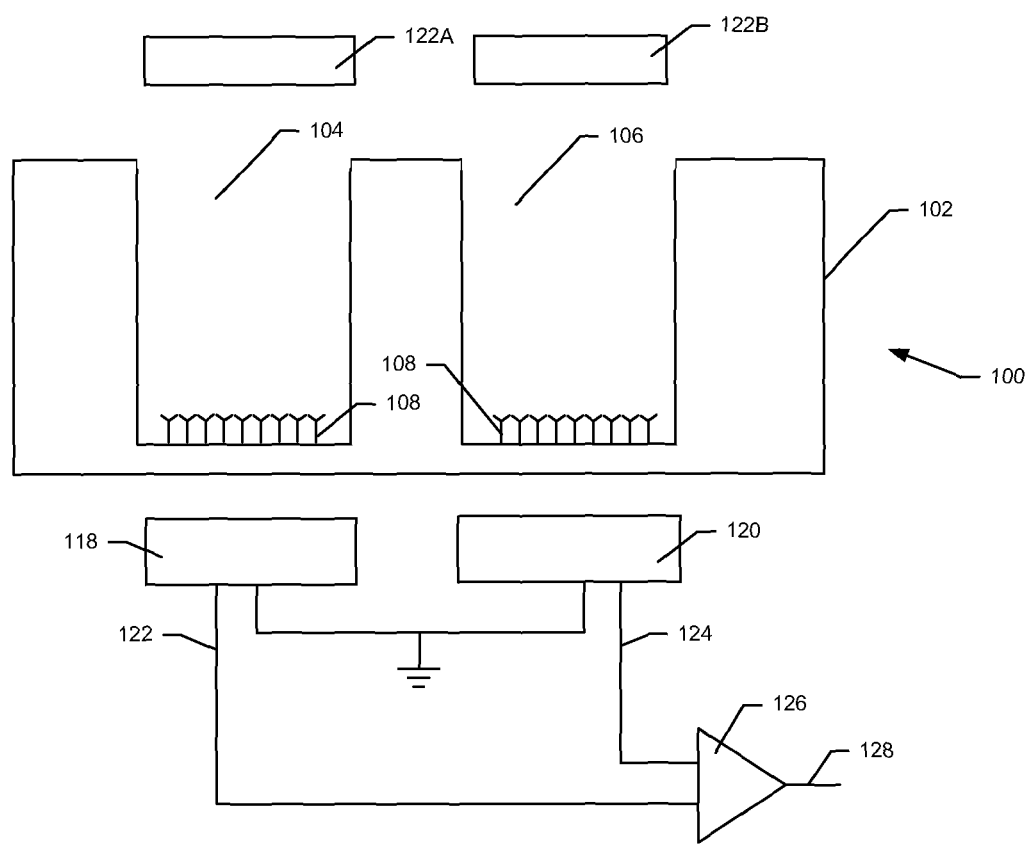

In various embodiments, the one or more sensors of the device may be used in a balanced detection method that is implemented by associated sensor circuitry and software included in a system associated with the operation of the device. Generally speaking, the "balanced detection method" is a method in which the difference between the signal generated from a reference location and a corresponding reaction location are set to zero as the initial condition (e.g. before addition of an analyte). For instance, when photodiodes are used, a photodiode pair may be configured as a "balanced detector" such that the currents from the photodiodes are subtracted and set to zero as the initial condition, as illustrated in FIG. 29A.

The balancing of the sensors may be performed in at least two ways in various embodiments. Referring back to FIG. 29A which illustrates one embodiment, a reference light source 122B such as an LED or laser diode light source may be dedicated to the reference region 106 and a separate detection light source 122A may be dedicated to the detection region 104. If there is no initial balancing, the intensity of light from each of the light sources 122A/122B may be adjusted such that detected light intensity measured by the detection light sensor 118 and the reference light sensor 120 are essentially equal to each other, resulting in equal readings 122 and 124 from the detection sensor 118 and the reference 120, respectively. In a second embodiment (not shown), the outputs of the one or more light sources are fixed at a preselected intensity and the balancing of the sensors is achieved by controlling the value of a variable resistor or other component of a control circuit associated with each sensor. In one embodiment, if the sensor is a CMOS imager, the one or more variable resistors associated with the pixels imaging the detection region 104 and/or the pixels imaging the reference region 106 may be adjusted to balance the sensors.

Figure 29B:
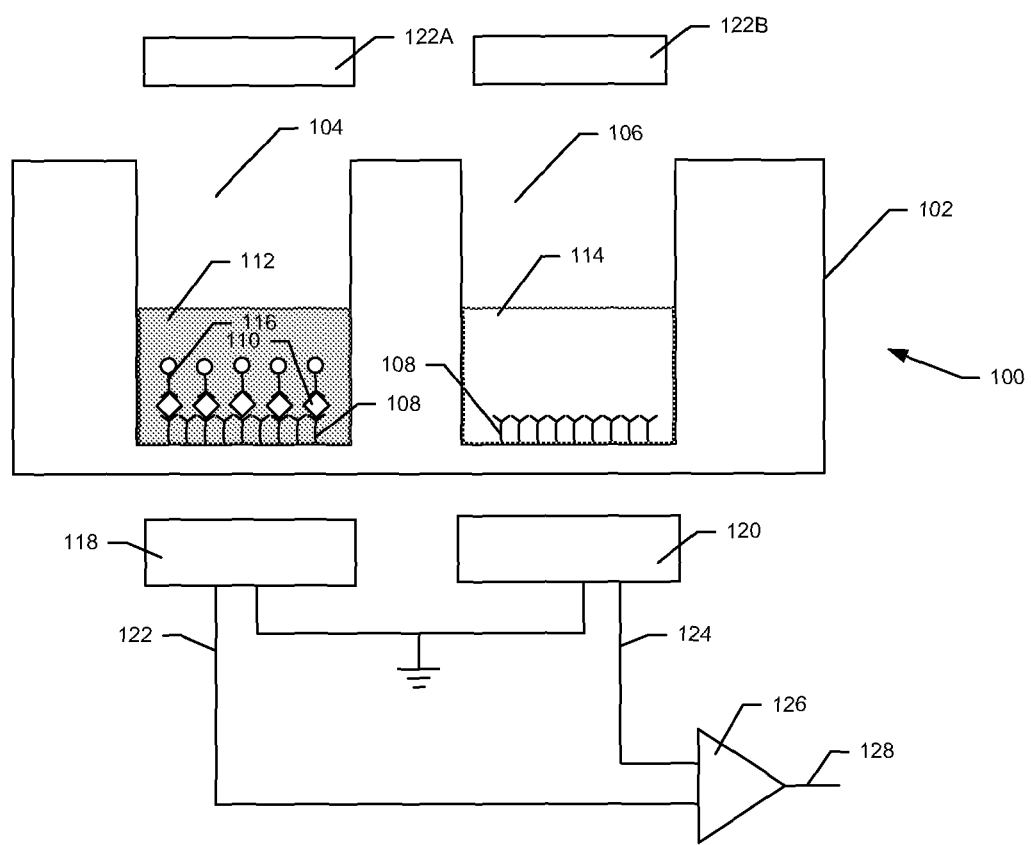

Referring to FIG. 29B, as the enzymatic reaction takes place within the detection region 104, the light captured by the detection sensor 118 may be altered by the products of the detection reaction. For example, the detection reaction may produce optically opaque precipitates that may decrease the intensity of light sensed by the detection sensor 118. The reference sensor 120 may continue to sense the same intensity of light because the conditions within the reference region 106 remain essentially unchanged during the detection reaction in the reaction region 104, and hence generates the same reading 124 as its initial reading. This difference in the reading 122 of the detection sensor 118 alters the initial "balance" of the sensors, resulting in a non-zero combined signal 128.

The change in the combined reading 128 may then be translated into an analyte concentration using a calibration curve. An illustrative example of an analyte calibration curve 900 is depicted in FIG. 30. In one embodiment, the calibration curve 900 may be developed by performing repeated measurements 902 using the device 100 illustrated in FIG. 29A and FIG. 29B for a plurality of samples containing known concentrations of analyte that vary through a calibration range. In one embodiment, the calibration curve may be used to convert the combined signal output encoding the differential in light detected by the one or more sensors into analyte concentration measurements within 0.01 picograms per milliliter of the target analyte concentrations.

In various embodiments, a CMOS sensor may be used to detect the light intensities of the one or more detection regions and reference regions of the device. In one embodiment, the CMOS sensor may obtain an image containing an array of pixels encoding a spatial map of the measured light intensity detected by the CMOS sensor. The CMOS sensor image may contain a plurality of subregions at different spatial locations throughout the image, in which each subregion corresponds to the light intensity measured from one of the detection regions or reference regions of the surface of the device. Each subregion may contain one or more pixels from the image; each pixel is associated with a spatial location and a pixel intensity encoding the measured light intensity at that spatial location. In an embodiment, the pixel intensities within each subregion may be classified as a detection region or reference region for a particular analyte based on the known spatial arrangement of the detection and reference regions on the surface of the device.

In various embodiments, the balancing of the pixel or pixel groups assigned for each biomarker/analyte can be performed in different ways. In one embodiment, the pixel or pixel groups of each biomarker/analyte may be balanced individually. In another embodiment, reference pixels from the reference region and detection pixels from the detection location may be chosen without regard to their association with any particular analyte and their difference signal may be used to balance the sensors. In this second embodiment, one need not balance the reaction and reference pixel(s) assigned to each biomarker/analyte to be detected.

In another example, when a CMOS sensor is used, for each biomarker/analyte pre-spotted in the microarray to be multiplexed and detected, there will be two groups of pixels each having an identical set of indices associated with each of the one or more analytes assigned. One of the pixel groups will monitor the reaction location whereas the other group will be used as a reference and will monitor a reference location in which no reaction takes place. As the initial condition, the difference of the intensities (e.g. pixel-by-pixel or average within a region of interest) detected by the two groups of pixels for each biomarker/analyte will be balanced to be as close to zero as possible, similar to the balanced detector built by a pair of photodiodes. The change in the difference of detected light intensities will be processed to output the information on the reaction taking place to be captured as a voltage difference. The voltage output is compared by the device and the voltage output is amplified to produce a set of combined signals associated with the concentrations of the one or more analytes.

The implementation of the balanced sensor methodology using the sensors of the device in various embodiments may enhance the sensitivity of the measurements of analyte concentrations in a wide variety of lighting conditions, including low light conditions such as ambient light. As a result, the sensitivity of the analyte concentration measurements may be maintained at suitable high levels regardless of lighting conditions. In one embodiment, the device may use ambient lighting as the light source, resulting in a device with relatively low energy requirements and enhanced portability.

(c) Light Source

In various embodiments, a light source illuminates the detection and reference regions. In one embodiment, ambient light or low level light may be used as the light source, thereby eliminating the need for the inclusion of a powered light source in the device. Alternatively, other coherent or incoherent light sources may be incorporated into the device for use as a light source. Non-limiting examples of suitable light sources include incandescent light sources, laser diodes, and light emitting diodes (LEDs).

The light source may be situated in any location relative to the one or more sensors of the device without limitation. In various embodiments, the light source may be situated on the same side of the surface of the device as the sensors, and the sensors are configured to detect light reflected from the detection and reference regions. In various other embodiments, the light source may be situated on an opposite side of the surface relative to the sensors, and the sensors are configured to measure light transmitted through the detection and reference regions.

FIG. 22 illustrates the arrangement of the light source 122 relative to the other components of the device 100 in one embodiment. In this embodiment, the light source 122 is situated above the substrate/tray 102 and the detection/reference sensors 118/120 are situated below the tray 102 in order to sense light transmitted through the detection region 104 and reference region 106. In another embodiment, the light source 122 of the device 100 illustrated in FIG. 22 may be omitted, and the sensors 118/120 may detect ambient light transmitted through the detection and reference regions 104 and 106.

(d) Other Device Characteristics

A device of the invention is intended to be portable. As such, the device should be lightweight, should be functional at ambient temperature, should produce a result in less than 40 min, preferably 30 min or less, should use a low energy source such as one or more batteries, and should function in ambient or low-level light.

II. Methods of Use

A detection method may use the detection device to measure one or more than one analyte in a sample. In an exemplary embodiment, a device of the invention may be used to measure an analyte or combination of analytes detailed in section III below. The detection method may include, but is not limited to, a modified ELISA method and multiplexing the detection of analytes. The modified ELISA may include a combination solution containing a bodily fluid sample, tagged detection agent, and any other reagents necessary for the modified ELISA method. The combination solution may include multiple tagged detection agents for multiple analytes within the bodily fluid sample.

The multiplexed detection of analytes may be used to make a disease determination based on the signal from the device. The measurements obtained using a detection device may be utilized to make treatment decisions about the subject from the provided bodily fluid sample. For example, see Table C below.

(a) Modified ELISA Method

In one embodiment, the detection reaction is a modified ELISA. Generally speaking, an ELISA includes coating a substrate with a capture antibody specific for the analyte, immobilizing the analyte by adding the sample, adding a detection antibody to form a complex with the analyte, and detecting the complex through a secondary antibody linked to an enzyme. Between each step, the substrate is washed with a mild detergent to remove any proteins or antibodies that are not specifically bound. The washing step may need to be repeated several times to ensure all excess antibodies and proteins are removed. An enzymatic substrate is then added, which will produce a visible signal which correlates to the concentration of the analyte in that sample. The signal from the sample may be compared to a known standard ladder to determine the concentration. A typical ELISA may take between 5 and 24 hours to complete because of the incubation times for each of the steps along with the washing steps between each incubation step.

Alternatively, a detection reaction of the present invention may include a modified ELISA method. A modified ELISA method may include combining a bodily fluid sample that comprises one or more analytes, tagged detection agents (or detection antibodies and indicator reagents) in one combined solution and incubating together. In an aspect, the substrate may be pre-treated with one or more epitope binding agents (capture antibodies) prior to the addition of the combined solution.

The epitope binding agent and the detection agent used in the modified ELISA method may be antibodies. In an aspect, the epitope binding agent may be a monoclonal antibody. In another aspect, the tagged detection agent may be a monoclonal antibody. An advantage of using monoclonal antibodies is that the reagents may be mixed together, washed and put on the substrate at the same time, hence reducing the time of the detection reaction. In an aspect, more than one monoclonal antibody may be used in the modified ELISA method to detect more than one analyte in the bodily fluid sample.

In some embodiments, a monoclonal antibody epitope binding agent and a monoclonal antibody detection agent may be co-incubated with the sample. The combination of the sample, and detection agent or tagged detection agent and indicator reagents may decrease standard ELISA steps by eliminating separate incubation times and eliminating the washing steps in between. In addition the reduction in reaction times, the modified ELISA method may be enhanced by the selection and modification of reagents in progress.

The ELISA standard methodology was modified to using the balance detection scheme, taking about 30 minutes instead of the typical 5 hours to 24 hours. For instance, the modified ELISA method using individual monoclonal antibodies may provide accurate result within about 10, 15, 20, 25, 30, 35, 40, 45, 50, 55, 60, 65, 70, 75, 80, 85, 90, 95 or 100 minutes of the introduction of the analyte to the antibody. This aspect of the monoclonal antibody detection method may measure a combination of target analytes and may be adapted to a portable CMOS image sensor with balanced detection methodology. In a preferred embodiment, a device of the invention may provide an accurate result in less than 35 min after the introduction of the analyte to the epitope binding agent.

In an aspect, a modified ELISA method staining procedure (BCIP/NBT) may be detected using the balanced detection system with ambient light. The insoluble substrate may allow for real time monitoring of different biomarkers in individual microarray spots without stopping development of the substrate.

In a further aspect, a device of the invention measures the change in light from the epitope binding agent/analyte/detection agent complex alone, without the use of a colorimetric substance.

Once in the detection region, the shortened ELISA reaction may be used to reduce the time needed to detect the concentration of the target analytes. Multiple analytes in the bodily fluid may be exposed to chambers within the device. The reaction may modify the analytes in the sample to enable light detection to be reported. In an aspect, the simplified detection method may meet the specifications for a CMOS image sensor multiplexing device.

(b) Multiplexed Detection of Analytes

The combined solution may be used to detect multiple analytes within one sample. As described above, one combined solution containing a sample with analytes, multiple different tagged or untagged detection agents, and/or indicator reagents may be placed on the device. The modified ELISA method along with the multiplexing of antibodies may allow for a relatively quick method of detecting multiple analytes in a single sample.

The epitope binding agents and/or tagged detection agents may be monoclonal antibodies in an embodiment. This may allow for specific binding to the analyte without significant cross-reaction. The use of monoclonal antibodies allows for specific binding of each analyte to its specific monoclonal capture and/or detection antibody (epitope binging agent and/or tagged detection agent). Separate solutions each containing different detection agents for each analyte desired to be detected do not have to be applied, which reduces the assay time and simplifies the process.

Multiplexing of novel and unique antibody pairs with minimal cross reactivity may be used to uniquely identify each target analyte. A combined solution containing multiple antibodies may be placed in a reaction well substrate. In an aspect, the combined solution may contain more than one antibody ranging from about 2 to about 20 antibodies. In another aspect, the solution may contain more than one antibody ranging from about 2 to about 6 antibodies, from about 4 to about 8 antibodies, from about 6 to about 10 antibodies, from about 8 to about 12 antibodies, from about 10 to about 14 antibodies, and from about 12 to about 16 antibodies, from about 14 to about 18 antibodies, from about 16 to about 20 antibodies. In one aspect, the solution may contain at least 13 combined antibodies.

In one aspect, coated glass may be used as the substrate. The glass slide may then be read using a standard ELISA microscope, an Elisa plate reader, or image processed microscope photographs.

The balanced detection method was verified to be adaptable to the standard ELISA assay for the adaption of multiplexing of the antibody pairs.

Selected and tested monoclonal antibody pairs may be used for target analytes in the portable detection system. Specifically in an embodiment of the device five target analytes CCL3, CCL5, CCL18, hsCRP and cardiac TnI were tested repetitively to identify the ideal combination of antibody pairs able to detect individually each specific target analyte in a reaction chamber without cross reacting with the other pairs of monoclonal antibodies. The sensitivity measured was consistent with the need to report levels within normal limits for a human to have the range to detect elevated levels of the specific antibodies.

In other embodiments, each of the analytes in Table A below are detectable using a device of the invention. Specifically, in an exemplary embodiment, the device comprises a single well (or equivalent) that comprises at least one epitope binding agent specific for each analyte listed in Table A. The analytes of Table A are then detected using detection agents included in the combined solution. In these embodiments, the reference region may be located in the same well as the detection region, or in a separate well. In still other embodiments, a device of the invention is used to detect at least 3, 4, 5, 6, 7, 8, 9, 10, 11, 12 or 13 of the analytes listed in Table A. In particular embodiment, a device of the invention may be used to detect a combination of analytes indicated in Tables B or C.

The combined signal from the multiple analytes may then be compared to a standard through differential comparison described herein above. The result may then be used to develop a disease specific ratio and provide a response to the doctor or patient.

In another aspect, due to the unique aspect of using the balanced comparator with an optically opaque (BCIP/NBT) substrate, individual standard and reference pairs for each analyte can be monitored in real time as the locations develop their opacity. This allows individual analytes to be measured independently as they develop and eliminates the need for all analytes to be read simultaneously.

(c) Detecting Analytes in Sample

The detection method may include introducing a sample onto the detection device, adding the combined solution, and obtaining readings from the detection device. Before introduction of the sample, the substrate of the detection device may be pre-treated with epitope binding agents. The epitope binding agents may be specific for the target analytes that are desired to be detected.

The bodily fluid sample may be introduced into the reaction chamber or substrate. The introduction mechanism may result from a finger prick of blood, capture of sputum, or any other capture of other bodily fluids. The bodily fluid sample may be introduced to enzymes, buffers, and/or reagents to enable an enzymatic reaction. The bodily fluid may be introduced using an external pipetting method in one aspect.

The bodily fluid sample may be combined with multiple tagged detection agents and any other desired reagents for the modified ELISA method. Once in the reaction chamber, the modified ELISA method may be used to reduce the time needed to detect the concentration of the target analytes. Multiple analytes in the bodily fluid sample may be exposed to chambers within the device.

The reaction may modify the analytes in the bodily fluid sample to enable a light detection to be reported. The signal may then be detected by the device. The simplified protocol may meet the specifications for the CMOS image sensor multiplexing device. In an aspect, the device may report the condition of the patient based on the levels of each analyte detected.

In various embodiments, the device may use a balanced sensor detection methodology to detect and/or quantify the one or more analytes using the difference in readings measured from one or more pairs of light sensors: a first light sensor situated near an analyte detection region and a second light sensor situated near a control or standard region. The balanced sensor detection methodology enhances the sensitivity of the device, providing the ability to detect the one or more analytes under a variety of lighting conditions including, but not limited to, low light or ambient light conditions. A comparator over/under evaluation can report one comparator pair at a time as a substrate develops and precipitates on an appropriate spot.

In another embodiment of the invention the CMOS image sensor can scan a series of over/under reactions to produce an array of results that are then converted to a voltage output converted to a specific measure of each unknown or target analyte intended to be measured.

III. Specific Biomarker/Analyte Combinations

It has been discovered that a panel of biomarkers may be used to predict a cardiac failure and/or wound closure, to name a few applications of the present device. In particular, a detection method may be used to predict an imminent cardiac failure in a subject even when other methods of diagnosis fail to indicate a cardiac failure. Advantageously, the detection method of the invention may predict an imminent cardiac failure within about 180 days. In exemplary embodiments, a method of the invention may predict an imminent cardiac failure within about 72 hours to 2 weeks after the method is employed. Alternatively, a detection method may be used to determine the course and/or stage of wound healing in a subject. Generally speaking, the method comprises, in part, determining the level of biomarkers in a biological sample taken from the subject. Components of the method and biomarkers are described in more detail below.

(a) Subject

For the purposes of the aspects and embodiments of the invention, the subject may be a human or any other animal. In particular embodiments, the subject is selected from the group consisting of primate, equine, bovine, ovine, caprine, leporine, avian, feline, rodent, or canine. In one embodiment, the subject is a rodent. Examples of rodents include mice, rats, and guinea pigs. In another embodiment, the subject is a primate. Examples of primates include monkeys, apes, and humans. In an exemplary embodiment, the subject is a human.

In some embodiments, the subject may be complaining of discomfort that may indicate or be suggestive of cardiac failure. Non-limiting examples of discomfort that may indicate cardiac failure may include chest pain or pressure, a strange feeling in the chest, sweating, shortness of breath, nausea or vomiting, pain, pressure, or a strange feeling in the back, neck, jaw, or upper belly, or in one or both shoulders or arms, lightheadedness or sudden weakness, heaviness or weakness of the lower extremities, or a fast or irregular heartbeat. One of skill in the art will recognize that such examples of discomfort can and most likely will vary from subject to subject, and from male to female.

In other embodiments, a subject may have an open wound. Generally speaking, the classic model of wound healing is divided into three or four sequential, yet overlapping, phases: (1) hemostasis (not considered a phase by some authors), (2) inflammatory, (3) proliferative and (4) remodeling. A suitable subject of the invention may have a wound in any of these four stages. A subject may have a wound that is progressing through the healing process, or may have a wound that is not progressing (e.g. not healing).

(b) Biological Sample

The level of biomarkers is determined in a biological sample taken from the subject. A biological sample, as defined herein, may be an amount of bodily fluid taken from a subject. Non-limiting examples of bodily fluids may include plasma, serum, whole blood, cerebrospinal fluid (CSF), synovial fluid, tissue fluid, organ fluid, such as bile, semen and the like, humors, such as vitreous humor, lavage fluids, such as nasal lavage fluid and bronchioalveolar lavage fluid, secretions, such as mucinous fluids, exudates, saliva, perspiration and tears, waste products, and other biological fluids in the case of non-human animals. In an exemplary embodiment, the biological sample is blood.

In one embodiment, the biological sample is selected from the group comprising whole blood, serum, and plasma. In an additional embodiment, the biological sample is whole blood. In another embodiment, the biological sample is serum. In yet another embodiment, the biological sample is plasma. In a further embodiment, the biological sample is human serum. In an exemplary embodiment, the biological sample is human whole blood.

The method of collecting a bodily fluid from a subject can and will vary depending upon the nature of the bodily fluid. Any of a variety of methods generally known in the art may be utilized to collect a bodily fluid from a subject. The bodily fluids of the test sample may be taken from a subject using any known device or method. Non-limiting examples of devices or methods suitable for taking bodily fluid from a mammal include urine sample cups, urethral catheters, swabs, hypodermic needles, thin needle biopsies, hollow needle biopsies, punch biopsies, metabolic cages, and aspiration. In preferred embodiments, the bodily fluid collected is blood. Methods for collecting blood or fractions thereof are well known in the art. For example, see U.S. Pat. No. 5,286,262, which is hereby incorporated by reference in its entirety. Generally speaking, irrespective of the method used to collect a bodily fluid, the method preferably maintains the integrity of the biomarkers such that they can be accurately quantified in the bodily fluid.

(c) Biomarkers/Analytes

One embodiment of the invention measures the level of a biomarker within a biological sample. As used herein, "level of a biomarker" refers to the amount of RNA coding for the biomarker/analyte present in a sample, the rate of transcription of a biomarker, the amount of biomarker protein in a sample, the rate of protein synthesis, or the level of enzymatic activity of a biomarker.

Suitable biomarkers include but are not limited to CCL2, CCL3, CCL11, CCL17, CCL18, CCL22, CCL5, troponin, hs-Troponin, troponin skeletal isoforms, cystatin C, IL-1 alpha, IL-1 beta, IL-6, IL-7 IL-8, IL-10, IL-12p70, IL-13, IL-18, TNF/TNFalpha, MMP9, MMP2, MMP3, CK-MB, GDF-15, H-FABP/FABP3, hs-CRP, LpPLA2, MPO, Myoglobin, NT-proBNP, pregnancy-associated plasma protein-A (PAPP-A), soluble FAS, TIMP-1, IL-33, IL-34, IL-23, IL-17, CXCR4/CXCL12 (SDF-1), CX3CL1, CXCL2, CXCL8, CXCL9, CXCL10 (IP-10), CXCL16, CCL25, Heat shock protein 27 (HSP27, CCR 9, sCD40L, chemokine-like factor MIF (macrophage migration inhibitory factor), OSM (oncostatin M), interferons, osteoprotegerin (OPG), sRANKL (soluble receptor activator of nuclear factor-KB ligand), sVCAM (soluble vascular cell adhesion molecule), sICAM (soluble intercellular adhesion molecule), Beta-catenin (or β-catenin) is a protein that in humans is encoded by the CTNNB1 gene, VEGF, CSF2/GM-CSF, Myc (c-Myc) is a regulator gene that codes for a transcription factor, Semaphorin-4D (SEMA4D) also known as Cluster of Differentiation 100 (CD100), is a protein of the semaphorin family that in humans is encoded by the SEMA4D gene, and Placental Growth Factor (PIGF). In some embodiments, a biomarker may encompass a cell and/or tissue producing, secreting, synthesizing, or expressing a marker listed above. In an alternative embodiment, a biomarker may encompass a circulating endothelial cell (CEC). Three chemokine biomarkers, CCL3, CCL5, and CCL18, are complementary as they likely cover different processes of the inflammation, epithelialization, and tissue remodeling processes yet there is no cross reactivity with antibodies. These biomarkers and others that may be used in the detection method are further described below.

The CCL3 biomarker is the chemokine (C-C motif) ligand 3 (CCL3) protein, also known as Macrophage inflammatory protein-1α (MIP-1α). CCL3 is a cytokine belonging to the CC chemokine family that is involved in the acute inflammatory state in the recruitment and activation of polymorphonuclear leukocytes.

The CCL18 biomarker is the chemokine (C-C motif) ligand 18 cytokine belonging to the CC chemokine family. It was previously called PARC (pulmonary and activation-regulated chemokine).

The CCL5 biomarker is the chemokine (C-C motif) ligand 5. It is also known as RANTES (Regulated upon Activation, Normal T-cell Expressed, and Secreted).

Troponin is a complex of three regulatory proteins (troponin C, troponin I and troponin T) that is integral to muscle contraction in skeletal and cardiac muscle, but not smooth muscle. In some embodiments, the troponin biomarker in troponin C. In other embodiments, the troponin biomarker in troponin I. In yet other embodiments, the troponin biomarker in troponin T. In other embodiments, the troponin biomarker is the troponin complex comprising troponin C, I and T. The Cardiac troponin (hs cTnI) biomarker may be associated with myocardial infarction and a high concentration of this protein may be evidence of a myocardial infarction.

NT-proBNP, 76 amino acid N-terminal fragment of brain natriuretic peptide (BNP), is a secreted protein which functions as a cardiac hormone. The protein undergoes two cleavage events, one within the cell and a second after secretion into the blood. As used herein, the term "NT-proBNP" refers to full length NT-proBNP protein or any cleavage product or products of the protein. The protein's biological actions include natriuresis, diuresis, vasorelaxation, inhibition of renin and aldosterone secretion, and a key role in cardiovascular homeostasis. A high concentration of this protein in the bloodstream is indicative of asymptomatic or symptomatic heart failure. The Entrez Gene ID number for brain natriuretic peptide is provided in Table 1. From this, the nucleotide and amino acid sequence of NT-proBNP can be determined.

The HFABP (Heart-type Fatty Acid-Binding Protein) biomarker is a protein which is released from cardiomyocytes after an ischemic episode. The protein is involved in fatty acid metabolism for oxidation. A high concentration of this protein is indicative of worsening heart function and can be detected one to three hours after the pain of a myocardial infarction.

The PAPPA (Pregnancy-associated Plasma Protein A) is a protein associated with pregnancy and low plasma levels may be associated with Down syndrome.

The C-reactive protein (CRP) biomarker is a protein which increases in the blood in response to inflammation. A high-sensitivity CRP test can measure low levels of CRP. A high concentration of this protein in the blood may be indicative of worsening coronary artery disease and may be associated with an increased likelihood to develop stroke, myocardial infarction, or severe peripheral vascular disease.

The Placental growth factor (PIGF) biomarker is a protein involved with angiogenesis, particularly during pregnancy, and is part of the VEGF family. Low concentrations of PIGF can be associated with preeclampsia.

The Interferon gamma-induced protein 10 (IP-10), also known as C-X-C motif chemokine 10 (CXCL10) biomarker is a chemokine secreted in response to interferon. IP-10 has been associated with several roles including chemoattraction for monocytes/macrophages and angiogenesis.

The macrophage inhibitory cytokine 1 (MIC-1) biomarker is an autocrine regulatory molecule in macrophages. A high concentration of this protein may provide additive predictive value of a myocardial infarction.

The Cystatin C, or cystatin 3, biomarker is a protein which is associated with kidney function. A high concentration of this protein may be associated with myocardial infarction, stroke, and heart failure.

The lipoprotein-associated phospholipase A2 (LP PLA2), which may also be known as platelet-activating factor acetylhydrolase (PAF-AH), biomarker is an enzyme that is associated with low-density protein and is involved with atherosclerosis development. A high concentration of this protein may add to plaque instability measures.

Matrix metalloproteinase-1 (MMP-1) also known as interstitial collagenase and fibroblast collagenase is an enzyme that in humans is encoded by the MMP1 gene. The gene is part of a cluster of MMP genes which localize to chromosome 11 q22.3. MMP-1 was the first vertebrate collagenase both purified to homogeneity as a protein, and cloned as a cDNA.

Interleukin 8 (IL-8) is a chemokine produced by macrophages and other cell types such as epithelial cells. It is also synthesized by endothelial cells, which store IL-8 in their storage vesicles, the Weibel-Palade bodies. In humans, the interleukin-8 protein is encoded by the IL8 gene.

TIMP metallopeptidase inhibitor 1, also known as TIMP1, a tissue inhibitor of metalloproteinases, is a glycoprotein that is expressed from the several tissues.

Entrez Gene ID numbers for many of these biomarkers may be found in Table 1.

In an aspect, the level of biomarkers selected from the group consisting of CCL3, CCL5, CCL18, HFABP, PaPPa, hsCRP, hs cTnI, PIGF, Nt-proBNP, IP-10, MIC-1, cystatin C, LP PLA2, and any combination thereof may be measured. In another aspect, biomarkers IL-8, MMP1, and TIMP1 may be added to the panel of biomarkers to be measured. Table A lists concentrations of the biomarkers as a lower range where the biomarker may be ruled out and an upper (positive) range where the biomarker may be associated with myocardial infarction, worsening heart function, or any other predictive or prognostic event.

TABLE A

| Multiplex Marker | Lower range | Positive range |
|---|---|---|
| MIP 1 alpha (CCL3) | 8 pg/ml | 17.2-42.2 pg/ml |
| RANTES (CCL5) | 10 ng/ml | 14.2 ng/ml-55 ng/ml |
| CCL18 | 10 ng/ml | 43.3-110 ng/ml |
| HFABP | 1.0 µg/l | >6.25 ug/l |
| PaPPa | 5.0 µIU/ml | >6.0 µIU/ml to 50 |
| hsCRP | 1 mg/ml | 1.89-20 mg/L |
| hs cTnI | 20 pg/ml | >.03 ng/nl 100 ng/ml |
| PlGF Placental Growth Factor | 10 ng/l | >7.5 pg/mL->25 pg/mL |
| Nt-proBNP | 20 pg/ml | 305-5549 pg/mL |
| IP-10 | 150 pg/ml | 65-140 pg/ml |
| MIC-1 | 800 ng/l | >1000 ng/L-2200 ng/l |
| cystatin C | 0.3 mg/l | >0.3 mg/l-4.0 mg/l |
| LP PLA2 | 100 ng/ml | >400 ng/ml |

In some embodiments, the level of troponin and one, two, three, or four biomarkers selected from the group consisting of CCL3, CCL18, CCL5 and NT-proBNP may be measured. Table B lists preferred combinations of biomarkers that may be measured. In certain embodiments, one, two, three, four, five, six, seven, eight, nine, ten, or more than ten additional biomarkers may be used in conjunction with a combination listed in Table B.

TABLE B

| | | | |
|---|---|---|---|
| CCL3, CCL18, CCL5 | troponin | | |
| CCL3, CCL18, CCL5 | Cystatin C | | |
| CCL3, CCL18, CCL5 | H-FABP/FABP3 | | |
| CCL3, CCL18, CCL7 | IL-8 | | |
| CCL3, CCL18, CCL8 | IL-10 | | |
| CCL3, CCL18, CCL9 | IL-12p70 | | |
| CCL3, CCL18, CCL10 | IL-18 | | |
| CCL3, CCL18, CCL11 | CCL2/MCP1 | | |
| CCL3, CCL18, CCL12 | TNF/TNFalpha | | |
| CCL3, CCL18, CCL13 | MMP9 | | |
| CCL3, CCL18, CCL14 | CK-MB | | |
| CCL3, CCL18, CCL15 | GDF-15 | | |
| CCL3, CCL18, CCL16 | H-FABP/FABP3 | | |
| CCL3, CCL18, CCL17 | hs-CRP | | |
| CCL3, CCL18, CCL18 | LpPLA2 | | |
| CCL3, CCL18, CCL19 | MPO | | |
| CCL3, CCL18, CCL20 | myoglobin | | |
| CCL3, CCL18, CCL21 | NT-proBNP | | |
| CCL3, CCL18, CCL22 | PAPP-A | | |
| CCL3, CCL18, CCL23 | soluble FAS | | |
| CCL3, CCL18, CCL24 | TIMP-1 | | |
| CCL3, CCL18, CCL25 | IL-34 | | |
| CCL3, CCL18, CCL26 | IL-23 | | |
| CCL3, CCL18, CCL27 | IL-17 | | |
| CCL3, CCL18, CCL28 | CXCR4/CXCL12 (SDF-1) | | |
| CCL3, CCL18, CCL29 | CXCL16 | | |
| CCL3, CCL18, CCL30 | CCL25 TEC | | |
| CCL3, CCL18, CCL31 | CCR9 | | |
| CCL3, CCL18, CCL33 | sCD40L | | |
| CCL3, CCL18, CCL34 | PlGF | | |
| CCL3, CCL18, CCL5 | troponin | IL-6 | |
| CCL3, CCL18, CCL6 | troponin | IL-8 | |
| CCL3, CCL18, CCL7 | troponin | IL-10 | |
| CCL3, CCL18, CCL8 | troponin | IL-12p70 | |
| CCL3, CCL18, CCL9 | troponin | IL-18 | |
| CCL3, CCL18, CCL10 | troponin | CCL2/MCP1 | |
| CCL3, CCL18, CCL11 | troponin | TNF/TNFalpha | |
| CCL3, CCL18, CCL12 | troponin | MMP9 | |
| CCL3, CCL18, CCL13 | troponin | CK-MB | |
| CCL3, CCL18, CCL14 | troponin | GDF-15 | |
| CCL3, CCL18, CCL15 | troponin | H-FABP/FABP3 | |
| CCL3, CCL18, CCL16 | troponin | hs-CRP | |
| CCL3, CCL18, CCL17 | troponin | LpPLA2 | |
| CCL3, CCL18, CCL18 | troponin | MPO | |
| CCL3, CCL18, CCL19 | troponin | myoglobin | |
| CCL3, CCL18, CCL20 | troponin | NT-proBNP | |
| CCL3, CCL18, CCL21 | troponin | PAPP-A | |
| CCL3, CCL18, CCL22 | troponin | soluble FAS | |
| CCL3, CCL18, CCL23 | troponin | TIMP-1 | |
| CCL3, CCL18, CCL24 | troponin | IL-34 | |
| CCL3, CCL18, CCL25 | troponin | IL-23 | |
| CCL3, CCL18, CCL26 | troponin | IL-17 | |
| CCL3, CCL18, CCL27 | troponin | CXCR4/CXCL12 (SDF-1) | |
| CCL3, CCL18, CCL28 | troponin | CXCL16 | |
| CCL3, CCL18, CCL29 | troponin | CCL25 TEC | |
| CCL3, CCL18, CCL30 | troponin | CCR9 | |
| CCL3, CCL18, CCL31 | troponin | | |
| CCL3, CCL18, CCL32 | troponin | sCD40L | |
| CCL3, CCL18, CCL33 | troponin | PlGF | |
| CCL3, CCL18, CCL5 | IL-6 | IL-8 | |
| CCL3, CCL18, CCL6 | IL-6 | IL-10 | |
| CCL3, CCL18, CCL7 | IL-6 | IL-12p70 | |
| CCL3, CCL18, CCL8 | IL-6 | IL-18 | |
| CCL3, CCL18, CCL9 | IL-6 | CCL2/MCP1 | |
| CCL3, CCL18, CCL10 | IL-6 | TNF/TNFalpha | |
| CCL3, CCL18, CCL11 | IL-6 | MMP9 | |
| CCL3, CCL18, CCL12 | IL-6 | CK-MB | |
| CCL3, CCL18, CCL13 | IL-6 | GDF-15 | |
| CCL3, CCL18, CCL14 | IL-6 | H-FABP/FABP3 | |
| CCL3, CCL18, CCL15 | IL-6 | hs-CRP | |
| CCL3, CCL18, CCL16 | IL-6 | LpPLA2 | |
| CCL3, CCL18, CCL17 | IL-6 | MPO | |
| CCL3, CCL18, CCL18 | IL-6 | myoglobin | |
| CCL3, CCL18, CCL19 | IL-6 | NT-proBNP | |
| CCL3, CCL18, CCL20 | IL-6 | PAPP-A | |
| CCL3, CCL18, CCL21 | IL-6 | soluble FAS | |
| CCL3, CCL18, CCL22 | IL-6 | TIMP-1 | |
| CCL3, CCL18, CCL23 | IL-6 | IL-34 | |
| CCL3, CCL18, CCL24 | IL-6 | IL-23 | |
| CCL3, CCL18, CCL25 | IL-6 | IL-17 | |
| CCL3, CCL18, CCL26 | IL-6 | CXCR4/CXCL12 (SDF-1) | |
| CCL3, CCL18, CCL27 | IL-6 | CXCL16 | |
| CCL3, CCL18, CCL28 | IL-6 | CCL25 TEC | |
| CCL3, CCL18, CCL29 | IL-6 | CCR9 | |
| CCL3, CCL18, CCL30 | IL-6 | | |
| CCL3, CCL18, CCL31 | IL-6 | sCD40L | |
| CCL3, CCL18, CCL5 | IL-8 | IL-10 | |
| CCL3, CCL18, CCL6 | IL-8 | IL-12p70 | |
| CCL3, CCL18, CCL7 | IL-8 | IL-18 | |
| CCL3, CCL18, CCL8 | IL-8 | CCL2/MCP1 | |
| CCL3, CCL18, CCL9 | IL-8 | TNF/TNFalpha | |
| CCL3, CCL18, CCL10 | IL-8 | MMP9 | |
| CCL3, CCL18, CCL11 | IL-8 | CK-MB | |
| CCL3, CCL18, CCL12 | IL-8 | GDF-15 | |
| CCL3, CCL18, CCL13 | IL-8 | H-FABP/FABP3 | |
| CCL3, CCL18, CCL14 | IL-8 | hs-CRP | |
| CCL3, CCL18, CCL15 | IL-8 | LpPLA2 | |
| CCL3, CCL18, CCL16 | IL-8 | MPO | |
| CCL3, CCL18, CCL17 | IL-8 | myoglobin | |
| CCL3, CCL18, CCL18 | IL-8 | NT-proBNP | |
| CCL3, CCL18, CCL19 | IL-8 | PAPP-A | |
| CCL3, CCL18, CCL20 | IL-8 | soluble FAS | |
| CCL3, CCL18, CCL21 | IL-8 | TIMP-1 | |
| CCL3, CCL18, CCL22 | IL-8 | IL-34 | |
| CCL3, CCL18, CCL23 | IL-8 | IL-23 | |
| CCL3, CCL18, CCL24 | IL-8 | IL-17 | |
| CCL3, CCL18, CCL25 | IL-8 | CXCR4/CXCL12 (SDF-1) | |
| CCL3, CCL18, CCL26 | IL-8 | CXCL16 | |
| CCL3, CCL18, CCL27 | IL-8 | CCL25 TEC | |
| CCL3, CCL18, CCL28 | IL-8 | CCR9 | |
| CCL3, CCL18, CCL29 | IL-8 | | |
| CCL3, CCL18, CCL30 | IL-8 | sCD40L | |
| CCL3, CCL18, CCL5 | IL-10 | IL-12p70 | |
| CCL3, CCL18, CCL6 | IL-10 | IL-18 | |
| CCL3, CCL18, CCL7 | IL-10 | CCL2/MCP1 | |
| CCL3, CCL18, CCL8 | IL-10 | TNF/TNFalpha | |
| CCL3, CCL18, CCL9 | IL-10 | MMP9 | |

TABLE B-continued

| | | |
|---|---|---|
| CCL3, CCL18, CCL10 | IL-10 | CK-MB |
| CCL3, CCL18, CCL11 | IL-10 | GDF-15 |
| CCL3, CCL18, CCL12 | IL-10 | H-FABP/FABP3 |
| CCL3, CCL18, CCL13 | IL-10 | hs-CRP |
| CCL3, CCL18, CCL14 | IL-10 | LpPLA2 |
| CCL3, CCL18, CCL15 | IL-10 | MPO |
| CCL3, CCL18, CCL16 | IL-10 | myoglobin |
| CCL3, CCL18, CCL17 | IL-10 | NT-proBNP |
| CCL3, CCL18, CCL18 | IL-10 | PAPP-A |
| CCL3, CCL18, CCL19 | IL-10 | soluble FAS |
| CCL3, CCL18, CCL20 | IL-10 | TIMP-1 |
| CCL3, CCL18, CCL21 | IL-10 | IL-34 |
| CCL3, CCL18, CCL22 | IL-10 | IL-23 |
| CCL3, CCL18, CCL23 | IL-10 | IL-17 |
| CCL3, CCL18, CCL24 | IL-10 | CXCR4/CXCL12 (SDF-1) |
| CCL3, CCL18, CCL25 | IL-10 | CXCL16 |
| CCL3, CCL18, CCL26 | IL-10 | CCL25 TEC |
| CCL3, CCL18, CCL27 | IL-10 | CCR9 |
| CCL3, CCL18, CCL28 | IL-10 | |
| CCL3, CCL18, CCL29 | IL-10 | sCD40L |
| CCL3, CCL18, CCL5 | IL-12p70 | IL-18 |
| CCL3, CCL18, CCL6 | IL-12p70 | CCL2/MCP1 |
| CCL3, CCL18, CCL7 | IL-12p70 | TNF/TNFalpha |
| CCL3, CCL18, CCL8 | IL-12p70 | MMP9 |
| CCL3, CCL18, CCL9 | IL-12p70 | CK-MB |
| CCL3, CCL18, CCL10 | IL-12p70 | GDF-15 |
| CCL3, CCL18, CCL11 | IL-12p70 | H-FABP/FABP3 |
| CCL3, CCL18, CCL12 | IL-12p70 | hs-CRP |
| CCL3, CCL18, CCL13 | IL-12p70 | LpPLA2 |
| CCL3, CCL18, CCL14 | IL-12p70 | MPO |
| CCL3, CCL18, CCL15 | IL-12p70 | myoglobin |
| CCL3, CCL18, CCL16 | IL-12p70 | NT-proBNP |
| CCL3, CCL18, CCL17 | IL-12p70 | PAPP-A |
| CCL3, CCL18, CCL18 | IL-12p70 | soluble FAS |
| CCL3, CCL18, CCL19 | IL-12p70 | TIMP-1 |
| CCL3, CCL18, CCL20 | IL-12p70 | IL-34 |
| CCL3, CCL18, CCL21 | IL-12p70 | IL-23 |
| CCL3, CCL18, CCL22 | IL-12p70 | IL-17 |
| CCL3, CCL18, CCL23 | IL-12p70 | CXCR4/CXCL12 (SDF-1) |
| CCL3, CCL18, CCL24 | IL-12p70 | CXCL16 |
| CCL3, CCL18, CCL25 | IL-12p70 | CCL25 TEC |
| CCL3, CCL18, CCL26 | IL-12p70 | CCR9 |
| CCL3, CCL18, CCL27 | IL-12p70 | |
| CCL3, CCL18, CCL28 | IL-12p70 | sCD40L |
| CCL3, CCL18, CCL5 | IL-18 | CCL2/MCP1 |
| CCL3, CCL18, CCL6 | IL-18 | TNF/TNFalpha |
| CCL3, CCL18, CCL7 | IL-18 | MMP9 |
| CCL3, CCL18, CCL8 | IL-18 | CK-MB |
| CCL3, CCL18, CCL9 | IL-18 | GDF-15 |
| CCL3, CCL18, CCL10 | IL-18 | H-FABP/FABP3 |
| CCL3, CCL18, CCL11 | IL-18 | hs-CRP |
| CCL3, CCL18, CCL12 | IL-18 | LpPLA2 |
| CCL3, CCL18, CCL13 | IL-18 | MPO |
| CCL3, CCL18, CCL14 | IL-18 | myoglobin |
| CCL3, CCL18, CCL15 | IL-18 | NT-proBNP |
| CCL3, CCL18, CCL16 | IL-18 | PAPP-A |
| CCL3, CCL18, CCL17 | IL-18 | soluble FAS |
| CCL3, CCL18, CCL18 | IL-18 | TIMP-1 |
| CCL3, CCL18, CCL19 | IL-18 | IL-34 |
| CCL3, CCL18, CCL20 | IL-18 | IL-23 |
| CCL3, CCL18, CCL21 | IL-18 | IL-17 |
| CCL3, CCL18, CCL22 | IL-18 | CXCR4/CXCL12 (SDF-1) |
| CCL3, CCL18, CCL23 | IL-18 | CXCL16 |
| CCL3, CCL18, CCL24 | IL-18 | CCL25 TEC |
| CCL3, CCL18, CCL25 | IL-18 | CCR9 |
| CCL3, CCL18, CCL25 | IL-18 | |
| CCL3, CCL18, CCL26 | IL-18 | sCD40L |
| CCL3, CCL18, CCL5 | CCL2/MCP1 | TNF/TNFalpha |
| CCL3, CCL18, CCL6 | CCL2/MCP1 | MMP9 |
| CCL3, CCL18, CCL7 | CCL2/MCP1 | CK-MB |
| CCL3, CCL18, CCL8 | CCL2/MCP1 | GDF-15 |
| CCL3, CCL18, CCL9 | CCL2/MCP1 | H-FABP/FABP3 |
| CCL3, CCL18, CCL10 | CCL2/MCP1 | hs-CRP |
| CCL3, CCL18, CCL11 | CCL2/MCP1 | LpPLA2 |
| CCL3, CCL18, CCL12 | CCL2/MCP1 | MPO |
| CCL3, CCL18, CCL13 | CCL2/MCP1 | myoglobin |
| CCL3, CCL18, CCL14 | CCL2/MCP1 | NT-proBNP |
| CCL3, CCL18, CCL15 | CCL2/MCP1 | PAPP-A |
| CCL3, CCL18, CCL16 | CCL2/MCP1 | soluble FAS |
| CCL3, CCL18, CCL17 | CCL2/MCP1 | TIMP-1 |
| CCL3, CCL18, CCL18 | CCL2/MCP1 | IL-34 |
| CCL3, CCL18, CCL19 | CCL2/MCP1 | IL-23 |
| CCL3, CCL18, CCL20 | CCL2/MCP1 | IL-17 |
| CCL3, CCL18, CCL21 | CCL2/MCP1 | CXCR4/CXCL12 (SDF-1) |
| CCL3, CCL18, CCL22 | CCL2/MCP1 | CXCL16 |
| CCL3, CCL18, CCL23 | CCL2/MCP1 | CCL25 TEC |
| CCL3, CCL18, CCL24 | CCL2/MCP1 | CCR9 |
| CCL3, CCL18, CCL25 | CCL2/MCP1 | |
| CCL3, CCL18, CCL26 | CCL2/MCP1 | sCD40L |
| CCL3, CCL18, CCL5 | TNF/TNFalpha | MMP9 |
| CCL3, CCL18, CCL6 | TNF/TNFalpha | CK-MB |
| CCL3, CCL18, CCL7 | TNF/TNFalpha | GDF-15 |
| CCL3, CCL18, CCL8 | TNF/TNFalpha | H-FABP/FABP3 |
| CCL3, CCL18, CCL9 | TNF/TNFalpha | hs-CRP |
| CCL3, CCL18, CCL10 | TNF/TNFalpha | LpPLA2 |
| CCL3, CCL18, CCL11 | TNF/TNFalpha | MPO |
| CCL3, CCL18, CCL12 | TNF/TNFalpha | myoglobin |
| CCL3, CCL18, CCL13 | TNF/TNFalpha | NT-proBNP |
| CCL3, CCL18, CCL14 | TNF/TNFalpha | PAPP-A |
| CCL3, CCL18, CCL15 | TNF/TNFalpha | soluble FAS |
| CCL3, CCL18, CCL16 | TNF/TNFalpha | TIMP-1 |
| CCL3, CCL18, CCL17 | TNF/TNFalpha | IL-34 |
| CCL3, CCL18, CCL18 | TNF/TNFalpha | IL-23 |
| CCL3, CCL18, CCL19 | TNF/TNFalpha | IL-17 |
| CCL3, CCL18, CCL20 | TNF/TNFalpha | CXCR4/CXCL12 (SDF-1) |
| CCL3, CCL18, CCL21 | TNF/TNFalpha | CXCL16 |
| CCL3, CCL18, CCL22 | TNF/TNFalpha | CCL25 TEC |
| CCL3, CCL18, CCL23 | TNF/TNFalpha | CCR9 |
| CCL3, CCL18, CCL24 | TNF/TNFalpha | |
| CCL3, CCL18, CCL25 | TNF/TNFalpha | sCD40L |
| CCL3, CCL18, CCL5 | MMP9 | CK-MB |
| CCL3, CCL18, CCL6 | MMP9 | GDF-15 |
| CCL3, CCL18, CCL7 | MMP9 | H-FABP/FABP3 |
| CCL3, CCL18, CCL8 | MMP9 | hs-CRP |
| CCL3, CCL18, CCL9 | MMP9 | LpPLA2 |
| CCL3, CCL18, CCL10 | MMP9 | MPO |
| CCL3, CCL18, CCL11 | MMP9 | myoglobin |
| CCL3, CCL18, CCL12 | MMP9 | NT-proBNP |
| CCL3, CCL18, CCL13 | MMP9 | PAPP-A |
| CCL3, CCL18, CCL14 | MMP9 | soluble FAS |
| CCL3, CCL18, CCL15 | MMP9 | TIMP-1 |
| CCL3, CCL18, CCL16 | MMP9 | IL-34 |
| CCL3, CCL18, CCL17 | MMP9 | IL-23 |
| CCL3, CCL18, CCL18 | MMP9 | IL-17 |
| CCL3, CCL18, CCL19 | MMP9 | CXCR4/CXCL12 (SDF-1) |
| CCL3, CCL18, CCL20 | MMP9 | CXCL16 |
| CCL3, CCL18, CCL21 | MMP9 | CCL25 TEC |
| CCL3, CCL18, CCL22 | MMP9 | CCR9 |
| CCL3, CCL18, CCL23 | MMP9 | |
| CCL3, CCL18, CCL24 | MMP9 | sCD40L |
| CCL3, CCL18, CCL5 | CK-MB | GDF-15 |
| CCL3, CCL18, CCL6 | CK-MB | H-FABP/FABP3 |
| CCL3, CCL18, CCL7 | CK-MB | hs-CRP |
| CCL3, CCL18, CCL8 | CK-MB | LpPLA2 |
| CCL3, CCL18, CCL9 | CK-MB | MPO |
| CCL3, CCL18, CCL10 | CK-MB | myoglobin |
| CCL3, CCL18, CCL11 | CK-MB | NT-proBNP |
| CCL3, CCL18, CCL12 | CK-MB | PAPP-A |
| CCL3, CCL18, CCL13 | CK-MB | soluble FAS |
| CCL3, CCL18, CCL14 | CK-MB | TIMP-1 |
| CCL3, CCL18, CCL15 | CK-MB | IL-34 |
| CCL3, CCL18, CCL16 | CK-MB | IL-23 |
| CCL3, CCL18, CCL17 | CK-MB | IL-17 |
| CCL3, CCL18, CCL18 | CK-MB | CXCR4/CXCL12 (SDF-1) |
| CCL3, CCL18, CCL19 | CK-MB | CXCL16 |
| CCL3, CCL18, CCL20 | CK-MB | CCL25 TEC |
| CCL3, CCL18, CCL21 | CK-MB | CCR9 |
| CCL3, CCL18, CCL22 | CK-MB | |
| CCL3, CCL18, CCL23 | CK-MB | sCD40L |
| CCL3, CCL18, CCL5 | GDF-15 | H-FABP/FABP3 |
| CCL3, CCL18, CCL6 | GDF-15 | hs-CRP |
| CCL3, CCL18, CCL7 | GDF-15 | LpPLA2 |
| CCL3, CCL18, CCL8 | GDF-15 | MPO |

TABLE B-continued

| | | |
|---|---|---|
| CCL3, CCL18, CCL9 | GDF-15 | myoglobin |
| CCL3, CCL18, CCL10 | GDF-15 | NT-proBNP |
| CCL3, CCL18, CCL11 | GDF-15 | PAPP-A |
| CCL3, CCL18, CCL12 | GDF-15 | soluble FAS |
| CCL3, CCL18, CCL13 | GDF-15 | TIMP-1 |
| CCL3, CCL18, CCL14 | GDF-15 | IL-34 |
| CCL3, CCL18, CCL15 | GDF-15 | IL-23 |
| CCL3, CCL18, CCL16 | GDF-15 | IL-17 |
| CCL3, CCL18, CCL17 | GDF-15 | CXCR4/CXCL12 (SDF-1) |
| CCL3, CCL18, CCL18 | GDF-15 | CXCL16 |
| CCL3, CCL18, CCL19 | GDF-15 | CCL25 TEC |
| CCL3, CCL18, CCL20 | GDF-15 | CCR9 |
| CCL3, CCL18, CCL21 | GDF-15 | |
| CCL3, CCL18, CCL22 | GDF-15 | sCD40L |
| CCL3, CCL18, CCL5 | H-FABP/FABP3 | hs-CRP |
| CCL3, CCL18, CCL6 | H-FABP/FABP3 | LpPLA2 |
| CCL3, CCL18, CCL7 | H-FABP/FABP3 | MPO |
| CCL3, CCL18, CCL8 | H-FABP/FABP3 | myoglobin |
| CCL3, CCL18, CCL9 | H-FABP/FABP3 | NT-proBNP |
| CCL3, CCL18, CCL10 | H-FABP/FABP3 | PAPP-A |
| CCL3, CCL18, CCL11 | H-FABP/FABP3 | soluble FAS |
| CCL3, CCL18, CCL12 | H-FABP/FABP3 | TIMP-1 |
| CCL3, CCL18, CCL13 | H-FABP/FABP3 | IL-34 |
| CCL3, CCL18, CCL14 | H-FABP/FABP3 | IL-23 |
| CCL3, CCL18, CCL15 | H-FABP/FABP3 | IL-17 |
| CCL3, CCL18, CCL16 | H-FABP/FABP3 | CXCR4/CXCL12 (SDF-1) |
| CCL3, CCL18, CCL17 | H-FABP/FABP3 | CXCL16 |
| CCL3, CCL18, CCL18 | H-FABP/FABP3 | CCL25 TEC |
| CCL3, CCL18, CCL19 | H-FABP/FABP3 | CCR9 |
| CCL3, CCL18, CCL20 | H-FABP/FABP3 | |
| CCL3, CCL18, CCL21 | H-FABP/FABP3 | sCD40L |
| CCL3, CCL18, CCL5 | hs-CRP | LpPLA2 |
| CCL3, CCL18, CCL6 | hs-CRP | MPO |
| CCL3, CCL18, CCL7 | hs-CRP | myoglobin |
| CCL3, CCL18, CCL8 | hs-CRP | NT-proBNP |
| CCL3, CCL18, CCL9 | hs-CRP | PAPP-A |
| CCL3, CCL18, CCL10 | hs-CRP | soluble FAS |
| CCL3, CCL18, CCL11 | hs-CRP | TIMP-1 |
| CCL3, CCL18, CCL12 | hs-CRP | IL-34 |
| CCL3, CCL18, CCL13 | hs-CRP | IL-23 |
| CCL3, CCL18, CCL14 | hs-CRP | IL-17 |
| CCL3, CCL18, CCL15 | hs-CRP | CXCR4/CXCL12 (SDF-1) |
| CCL3, CCL18, CCL16 | hs-CRP | CXCL16 |
| CCL3, CCL18, CCL17 | hs-CRP | CCL25 TEC |
| CCL3, CCL18, CCL18 | hs-CRP | CCR9 |
| CCL3, CCL18, CCL19 | hs-CRP | |
| CCL3, CCL18, CCL20 | hs-CRP | sCD40L |
| CCL3, CCL18, CCL5 | LpPLA2 | MPO |
| CCL3, CCL18, CCL6 | LpPLA2 | myoglobin |
| CCL3, CCL18, CCL7 | LpPLA2 | NT-proBNP |
| CCL3, CCL18, CCL8 | LpPLA2 | PAPP-A |
| CCL3, CCL18, CCL9 | LpPLA2 | soluble FAS |
| CCL3, CCL18, CCL10 | LpPLA2 | TIMP-1 |
| CCL3, CCL18, CCL11 | LpPLA2 | IL-34 |
| CCL3, CCL18, CCL12 | LpPLA2 | IL-23 |
| CCL3, CCL18, CCL13 | LpPLA2 | IL-17 |
| CCL3, CCL18, CCL14 | LpPLA2 | CXCR4/CXCL12 (SDF-1) |
| CCL3, CCL18, CCL15 | LpPLA2 | CXCL16 |
| CCL3, CCL18, CCL16 | LpPLA2 | CCL25 TEC |
| CCL3, CCL18, CCL17 | LpPLA2 | CCR9 |
| CCL3, CCL18, CCL18 | LpPLA2 | |
| CCL3, CCL18, CCL19 | LpPLA2 | sCD40L |
| CCL3, CCL18, CCL5 | MPO | myoglobin |
| CCL3, CCL18, CCL6 | MPO | NT-proBNP |
| CCL3, CCL18, CCL7 | MPO | PAPP-A |
| CCL3, CCL18, CCL8 | MPO | soluble FAS |
| CCL3, CCL18, CCL9 | MPO | TIMP-1 |
| CCL3, CCL18, CCL10 | MPO | IL-34 |
| CCL3, CCL18, CCL11 | MPO | IL-23 |
| CCL3, CCL18, CCL12 | MPO | IL-17 |
| CCL3, CCL18, CCL13 | MPO | CXCR4/CXCL12 (SDF-1) |
| CCL3, CCL18, CCL14 | MPO | CXCL16 |
| CCL3, CCL18, CCL15 | MPO | CCL25 TEC |
| CCL3, CCL18, CCL16 | MPO | CCR9 |
| CCL3, CCL18, CCL17 | MPO | Oemrwasingh |
| CCL3, CCL18, CCL18 | MPO | sCD40L |
| CCL3, CCL18, CCL5 | myoglobin | NT-proBNP |
| CCL3, CCL18, CCL6 | myoglobin | PAPP-A |
| CCL3, CCL18, CCL7 | myoglobin | soluble FAS |
| CCL3, CCL18, CCL8 | myoglobin | TIMP-1 |
| CCL3, CCL18, CCL9 | myoglobin | IL-34 |
| CCL3, CCL18, CCL10 | myoglobin | IL-23 |
| CCL3, CCL18, CCL11 | myoglobin | IL-17 |
| CCL3, CCL18, CCL12 | myoglobin | CXCR4/CXCL12 (SDF-1) |
| CCL3, CCL18, CCL13 | myoglobin | CXCL16 |
| CCL3, CCL18, CCL14 | myoglobin | CCL25 TEC |
| CCL3, CCL18, CCL15 | myoglobin | CCR9 |
| CCL3, CCL18, CCL16 | myoglobin | |
| CCL3, CCL18, CCL17 | myoglobin | sCD40L |
| CCL3, CCL18, CCL5 | NT-proBNP | PAPP-A |
| CCL3, CCL18, CCL6 | NT-proBNP | soluble FAS |
| CCL3, CCL18, CCL7 | NT-proBNP | TIMP-1 |
| CCL3, CCL18, CCL8 | NT-proBNP | IL-34 |
| CCL3, CCL18, CCL9 | NT-proBNP | IL-23 |
| CCL3, CCL18, CCL10 | NT-proBNP | IL-17 |
| CCL3, CCL18, CCL11 | NT-proBNP | CXCR4/CXCL12 (SDF-1) |
| CCL3, CCL18, CCL12 | NT-proBNP | CXCL16 |
| CCL3, CCL18, CCL13 | NT-proBNP | CCL25 TEC |
| CCL3, CCL18, CCL14 | NT-proBNP | CCR9 |
| CCL3, CCL18, CCL15 | NT-proBNP | |
| CCL3, CCL18, CCL16 | NT-proBNP | sCD40L |
| CCL3, CCL18, CCL5 | PAPP-A | soluble FAS |
| CCL3, CCL18, CCL6 | PAPP-A | TIMP-1 |
| CCL3, CCL18, CCL7 | PAPP-A | IL-34 |
| CCL3, CCL18, CCL8 | PAPP-A | IL-23 |
| CCL3, CCL18, CCL9 | PAPP-A | IL-17 |
| CCL3, CCL18, CCL10 | PAPP-A | CXCR4/CXCL12 (SDF-1) |
| CCL3, CCL18, CCL11 | PAPP-A | CXCL16 |
| CCL3, CCL18, CCL12 | PAPP-A | CCL25 TEC |
| CCL3, CCL18, CCL13 | PAPP-A | CCR9 |
| CCL3, CCL18, CCL14 | PAPP-A | |
| CCL3, CCL18, CCL15 | PAPP-A | sCD40L |
| CCL3, CCL18, CCL5 | soluble FAS | TIMP-1 |
| CCL3, CCL18, CCL6 | soluble FAS | IL-34 |
| CCL3, CCL18, CCL7 | soluble FAS | IL-23 |
| CCL3, CCL18, CCL8 | soluble FAS | IL-17 |
| CCL3, CCL18, CCL9 | soluble FAS | CXCR4/CXCL12 (SDF-1) |
| CCL3, CCL18, CCL10 | soluble FAS | CXCL16 |
| CCL3, CCL18, CCL11 | soluble FAS | CCL25 TEC |
| CCL3, CCL18, CCL12 | soluble FAS | CCR9 |
| CCL3, CCL18, CCL13 | soluble FAS | |
| CCL3, CCL18, CCL14 | soluble FAS | sCD40L |
| CCL3, CCL18, CCL5 | TIMP-1 | IL-34 |
| CCL3, CCL18, CCL6 | TIMP-1 | IL-23 |
| CCL3, CCL18, CCL7 | TIMP-1 | IL-17 |
| CCL3, CCL18, CCL8 | TIMP-1 | CXCR4/CXCL12 (SDF-1) |
| CCL3, CCL18, CCL9 | TIMP-1 | CXCL16 |
| CCL3, CCL18, CCL10 | TIMP-1 | CCL25 TEC |
| CCL3, CCL18, CCL11 | TIMP-1 | CCR9 |
| CCL3, CCL18, CCL12 | TIMP-1 | |
| CCL3, CCL18, CCL13 | TIMP-1 | sCD40L |
| CCL3, CCL18, CCL5 | IL-34 | IL-23 |
| CCL3, CCL18, CCL6 | IL-34 | IL-17 |
| CCL3, CCL18, CCL7 | IL-34 | CXCR4/CXCL12 (SDF-1) |
| CCL3, CCL18, CCL8 | IL-34 | CXCL16 |
| CCL3, CCL18, CCL9 | IL-34 | CCL25 TEC |
| CCL3, CCL18, CCL10 | IL-34 | CCR9 |
| CCL3, CCL18, CCL11 | IL-34 | |
| CCL3, CCL18, CCL12 | IL-34 | sCD40L |
| CCL3, CCL18, CCL5 | IL-23 | IL-17 |
| CCL3, CCL18, CCL6 | IL-23 | CXCR4/CXCL12 (SDF-1) |
| CCL3, CCL18, CCL7 | IL-23 | CXCL16 |
| CCL3, CCL18, CCL8 | IL-23 | CCL25 TEC |
| CCL3, CCL18, CCL9 | IL-23 | CCR9 |
| CCL3, CCL18, CCL10 | IL-23 | |
| CCL3, CCL18, CCL11 | IL-23 | sCD40L |
| CCL3, CCL18, CCL5 | IL-17 | CXCR4/CXCL12 (SDF-1) |

TABLE B-continued

| | | |
|---|---|---|
| CCL3, CCL18, CCL6 | IL-17 | CXCL16 |
| CCL3, CCL18, CCL7 | IL-17 | CCL25 TEC |
| CCL3, CCL18, CCL8 | IL-17 | CCR9 |
| CCL3, CCL18, CCL9 | IL-17 | |
| CCL3, CCL18, CCL10 | IL-17 | sCD40L |
| CCL3, CCL18, CCL5 | CXCR4/CXCL12 (SDF-1) | CXCL16 |
| CCL3, CCL18, CCL6 | CXCR4/CXCL12 (SDF-1) | CCL25 TEC |
| CCL3, CCL18, CCL7 | CXCR4/CXCL12 (SDF-1) | CCR9 |
| CCL3, CCL18, CCL8 | CXCR4/CXCL12 (SDF-1) | |
| CCL3, CCL18, CCL9 | CXCR4/CXCL12 (SDF-1) | sCD40L |
| CCL3, CCL18, CCL5 | CXCL16 | CCL25 TEC |
| CCL3, CCL18, CCL6 | CXCL16 | CCR9 |
| CCL3, CCL18, CCL7 | CXCL16 | |
| CCL3, CCL18, CCL8 | CXCL16 | sCD40L |
| CCL3, CCL18, CCL5 | CCL25 TEC | CCR9 |
| CCL3, CCL18, CCL6 | CCL25 TEC | |
| CCL3, CCL18, CCL7 | CCL25 TEC | sCD40L |
| CCL3, CCL18, CCL5 | CCR9 | |
| CCL3, CCL18, CCL6 | CCR9 | sCD40L |
| CCL3, CCL18, CCL7 | | sCD40L |

In an aspect, a positive measurement of a biomarker within the upper or positive range from Table A may indicate an association with a disease or a change in condition. In an aspect, a positive range of the select analytes using a rapid, portable system provides a discrete measure may be used to create a disease ratio or report on one specific finding. The positive number is relevant to diagnose disease. The system reports on a specific measure compared to a control for an individual patient, not the median or mean of a bead based multiplexing technologies. Referring to Table A, the range measure represents a method to screen a population. In an aspect, the device may be specific for diagnosing a disease in a specific patient.

Prognostic chemokine markers have been reported to be able to aid clinical decision making to risk stratify patients that are more likely to experience an emergent of fatal acute myocardial infarction (AMI). Table C with Table A represents the multiplex proteins with their range of detection sensitivity and range indicative of a clinical disease. For example if chemokines CCL3, CCL5, and CCL18 individually or combined at their highest range(s) are all elevated, then the patient is likely to experience a future fatal AMI.

The temporal changes in each target analytes rise and decline is indicative of differing clinical information. The levels of analytes change over time as the patient's condition changes. The changes may happen over a period of days rather than a period of hours. This information combined with data regarding the patient's signs and symptoms is entered into the medical decision support software system to provide a decisive disease prognosis or diagnosis.

It has been demonstrated that patients having all 3 chemokines, CCL3, CCL5, CCL18, elevated in the highest tertile had an increased risk of a future fatal event 2.5 to 5.65 hazard ratio ($p<0.011$). It has been further demonstrated that cardiac troponin T (TnT) with a value of 0.29 ng/ml for those experiencing an event was not in any way indicative of the patient's worsening cardiac health nor did it have any relevance to a future fatal event over 180 days. Hence using the CMOS image sensor applying the balanced detection methodology used to capture the relative change in low light conditions, then transposed into an output using a software algorithm would report a patient being at risk for a future fatal AMI, when cardiac troponin was negative, yet CCL3, CCL5, CCL18 individually or in total were detected in their highest tertile.

Table C lists some positive biomarker combinations and findings resulting from the novel multiplexing of multiple markers that may be associated with disease or an improvement in health. In Table C, "Pos/–" indicates a slightly elevated low range of positive.

TABLE C

| Multiplex Marker | MIP 1 alpha | RANTES | CCL18 | HFABP | PaPPa | hsCRP | hs cTnI | PlGF |
|---|---|---|---|---|---|---|---|---|
| Indeterminate chest Pain | | | | | | | | |
| Indeterminate chest Pain patient had arthritis and diabetes | | | | | | Pos | | |
| Indeterminate chest Pain | Pos | | Pos | | | | | |
| UAP NTEMI | Pos | Pos | Pos | | | | | |
| Indeterminate chest Pain for 2 hours | | Pos | Pos/— | Pos | Pos | | | |
| Indeterminate chest Pain for 12 hours | | | | Pos | Pos | | Pos | |
| post AMI 10 days | | | Pos | | | | Pos | |
| post AMI 60 days | | | Pos | | | | | |
| Trauma patient unconscious | | Pos | Pos | —/Pos | | | | |
| 35 year old 16 weeks pregnant women | Pos | | | | | Pos | | Pos |
| 37 year old considering pregnancy | Pos | Pos | Pos | | | Pos | | |

TABLE C-continued

| | | | | | |
|---|---|---|---|---|---|
| Patient with breast cancer | | | Pos | | |
| Cancer patient receiving radiation therapy | | Pos | Pos | | Pos |
| Diabetic patient with chronic wound | Pos | Pos | | | |
| Diabetic patient with chronic wound sample taken 2 weeks after wound care treatment | | Within normal range | Pos | | |
| Patient with arthritis taking anti-inflammatory drugs using hsCRP to measure the effect of the reduction in generalized inflammation | | Elevated but not within a positive range | | Elevated but not within a positive range | Pos |

| Multiplex Marker | Nt-proBNP | IP-10 | MIC-1 | cystatin C | LPPLA2 | Findings resulting from the novel multiplexing of multiple markers that may be associated with disease or an improvement in health |
|---|---|---|---|---|---|---|
| Indeterminate chest Pain | | | | | | All negative rule out 99.9% sensitivity |
| Indeterminate chest Pain patient had arthritis and diabetes | | | | | | Follow up with physician as all cardiac indicators are negative. |
| Indeterminate chest Pain | | Pos | | | —/Pos | Early indicator of future cardiac event |
| UAP NTEMI | | | | | | Early indicator of future cardiac event |
| Indeterminate chest Pain for 2 hours | | | | | | MI in progress |
| Indeterminate chest Pain for 12 hours | Pos | | | | | MI in progress w/ sig heart tissue damage |
| post AMI 10 days | Pos | | Pos | Pos | | Worsening cardiac condition |
| post AMI 60 days | | | | Pos/— | | Improving cardiac tissue perhaps defibrillator implant |
| Trauma patient unconscious | | | | | | Tissue damage no cardiac involvement, continue to monitor in 4 hours |
| 35 year old 16 weeks pregnant women | | Pos | | | | Risk of miscarriage and possible cardiac involvement |
| 37 year old considering pregnancy | | | | | Pos | Patient would require a cardiac consult to monitor her health during the pregnancy |

TABLE C-continued

| | | | | |
|---|---|---|---|---|
| Patient with breast cancer | | | | Aggressive breast cancer |
| Cancer patient receiving radiation therapy | Pos | | Pos Pos | Progressing to a worsened cardiac status |
| Diabetic patient with chronic wound | | Reduced from normal | | Wound is not ready for healing therefore skin grafting or other definitive wound closure measures would be ineffective. |
| Diabetic patient with chronic wound sample taken 2 weeks after wound care treatment | | within normal range | | Wound is now ready for healing therefore skin grafting or other definitive wound closure measures would be effective. |
| Patient with arthritis taking anti-inflammatory drugs using hsCRP to measure the effect of the reduction in generalized inflammation | | | Pos | If elevated from a prior reading the anti-inflammatory drug. Cystatin C is elevated due to chronic poor renal function to be considered when ordering the drug. |

Table C reports on the multiplexing design of the kit using coated glass slides as the substrate. Inclusive in the list are the earliest reported chemokines related to a fatal cardiac event individually or in combination CCL3, CCL5, CCL18, CXCL10 (IP-10). In addition there are markers (cTnI, hs CRP) indicative an active AMI. PaPPa, PIGF, HFABP are used to report an AMI after cardiac tissue necrosis but before cTnI is elevated. Mic 1 alpha and GDF 15 are used to report in conjunction with elevated CCL18 and Nt-proBNP a worsening cardiac condition for those patients who have experienced an AMI and require further diagnosis to consider treatment options. Cystatin C is a measure of glomerular filtration rates (GFR). This marker in combination with the CCL3, CCL5, CCL18 and CXCL10 enhances a measure of the patients overall likelihood of progressing to a fatal AMI. Lp PLA 2 reported to be associated with vulnerable plaque is included as a test measure comparing its reliability to the demonstrated predictors of an impending fatal event due to their response to key aspects of coronary vessel modification.

For example in a trauma patient in which the CCL3, CCL18, cTnI, PaPPa, PIGF, Mic 1 alpha, HFABP, Nt-proBNP is slightly elevated, hs CRP is elevated and CCL5 is highly elevated and the patient has an obvious traumatic injury, the clinician could rule out cardiac involvement during their triage.

The multiplexing system reports each individual analyte, or protein as a number. Based upon previously demonstrated clinical information which defined the clinical positive range (see e.g. Table A), a clinician will be provided with information to aid clinical decision making. If cardiac troponin I is elevated to the positive range, due to the multiplexing of the combination of markers, however CCL3 is not elevated, or CCL18 is not within the highest tertile of positive ranges, this may indicate the patient is now experiencing an AMI and needs appropriate treatment. Studies have demonstrated the chemokines CCL3, CCL5, CCL18 and CXCL-10 (IP-10) are the earliest markers of an impending AMI. CCL3 may not be significantly raised on a population of AMI patients, however in a population of unstable angina patients who progressed to a cardiac event, CCL3 may have a higher elevation. Hence the multiplexed device and method to report on a series of relevant cardiac markers, is novel and medically indicated due to each markers novel temporal expression and relationship to changes on coronary vessel damage, remodeling as well as those markers elevated in response to cardiac tissue necrosis.

The level of a biomarker in the biological sample taken from the subject may be compared with a reference level of the biomarker in a healthy individual to determine whether the level of said biomarker is significantly different. A significant difference may be calculated using known statistical analysis techniques. Non-limiting examples of statistical analysis techniques that may be used to calculate the risk score include cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, Linear Regression or classification algorithms, Nonlinear Regression or classification algorithms, analysis of variants (ANOVA), hierarchical analysis or clustering algorithms; hierarchical algorithms using decision trees; kernel based machine algorithms such as kernel partial least squares algorithms, kernel matching pursuit algorithms, kernel Fisher's discriminate analysis algorithms, kernel principal components analysis algorithms, or Student's t-test statistical hypothesis test. In an exemplary embodiment, a Student's t-test statistical hypothesis test is used to calculate a P-value. In some embodiments, a P-value of less than about 0.1, 0.09, 0.08, 0.07, 0.06, 0.07, 0.06, 0.05, 0.04, 0.03, 0.02 or 0.01 signifies a statistically significant difference. In some embodiments, tertile analysis may be used.

(d) Cardiac Failure

The detection method may predict a cardiac failure. As used herein, a "cardiac failure" may be defined as any cardiac failure that leads to death or may lead to death if immediate emergency medical intervention is not administered. Non-limiting examples of cardiac failure may include myocardial infarction, acute myocardial infarction, ST elevation myocardial infarction (STEMI), non ST elevation myocardial infarction (NSTEMI), acute plaque rupture in any of the coronary vessels, stable angina or unstable angina. In preferred embodiments, a cardiac failure is a myocardial infarction. In other preferred embodiments, a cardiac failure is an acute myocardial infarction. In still other preferred embodiments, a cardiac failure is an acute plaque rupture in any of the coronary vessels. In some embodiments, a cardiac failure is a ST elevation myocardial infarction. In certain embodiments, a cardiac failure is a non ST elevation myocardial infarction. In certain embodiments, a cardiac failure is a non healing or remodeling of damaged cardiac tissue.

The method of the invention may predict an imminent cardiac failure. As used herein, an "imminent cardiac failure" is a cardiac failure that may occur within about 180 days after one or more biomarkers of the invention are measured in a subject. In exemplary embodiments, an imminent cardiac failure is a cardiac failure that may occur within about two weeks after one or more biomarkers of the invention are measured in a subject. In some embodiments, an imminent cardiac failure may be a cardiac failure that may occur about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, or 180 days after one or more biomarkers of the invention are measured in a subject. In other embodiments, an imminent cardiac failure may be a cardiac failure that may occur about 1, 2, 3, 4, 5, or 6 days after one or more biomarkers of the invention are measured in a subject. In yet other embodiments, an imminent cardiac failure may be a cardiac failure that may occur about 4, 5, 6, 7, 8, 9 or 10 days after one or more biomarkers of the invention are measured in a subject. In other embodiments, an imminent cardiac failure may be a cardiac failure that may occur about 11, 12, 13, 14, 15, 16, or 17 days after one or more biomarkers of the invention are measured in a subject.

(e) Measuring a Biomarker

As described in section (c) above, a level of a biomarker may refer to the amount of RNA coding for the biomarker present in a sample, the rate of transcription of a biomarker, the amount of biomarker protein in a sample, the rate of protein synthesis, or the level of enzymatic activity of a biomarker. In each instance, the level is quantified, such that a value, an average value, or a range of values is determined. In one embodiment, amount of protein is quantified.

In some embodiments, the method used for measuring the concentration of the biomarker is a method suitable for multiplex protein microarray concentration determination. A multiplexed assay device, as defined herein, is an assay capable of simultaneously determining the concentration of three or more different sample analytes using a single device and/or method. Including in the measuring of the protein is a discrete measure of the concentration from a fluid sample rather than reporting on the mean or median of a multiple samples from the same fluid source.

A suitable method of detection may involve contacting a biomarker with an epitope binding agent. The term "epitope binding agent" refers to an agent that is capable of binding to a specific epitope of a biomolecule. Non-limiting examples of epitope binding agents may include aptamers, double-stranded DNA sequence, ligands and fragments of ligands, receptors and fragments of receptors, antibodies and fragments of antibodies, coenzymes, coregulators, allosteric molecules, and ions. In an exemplary embodiment, a biomarker is contacted with an antibody or antibody fragment. For instance, by way of non-limiting example, a biomarker may be contacted with one or more monoclonal antibodies specific for the biomarker.

An exemplary detection means may be used as a point of care device. Typically, such a detection means is portable, and in exemplary embodiments, may be disposable. In one exemplary embodiment, a detection means may employ a photovoltaic detection system. For instance, a detection means may be able to use ambient light to produce a detectable signal based on the level of a biomarker in a biological sample.

In order to adjust the expected concentrations of the sample analytes in the test sample to fall within the dynamic range of the assay, the test sample may be diluted to reduce the concentration of the sample analytes prior to analysis. The degree of dilution may depend on a variety of factors including but not limited to the type of assay used to measure the analytes, the reagents utilized in the assay, and the type of bodily fluid contained in the test sample.

In an alternative embodiment, in order to adjust the expected concentrations of the sample analytes in the test sample to fall within the dynamic range of the assay, the test sample may be concentrated to increase the concentration of the sample analytes prior to analysis.

In one exemplary embodiment, if the test sample is human serum and the multiplexed assay is an antibody-based capture-sandwich assay, employing specifically identified monoclonal antibody pairs or nanoparticles having a specific charge unique to the biomarker of detection interest, the test sample is diluted by adding a volume of diluent that is about 5 times the original test sample volume prior to analysis. In another exemplary embodiment, if the test sample is human plasma and the multiplexed assay is an antibody-based capture-sandwich assay, the test sample is diluted by adding a volume of diluent that is about 2,000 times the original test sample volume prior to analysis.

The diluent may be any fluid that does not interfere with the function of the assay used to measure the concentration of the analytes in the test sample. Non-limiting examples of suitable diluents include deionized water, distilled water, saline solution, Ringer's solution, phosphate buffered saline solution, TRIS-buffered saline solution, standard saline citrate, and HEPES-buffered saline.

In an alternative embodiment, in certain methods a biological sample may be concentrated to allow detection of a biomarker.

(f) Predicting Cardiac Failure

The method of the invention may predict cardiac failure in a subject using a portable disposable testing device. For instance, a subject may complain of discomfort with symptoms described as being similar to cardiac failure symptoms as described in Section (a) above. However, normal diagnostic tests performed on the subject at the time of the discomfort may show no evidence of cardiac failure. Despite this, the subject later suffers a cardiac failure within about two weeks after the diagnostic tests were performed. In such a situation, a method of the invention may be used to predict the cardiac failure despite the lack of evidence of cardiac failure based on normal diagnostic tests.

As used herein, "normal diagnostic tests" may be any clinical tests known in the art to diagnose cardiac failure. Clinical tests normally used to diagnose cardiac failure may include electrocardiography, echocardiography, an X-ray of the chest, a cardiac stress test, an echocardiography, scintigraphy, a cardiac index, clinically tested biomarkers, cardiac catheterization, intravascular ultrasound, computed tomography, or a combination thereof.

In some embodiments, the normal diagnostic test is an X-ray of the chest. Methods of performing a chest X-ray are known in the art and may employ ionizing radiation in the form of X-rays to generate images of the chest.

In other embodiments, the normal diagnostic test is a cardiac stress test. Methods of performing a cardiac stress test are known in the art. In short, cardiac stress test, or cardiac diagnostic test, measures the heart's ability to respond to external stress in a controlled clinical environment. The stress response may be induced by on a treadmill, pedaling a stationary exercise bicycle ergometer or with intravenous pharmacological stimulation. The response of the heart to stress may then be measured using cardiography.

In still other embodiments, the normal diagnostic test is a cardiac index. A cardiac index is a vasodynamic parameter that relates the cardiac output to body surface area, relating heart performance to the size of the individual. A cardiac index may be used as a marker of how well the heart is functioning as a pump by directly correlating the volume of blood pumped by the heart with an individual's body surface area.

In other embodiments, the normal diagnostic test is determining the level of clinically known biomarkers—for instance, troponin.

In some preferred embodiments, the normal diagnostic test is cardiography. Non-limiting examples of cardiography that may be used to diagnose cardiac failure may include echocardiography, electrocardiography and scintigraphy. An echocardiogram is a sonogram of the heart also known as a cardiac ultrasound. Echocardiography uses standard ultrasound techniques to image the heart. In some preferred embodiments, the cardiography is scintigraphy. Methods of performing scintigraphy are known in the art and may use a radiotracer followed by imaging the distribution of the radiotracer in the subject. In other preferred embodiments, the cardiography is echocardiography. Methods of performing echography are known in the art and are a sonogram of the heart also known as a cardiac ultrasound. Echocardiography uses standard ultrasound techniques to image the heart.

In a preferred embodiment, the normal diagnostic test is electrocardiography. Methods of performing electrocardiography are known in the art. Electrocardiography is a transthoracic interpretation of the electrical activity of the heart over a period of time, as detected by electrodes attached to the outer surface of the skin and recorded by a device external to the body. The recording produced by this non-invasive procedure is termed as electrocardiogram (ECG or EKG). ECG may be used to measure the rate and regularity of heartbeats as well as the size and position of the chambers, the presence of any damage to the heart, and the effects of drugs or devices used to regulate the heart (such as a pacemaker).

In an exemplary embodiment, the normal diagnostic test is electrocardiography and determining the level of troponin.

The method of the invention may predict an imminent cardiac failure in a subject when the level of biomarkers selected from the group consisting of CCL3, CCL18, CCL5, hs, troponin, PaPPA, and NTproB (for example) are elevated compared to normal. The range for select markers may be 1.5 to 10 fold greater than a normal in the biological sample are significantly different from a reference level in a healthy control individual, and normal diagnostic test results are negative. In some embodiments, the negative normal diagnostic results are negative electrocardiogram results. In other embodiments, the negative normal diagnostic results are levels of troponin in the biological sample are not significantly different when compared to the level of troponin in a biological sample of a healthy control individual. In preferred embodiments, the negative normal diagnostic results are levels of troponin in the biological sample are not significantly different when compared to the level of troponin in a biological sample of a healthy control individual, and the electrocardiogram results are negative electrocardiogram results.

In preferred embodiments, a method of the invention may predict an imminent serious cardiac failure when the level of biomarkers selected from the group consisting of CCL3, CCL18, CCL5, and NTproB in a biological sample from a subject are significantly different from a reference level of the biomarkers in a biological sample of a healthy control individual, the level of troponin in the biological sample is not significantly different from a reference level of the biomarkers in a biological sample of a healthy control individual, and normal diagnostic test results are negative. Furthermore, the risk of future adverse events increased with an increasing number of biomarkers in the upper tertile; patients with CCL3, CCL5 and CCL18 concentrations in the highest tertile had a fourfold higher risk of future adverse events, compared to patients without a single biomarker in the highest tertile.

In an exemplary embodiments, a method of the invention may predict an imminent cardiac failure when the level of biomarkers selected from the group consisting of CCL3, CCL18, CCL5, and NTproB in a biological sample from a subject are significantly different from a reference level of the biomarkers in a biological sample of a healthy control individual, the level of troponin in the biological sample is not significantly different from a reference level of the biomarkers in a biological sample of a healthy control individual, and electrocardiogram results are negative.

IV. System

In various aspects, a system for detecting analytes in a sample of bodily fluid from a patient and determining a condition of the patient is provided. FIG. 23 is a block diagram illustrating the elements of a system 200 in one embodiment. In this embodiment, the system 200 may include the device 100 described herein above and associated elements to control the operation of the device, to analyze the data obtained using the device to determine the concentrations of the one or more analytes, and further analyzing the analyte concentrations to determine a condition of the patient.

The system 200 may include the device 100, a display 202 to communicate input to and/or output from the other elements of the system 200, one or more processors 204 to execute software included in the system 200, a computer-readable medium 206 encoded with analyte detection application 208 software and a memory 210 containing stored information used to implement the instructions encoded within the analyte detection application 208.

The analyte detection application 208 includes one or more modules executable on the one or more processors 204 containing instructions used to implement the various functions of the system 200. The one or more modules include a control module 212 to control the operation of the device and to coordinate the execution of the instructions of the other modules of the analyte detection application 208. For example, the control module 212 may control the circuitry associated with the one or more sensors of the device 100, any microfluidic controls included within the device 100, and/or the circuitry associated with the one or more light sources of the device 100.

In another embodiment, the modules of the system may include a balanced detection module 214 to control the operation of the one or more sensors and/or light sources of the device 100 to implement a balanced detection method described previously herein. FIG. 24 is a flow chart illustrating the operation of the balanced detection module 214 in one embodiment. The balanced detection module 214 may obtain the initial sensor readings from the reference sensor of the device 100 at step 302, and initial sensor readings from the detection sensor of the device 100 at step 304. The balanced detection module 214 may then subtract the detection sensor output and the reference sensor output at step 306 to calculate a differential output signal. If the differential signal is determined to be not equal to zero at step 308, the balanced detection module 214 may adjust the intensity of the light produced by one or more of the light sources, and/or adjust the associated circuitry of the sensors such as a variable resistor setting at step 310. Steps 302-308 are then repeated until the differential output signal is equal to zero at step 308. Once a differential output signal of zero is achieved at step 308, the differential output signal may then be monitored without further adjustment at step 312 to determine the concentration of any analyte in a sample introduced into the device 100.

The modules of the system may further include an analyte detection module 216 to process combined output signals received from the balanced detection module 214 to determine the presence and/or concentration of the one or more analytes contained within the sample introduced into the device 100. FIG. 25 is a flow chart illustrating the operation of the analyte detection module 216 in one embodiment. The analyte detection module 216 may obtain a differential output signal for each of the one or more analytes from the balanced detection module 214 at step 402. If a differential output signal is determined to be equal to zero at step 404, the analyte concentration is set equal to zero at step 406 and the differential output signal for another analyte is received at step 402. If the differential output signal is determined to be not equal to zero at step 404, calibration data for that analyte is obtained at step 406 from the calibration database 226 stored in the memory 210 of the system (see FIG. 23). Referring back to FIG. 25, the analyte concentration of the analyte may be determined at step 408 using the calibration data as described herein previously.

The modules of the system 200 may further include a post-processing module 218 to further analyze the analyte concentrations calculated by the analyte detection module 216 and to calculate combined quantities such as analyte concentration ratios, sums, or any other arithmetic combination of analyte concentrations without limitations. In addition, the post-processing module 218 may further analyze the analyte concentrations and classify these concentrations as low, high, or any other analyte concentration classification described herein above using the classification definitions defined within the diagnostic database 224 stored in memory 210 (see FIG. 23); these concentration classifications were described previously herein above, for example in Table C above.

FIG. 26 is a flow chart illustrating the operation of the post-processing module 218 in one embodiment. The analyte concentrations may be received from the analyte detection module 216 at step 502. Threshold values or other values or definitions used to classify the analyte concentrations may be obtained from the diagnostic database 224 at step 504. If the analyte concentration is less than a minimal detectable concentration at step 506, the analyte concentration may be defined as zero or 'negative' at step 508. If the analyte concentration is not greater than a low concentration threshold at step 510, but higher than a minimum detectable threshold at step 506, the analyte concentration may be classified as 'sub-low' or 'negative' at step 512. If the analyte concentration is less than a high concentration threshold at step 514, then the analyte concentration may be classified as low' at step 516. If the analyte concentration is greater than a high threshold at step 514, the analyte concentration may be defined as 'high' or 'positive' at step 518. All classifications of the analyte concentrations may be used to populate a diagnostic array at step 520. The diagnostic array may include each analyte, the analyte's concentration, the analyte's diagnostic classification, as well any other arithmetic combinations of analyte concentrations described previously herein above.

The modules of the system 200 may further include a diagnostic module 220 to compare the entries of the diagnostic array and to determine a condition of a patient according to one or more diagnostic rules defined within the diagnostic database 224 stored in memory 210 (see FIG. 23); these diagnostic rules were described previously herein above, for example in Table C above.

FIG. 27 is a flow chart illustrating the operation of the diagnostic module 220 in one embodiment. The diagnostic array may be received at step 602 from the post-processing module. The diagnostic rules may be obtained from the diagnostic database 224 at step 604. If the diagnostic array does not match the values or definitions provided in a diagnostic rule associated with a condition of the patient at step 506, that condition is rejected at step 608. If the diagnostic array does match the values or definitions provided in a diagnostic rule associated with a condition of the patient at step 506, that condition is assigned to the patient at step 610.

The modules of the system 200 may further include a GUI module 222 to generate one or more forms to be displayed by the display 202. These forms may be used to receive input from the user to the system 200 or to communicate output from the system 200 to the user. For example, a form may be displayed to communicate the analyte concentrations determined by the system in a graph or table format. In another example, a form may be displayed to communicate a condition of a patient determined by the system.

The CRM 206 may include volatile media, nonvolatile media, removable media, non-removable media, and/or another available medium that can be accessed by the computing device or processors 204. By way of example and not limitation, computer readable medium 206 comprises computer storage media and communication media. Computer storage media includes nontransient memory, volatile media, nonvolatile media, removable media, and/or non-removable media implemented in a method or technology for storage of information, such as computer readable instructions, data structures, program modules, or other data. Communication media may embody computer readable instructions, data structures, program modules, or other data and include an information delivery media or system.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

Example 1: Identifying Biomarkers that have Diagnostic and Prognostic Utility in Alzheimer's Disease (AD)

ECG and blood tests for electrocardiography, a chest X-ray, monitoring of heart rhythm, blood oxygen level, and blood tests for myocardial markers such as troponin I or T, a D-dimer, ischemia-modified albumin (IMA), Myeloperoxidase (MPO), C-reactive protein, Glycogen Phosphorylase Isoenzyme BB-(GPBB), myoglobin, CK-MB, and BNP may be performed in a cohort of patients complaining of chest pain. The same tests may be performed everyday and cardiac failure may be recorded and treated if and when it occurred. The clinical tests performed on a subset of the patients complaining of chest pain may not produce any positive results, indicating that these tests could not diagnose a cardiac failure. Surprisingly, this subset of patients may develop cardiac failure. In addition, this subset of patients also may have levels of CCL3, CCL18, CCL5 that may be significantly different from the levels of CCL3, CCL18, CCL5 in a healthy control.

Example 2: CCL5 (RANTES) and CCL18 (PARC) are Specific Markers of Refractory Unstable Angina Pectoris and are Transiently Raised During Severe Ischemic Symptoms Methods
Study Population.
All chemokines and inflammatory parameters were determined in plasma samples of a patient cohort, derived from the well defined APRAIS (Acute Phase Reaction and Ischemic Syndromes) study. In brief, 54 patients who were admitted to the emergency department of the Leiden University Medical Center between March and September 1995 with unstable angina pectoris Braunwald class IIIB were included and followed for up to 18 months. Venous blood samples were obtained on admission (t=0) after 2 (t=2) and 180 days after admission (t=180), centrifuged and plasma aliquots were stored at −80° C. until further analysis. All patients had received standard medical therapy, i.e. aspirin 300 mg orally, nitro-glycerine intravenously and heparin infusion based titrated to the activated partial thromboplastin time. A clinical end point of the APRAIS study was the occurrence of refractory unstable angina pectoris during hospitalization. Unstable angina pectoris was considered refractory if angina at rest, despite medical treatment, remained or re-occurred, prompting invasive coronary assessment and subsequent revascularization therapy. Although the study cohort was relatively small, it constituted a clearly defined, well documented population with a similar starting point. All subjects gave written informed consent and the study protocol was approved by the Ethics Committee of the Leiden University Medical Center.

Isolation of Cells.
PBMCs from patients (t=0 and t=180) as well as from 6 healthy age matched volunteers were isolated from venous EDTA blood samples through density centrifugation on Histopaque (Sigma, St. Louis, Mo.). PBMCs were collected from the interphase and washed twice with culture medium, consisting of Iscove's modified Dulbecco's medium containing glutamax (Gibco, Paisly, UK) and supplemented with 10% FCS. PBMCs were cryopreserved in culture medium containing 20% FCS and 10% dimethylsulfoxide until further use.

Multiplex Chemokine Assay.
Circulating levels of the chemokines CCL2, CCL3, CCL5, CCL11, CCL17, CCL18, CCL22, CXCL8, CXCL9, CXCL10 and the chemokine like factor MIF, the cytokines OSM, IFN-γ and OPG and adhesion molecules sRank1, sVCAM and sICAM were determined in t=0 samples with a custom made multiplex bio-assay using the Bio-Plex Suspension Array system (Bio-Rad laboratories, Hercules, Calif.) Plasma samples were filtered and subsequently diluted with 10% normal rat and mouse serum (Rockland, Gilvertsville, Pa.) to block residual non-specific antibody binding. 1000 microspheres were added per chemokine (10 µl/well) in a total volume of 60 µl, together with standard and blank samples, and the suspension incubated for 1 hour in a 96 well filter plate at room temperature (RT). Then, 10 µl of biotinylated antibody mix (16.5 µg/ml) was added and incubated for 1 hour at RT. Afterwashing with PBS-1% BSA-0.5% TWEEN® 20 [polyethylene glycol sorbitan monolaurate], beads were incubated with 50 ng/well streptavidin R-phycoerythrin (BD Biosciences, San Diego, Calif.) for 10 minutes. Finally, beads were washed again with PBS-1% BSA-0.5% TWEEN® 20 [polyethylene glycol sorbitan monolaurate], and the fluorescence intensity was measured in a final volume of 100 µl high-performance ELISA buffer (Sanquin, Amsterdam, the Netherlands). Measurements and data analysis were performed with the Bio-Plex Suspension Array system in combination with the Bio-Plex Manager software version 3.0 (Bio-Rad laboratories, Hercules, Calif.) (see also ref. No: 14).

ELISA and Other Assays.
For temporal analysis of human CCL5 and CCL18 plasma levels during follow up, the t=0, t=2 and t=180 samples were assayed by a CCL5 instant ELISA kit (Bender MedSystems, Vienna, Austria) and a CCL18 ELISA (RayBiotech, Norcross, Ga.), respectively, according to manufacturers protocol. Baseline inflammatory parameters such as C-reactive protein, fibrinogen, erythrocyte sedimentation rate (ESR) and plasminogen activator inhibitor 1 (PAI-1) were determined as described in detail previously 13. Soluble CD40 ligand (sCD40L) and Interleukin 6 (IL-6) were determined via a highly sensitive immunoassay (Quantakine HS, R&D Systems, Minneapolis, Minn.), t=180 CRP samples via a turbidimetric assay on a fully automated Modular P800 unit (Roche, Almere, the Netherlands).

Assessment of Heterophilic CCL5 and CCL18 Interaction.

Sodium Dodecyl Sulfate-Polyacrylamide Gel Electrophoresis (SDS-PAGE) was used to assess whether recombinant CCL5 (7.8 kDa) and synthetic CCL18 (7.8 kDa) engage in heterophilic interactions. Proteins (rCCL5, sCC118, rCCL5/sCCL18 at a 1:1 and a 1:5 weight ratio (w:w); 2 μg total protein per lane) were incubated for one hour at RT in 50 mM HEPES/0.1 mM EDTA buffer (pH=7.4), after which 25 mM of paraformaldehyde was added to cross link any formed homo- or heterodimers. After 30 minutes, protein mixtures were denatured in loading buffer and subjected to SDS-PAGE (18%; 2 μg protein per lane, one hour at 70 mV and 30 minutes at 150 mV), proteins were visualized by silver staining. Protein mixtures were also analysed on a Voyager-DE Pro MALDI-TOF mass spectrometer (PerSeptive Biosystems, Framingham, Mass.).

RT-PCR Analyses.

To assess expression of CCL5, CCL18, CCR1, CCR2, CCR3, CCR4, CCR5, CX3CR1 and human neutrophil peptide-3 (HNP-3) in PBMCs, mRNA was isolated and analyzed. Guanidium thiocyanate-phenol was used to extract total RNA from PBMCs, samples were subjected to DNAse I treatment (Promega, Madison, Wis.) after which cDNA was generated using RevertAid M-MuLV reverse transcriptase (Fermentas, Burlington, Canada) according to manufacturer's protocol 2. Semi quantitative gene expression was performed using the SYBR-Green method (Eurogentec, Liege, Belgium) on an ABI PRISM 7700 machine (Applied Biosystems, Foster City, Calif.) with primers for CCL5, CCL18, CCR1, CCR2, CCR3, CCR4, CCR5, CX3CR1, CD11b and human neutrophil peptide-3 (HNP-3). Cyclophilin and Hypoxanthine Guanine Phosphoribosyl Transferase (HPRT) were used as housekeeping genes.

Relative gene expression was calculated by subtracting the threshold cycle number (Ct) of the target gene from the average Ct of Cyclophiline and HPRT and raising two to the power of this difference.

Flow Cytometry.

CCR3 and CCR5 surface expression on CD3+ and CD 14+ PBMCs was assessed by flow cytometry. Cryopreserved PBMCs were thawed, washed three times in RPMI 1640 containing 20% FCS and subsequently stained using APC conjugated anti-CD3 and anti-CD14 antibodies (BD Biosciences, San Jose, Calif.) as well as FITC conjugated anti-CCR3 and anti-CCR5 antibodies (R&D Systems). Non-specific isotypes FITC conjugated Rat IgG2a and FITC conjugated mouse IgG2b antibodies (eBiosciences, San Diego, Calif.) were used as negative controls. Samples were analyzed with a fluorescence activated flow cytometer (FACSCalibur) and subsequently analyzed using CELL-Quest software (BD Biosciences), 50,000 cells were counted for each sample.

PBMC Stimulation Assay.

Cryopreserved PBMC specimens, obtained from six healthy volunteers were thawed as described above, plated in a U-shaped round bottom 96-well plate (Greiner Bio-one) and stimulated for 6 hours at 37° C. with plain medium (control) or medium supplemented with 50 ng/ml recombinant CCL5 (Peprotech, Rocky Hill, N.J.), 50 ng/ml of the synthetic CCL18 peptide SM-1 (sCCL18), or a combination of rCCL5 and sCCL18 (25 ng/ml per peptide) 3. After incubation, total RNA was isolated from the cells, cDNA was prepared and chemokine receptor expression was determined.

Statistical Analysis.

Differences between our study populations and the original cohort were examined by Fisher's exact test and Student's unpaired t-test. Plasma levels of chemokines and inflammatory markers were tested for normal Gaussian distribution and values were log-transformed in the case of a skewed distribution when appropriate. Regarding the latter, geometric instead of arithmetic means are given. Means were compared by unpaired two-tailed Student's t-test or Mann-Whitney U-test when appropriate. In order to assess the predictive value of CCL5 and CCL18 for the occurrence of refractory symptoms, independent of potentially confounding factors, a multivariate analysis was performed, correcting for age, HDL and ESR levels, as well as for other established cardiovascular risk factors (e.g. hypertension, hypercholesterolemia, use of lipid and blood pressure lowering medication, diabetes mellitus, smoking behaviour, BMI and history of cardiovascular disease) and biomarkers sCD40L and CRP. Quartile distribution was assessed and used for Spearman's correlation coefficient and Pearson's chi-square testing to determine the association of chemokine plasma levels as well as levels of sCD40L and CRP for the occurrence of refractory UAP. Receiver operating characteristics curves were generated to assess predictive value of chemokines for refractory ischemic symptoms. Correlation analysis between multiplex and ELISA values and between chemokines and inflammatory parameters were performed by Spearman's rank correlation test. FACS results were analyzed via paired t-test, the stimulation assay was analyzed via ANOVA. A two-sided p-value<0.05 was considered significant. All analyses were performed using SPSS version 14.0 software (SPSS, Chicago, Ill.).

Results

Study Population.

Plasma analyses on chemokines (listed in Table 1) were performed in a subcohort of previously unfrozen plasma samples of 54 consecutive patients, excluding selection bias. This subcohort, consisting of 31 patients with stabilised and 23 with refractory ischemic symptoms, matched with the original cohort on cardiovascular risk factors, history of myocardial infarction or PTCA/CABG and laboratory parameters (Tables 2A and B).

TABLE 1

| Multiplex Marker | Entrez Gene ID |
| --- | --- |
| MIP 1 alpha (CCL3) | 6348 |
| RANTES (CCL5) | 6352 |
| CCL18 | 6362 |
| HFABP | 2170 |
| PaPPa | 5069 |
| hsCRP | 1401 |
| hs cTnI | 7137 |
| PlGF Placental Growth Factor | 5228 |
| BNP | 4879 |
| IP-10 | 6327 |
| MIC-1 | 9518 |
| cystatin C | 1471 |
| LP PLA2 | 7941 |

TABLE 2A

Baseline patient characteristics and laboratory parameters.

| | Chemokine cohort (N = 54) | APRAIS (N = 211) | P-value |
|---|---|---|---|
| Age, years | 65.4 ± 11.0 | 62.7 ± 10.2 | 0.08 |
| Refractory (%) | 43 | 36 | 0.43 |
| Male gender (%) | 73.8 | 71.1 | 0.75 |
| Current smoker (%) | 24.6 | 30.5 | 0.45 |
| BMI (kg/m$^2$) | 25.2 ± 6.0 | 25.9 ± 3.36 | 0.23 |
| Diabetes (%) | 16.4 | 14.6 | 0.98 |
| Hypertension (%) | 23 | 23.5 | 0.99 |
| Statin use (%) | 8.2 | 12.2 | 0.48 |
| History of: | | | |
| Myocardial infarction (%) | 45 | 43.2 | 0.88 |
| PTCA (%) | 26 | 29.1 | 0.75 |
| CABG (%) | 23 | 21.6 | 0.86 |
| Laboratory parameters: | | | |
| Total cholesterol, mmol/l | 6.00 ± 1.5 | 6.18 ± 1.2 | 0.38 |
| HDL, mmol/l | 1.14 ± 0.4 | 1.14 ± 0.3 | 0.97 |
| CRP, mg/l * | 2.36 | 2.66 | 0.50 |
| ESR, mm/hr * | 16.44 | 14.88 | 0.30 |
| Fibrinogen, g/l * | 3.56 | 3.42 | 0.34 |

TABLE 2B

Chemokine cohort baseline patient characteristics and laboratory parameters

| | Stabilised (N = 31) | Refractory (N = 23) | P-value |
|---|---|---|---|
| Age, years | 67.3 ± 10.2 | 64.5 ± 11.4 | 0.30 |
| Male gender (%) | 87 | 63 | 0.05 |
| Current smoker (%) | 22 | 25 | 0.69 |
| BMI (kg/m$^2$) | 24.9 | 26.7 | 0.78 |
| Diabetes (%) | 9 | 19 | 0.16 |
| Hypertension (%) | 17 | 38 | 0.39 |
| History of: | | | |
| Myocardial infarction (%) | 48 | 47 | 0.89 |
| PTCA (%) | 30 | 25 | 0.57 |
| CABG (%) | 35 | 16 | 0.19 |
| Laboratory parameters: | | | |
| Hemoglobine, mmol/l | 8.27 ± 2.1 | 8.51 ± 0.8 | 0.61 |
| Hematocrite (%) | 47 | 41 | 0.26 |
| Leucocytes, 10$^9$/l | 7.49 ± 2.9 | 7.68 ± 2.2 | 0.79 |
| Platelet count, 10$^6$/l | 186.5 ± 66 | 223.9 ± 75 | 0.07 |
| Glucose, mmol/l | 7.37 ± 2.7 | 6.49 ± 1.4 | 0.15 |
| Creatinine, μmol/l | 99.2 ± 52.3 | 108.7 ± 32.1 | 0.44 |
| Cholesterol, mmol/l | 5.92 ± 1.8 | 6.16 ± 1.0 | 0.56 |
| HDL, mmol/l | 1.23 ± 0.4 | 0.99 ± 0.2 | 0.02 |
| ESR, mm/hr * | 14.15 | 20.70 | 0.03 |
| Fibrinogen, g/l * | 3.42 | 3.78 | 0.26 |
| CRP, mg/l * | 2.14 | 2.77 | 0.47 |
| sCD40L, pg/ml | 23.6 | 20.3 | 0.32 |

As not all 54 patients responded to donate blood after 180 days, ELISA analysis at this point was performed for 47 patients (stabilised 29 vs. refractory 18), but the baseline characteristics of this subcohort matched with that of the original cohort (data not shown). Comparison for baseline demographics in the chemokine cohort showed no striking differences between refractory versus stabilized patients, except for a small, but significant difference in gender composition (87% vs. 67% males; P=0.05); the mean age of all patients was 65 years (41 to 85 years). Regarding the clinical and plasma lipid parameters at baseline, total cholesterol levels in stabilized and refractory patients did not differ (5.92 vs. 6.16 mmol/l; P=0.56), whereas HDL levels were lower (1.23 vs. 0.99 mmol/l; P=0.02) in the latter population. This group also displayed an increased tendency towards a higher inflammatory status, as illustrated by elevated levels of the ESR (14.15 vs. 20.7 mm/hr; P=0.03) albeit that fibrinogen and CRP levels were essentially similar. No differences were observed in baseline sCD40L levels between groups.

Multiplex Analysis:

Upregulation of CCL5 and CCL18.

All of the chemokine and cytokine data as determined by multiplex analysis (t=0 samples) were log-transformed before further statistical analysis because of their skewed distribution profiles, except for OPG. Plasma levels of the majority of chemokines and cytokines did not differ between stabilized and refractory patients. CCL5 (23.1 vs. 32.7 ng/ml; P=0.018) and CCL18 levels (53.7 vs. 104.4 ng/ml; P=0.011) however appeared to be significantly increased in refractory patients, while there was a borderline significant increase in those of CCL3 (53.6 vs. 73.7 pg/ml; P=0.09) (Table 3 and FIG. 1A).

TABLE 3

Chemokine plasma concentrations analysed via the multiplex technique.

| Variable | Stabilised | Refractory | P-value |
|---|---|---|---|
| CCL5, pg/ml | 23158 | 32704 | 0.018 |
| CCL18, pg/ml | 53678 | 104399 | 0.011 |
| CCL2, pg/ml | 154 | 146 | 0.77 |
| CCL3, pg/ml | 53.6 | 73.7 | 0.09 |
| CCL11, pg/ml | 63.7 | 65.8 | 0.88 |
| CCL17, pg/ml | 40.3 | 51.2 | 0.34 |
| CCL22, pg/ml | 527 | 546 | 0.79 |
| CXCL8, pg/ml | 12.4 | 13.4 | 0.84 |
| CXCL9, pg/ml | 158 | 156 | 0.96 |
| CXCL10, pg/ml | 221 | 157 | 0.12 |
| MIF, pg/ml * | 330 | 439 | 0.45 |
| OPG, pg/ml* | 937 | 1096 | 0.25 |
| OSM, pg/ml | 456 | 690 | 0.25 |
| sRankL, pg/ml | 5.0 | 5.7 | 0.83 |
| sVCAM, pg/ml | 681082 | 735190 | 0.45 |
| sICAM, pg/ml | 106340 | 117625 | 0.28 |

Values are geometric means
*denotes arithmetic mean

Moreover, the observed differences in CCL5 levels remained significant after multivariate analysis adjusting for cardiovascular risk factors and sCD40L and CRP levels (P=0.023), whereas CCL18 levels were borderline significant (P=0.06). However, differences in CCL18 levels reached significance after multivariate analysis for all confounding factors but HDL (P=0.021). Therefore, CCL5 as well as CCL18 seem to be independent predictors of the occurrence of refractory ischemic symptoms, even when adjusting for sCD40L and CRP levels. Furthermore, CCL5 and CCL18 levels showed no mutual correlation (R=0.05; P=0.7), reflecting that these chemokines are regulated or operate in an independent manner. Still, although no significant heterophilic interactions between CCL5 and CCL18 were observed, it is conceivable that both chemokines, sharing CCR3 as common target receptor will interact functionally (FIGS. 6 and 7). CXCL10 had a tendency to rise in stabilised patients, although not quite significant (221.6 vs. 157.5 pg/ml; P=0.12), which could point towards a protective effect of this specific chemokine. Levels of IFN-γ were merely undetectable and are therefore not shown.

Next, it was sought to assess if CCL5 and CCL18 levels have diagnostic potential. Given the cohort size, levels of CCL5 and CCL18 were categorized into quartiles and analyzed for correlation with the occurrence of future refractory ischemic symptoms (Table 4A).

TABLE 4A

CCL5 and CCL18 quartile levels at baseline as determined by multiplex analysis

| Quartiles | CCL5 | CCL18 |
|---|---|---|
| 1 | <15.1 | <39.3 |
| 2 | >15.1 and <25.5 | >39.3 and <66.0 |
| 3 | >25.5 and <40.3 | >66.0 and <130.0 |
| 4 | >40.3 | >130.0 |

All values are in ng/ml

Figure 2A:
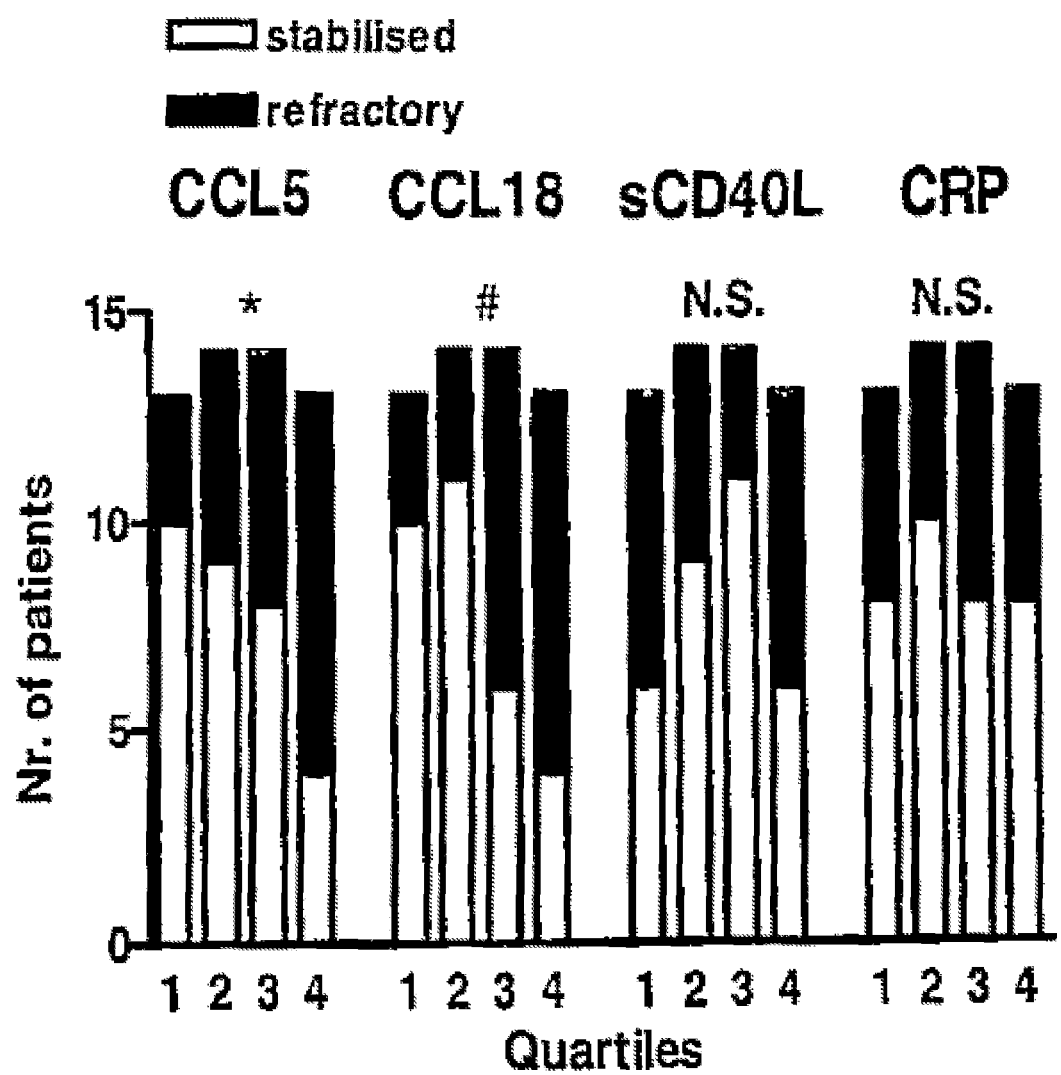
FIG. 2 depicts upper quartile plasma levels of CCL5 and CCL18. Upper quartile plasma levels of CCL5 and CCL18 were significantly associated with the occurrence of refractory ischemic symptoms in unstable angina pectoris, while sCD40L and CRP quartile levels did not show any significant correlation (A). Upper quartile levels of CCL5 at day 0 are predictive for the necessity of future revascularization procedures (B), while upper quartile levels of CCL18 were predictive for acute coronary syndromes (C) or recurrent symptoms of unstable angina pectoris (D; UAP) within the next 18 months (C,D). *P=0.02, **P=0.01, #P<0.01 and N.S.=non-significant.
Figure 2:
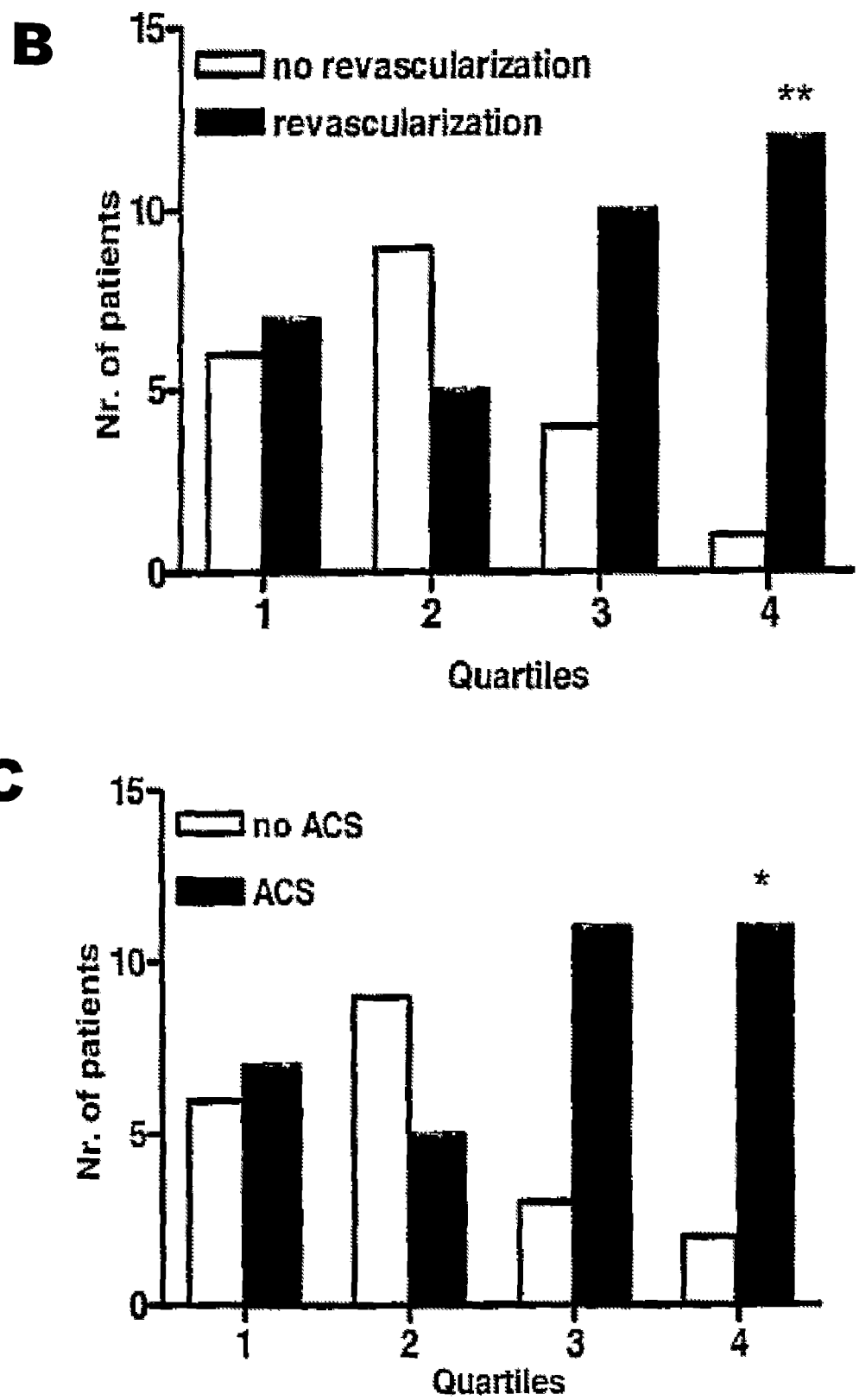

The risk of refractory ischemic symptoms was seen to be increased in the upper quartiles of CCL5 (R=0.32; P=0.017; Linear-by-linear association chi-square 5.53; P=0.019), while this trend was even more pronounced for CCL18 (R=0.392; P=0.003; linear-by-linear association chi-square 8.105; P=0.004) (FIG. 2A). Elevated CCL18 levels were slightly more predictive than those of CCL5 as indicated by the receiver operating characteristics curve (area under the curve 0.71 vs. 0.69). Cut-off values of >40 ng/ml for CCL5 and >130 ng/ml for CCL18 yielded a sensitivity of 73.9% and 65.2%, respectively as well as a specificity of 67.7% and 61.3%. Combined analysis of the upper two quartiles of CCL5 and CCL18 for the occurrence of refractory ischemic symptoms revealed a very significant relation ($x^2$ with continuity correction 8.12; P<0.01). While the sensitivity reached 47.8%, the specificity of the combined analysis was a remarkably high 90.3%. The positive predictive value of combined analysis for CCL5 and CCL18 levels was 78.5% with a concomitant negative predictive value of 70.0%. Adding sCD40L or CRP levels to the analysis did not yield any further increase in sensitivity, specificity or predictive value (data not shown).

CCL5 and CCL18 ELISA Verification and Follow-Up Analysis.

Figure 1:
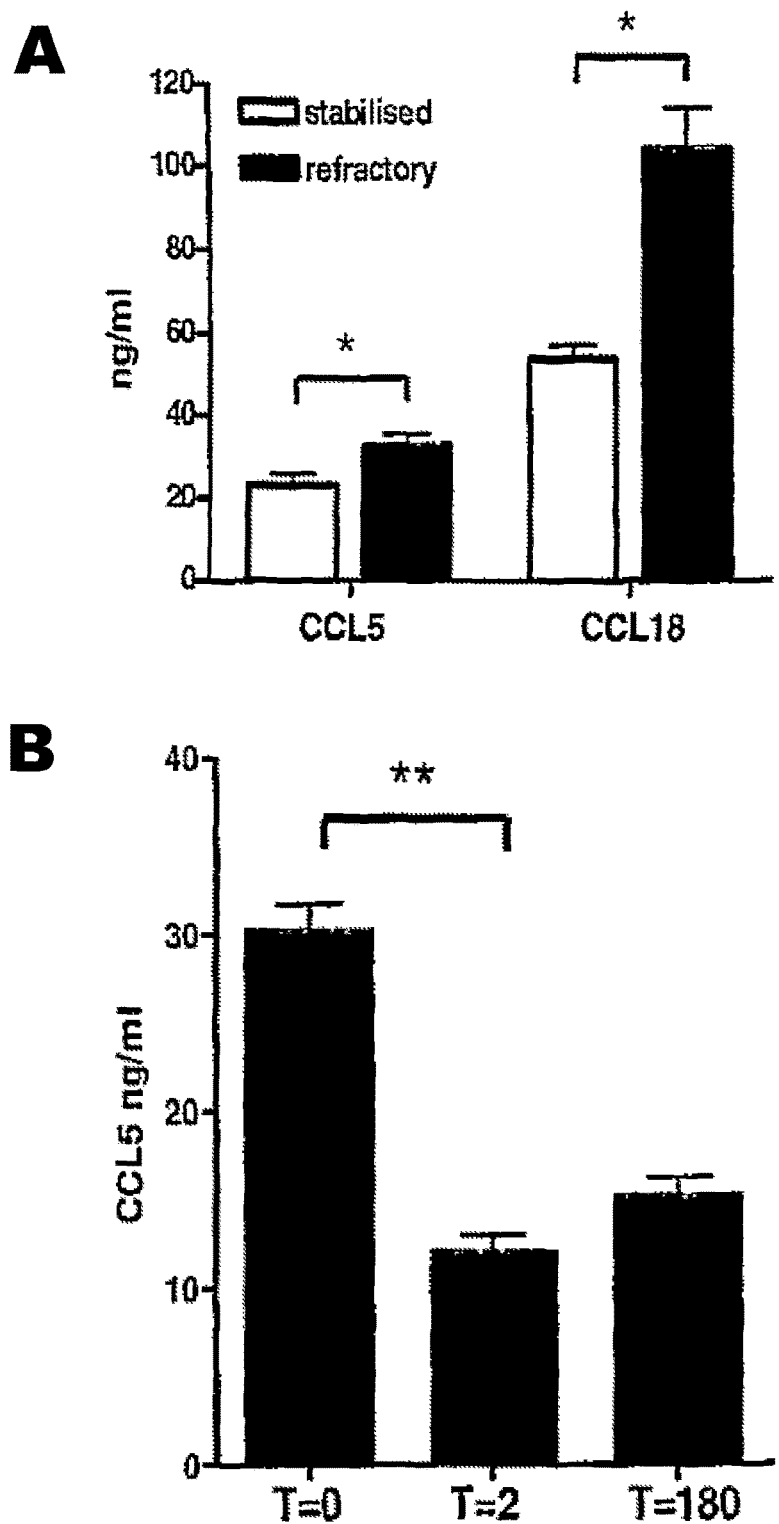
FIG. 1 depicts plasma levels of various chemokines in stabilized and refractory patients with unstable angina. CCL5 and CCL18 levels were determined by multiplex in stabilized and refractory patients with unstable angina pectoris at t=0 (A). ELISA was used for temporal patterning at t=0, t=2 and t=180 days. CCL5 levels dropped significantly at t=2 and were at the same level at t=180 (B), while CCL18 levels remained elevated at t=2 and dropped back at t=180 (C). Soluble CD40 ligand (sCD40L) levels peaked at t=0 and were lowered at t=2 and t=180 (D). CRP levels showed a peak at t=2, and lowered to sub-baseline values (t=0) at t=180 (E). Values represent mean±SEM, *P<0.05, **P<0.001 and N.S.=non-significant.
Figure 1:
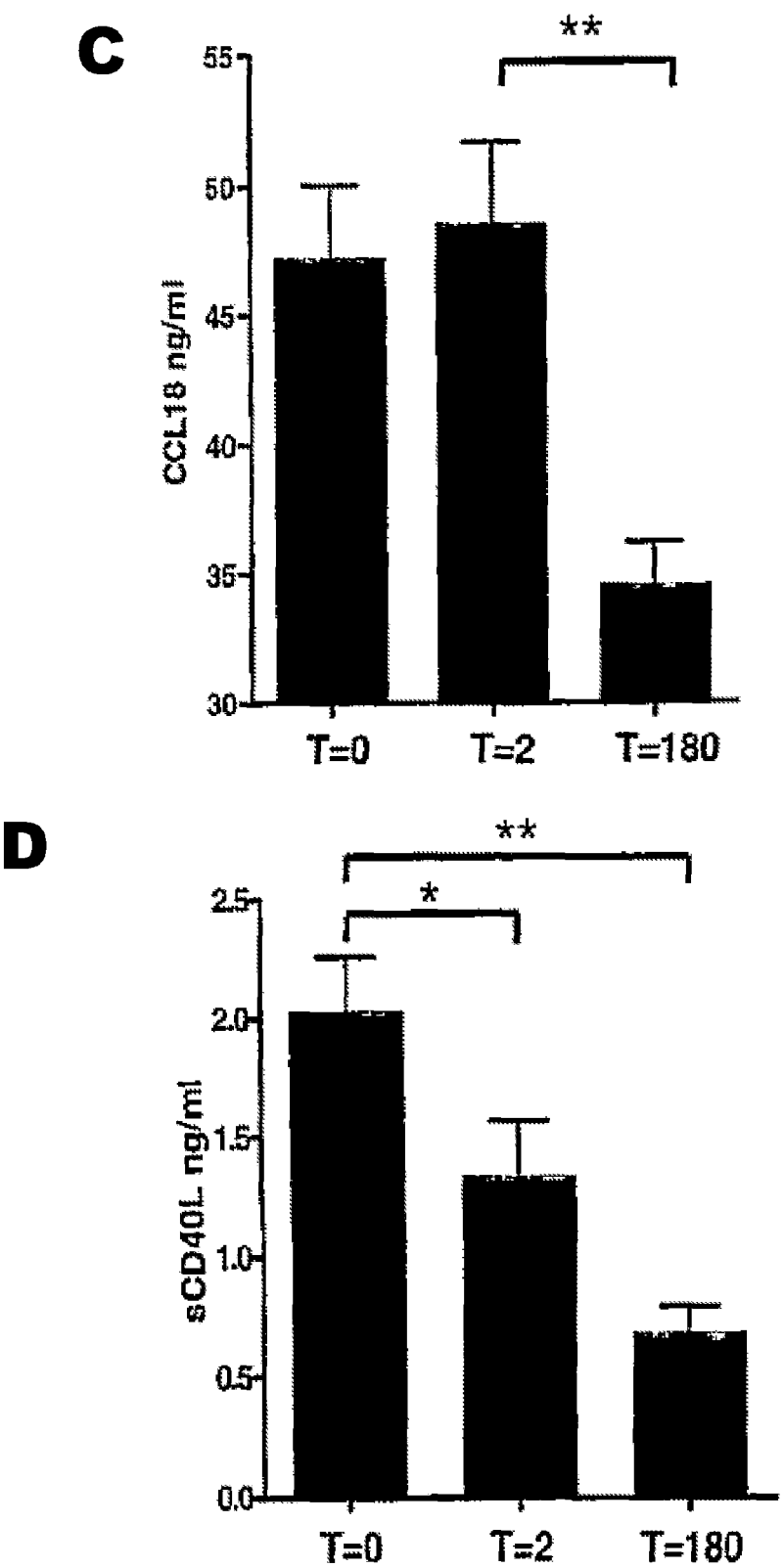
Figure 1E:
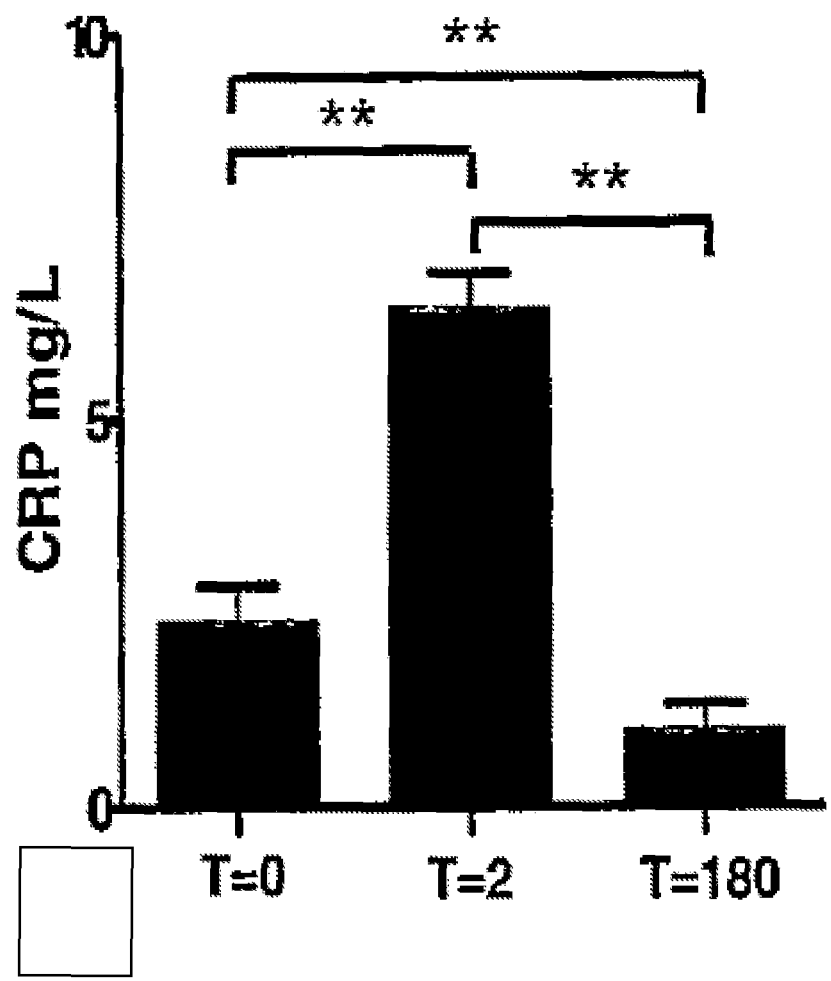

Mean and individual ELISA and multiplex CCL5 levels corresponded excellently (P<0.001). Moreover, CCL5 plasma levels were also seen to be increased in refractory compared to stabilised patients at day 0 when assessed by ELISA (36.4 vs. 26.5 ng/ml). Interestingly, already after two days, a marked decrease in plasma CCL5 levels was observed in the whole cohort (12.1 versus 30.3 ng/ml; P<0.001) and reduced CCL5 levels were also observed at t=180, showing that CCL5 is transiently raised during an episode of unstable angina pectoris (FIG. 1B). No differences between the stabilized and refractory groups at 2 and 180 days post inclusion were observed. Plasma levels of CCL18 showed a different temporal pattern after ischemic symptoms. ELISA analysis confirmed the differential expression of CCL18 at day 0 between refractory and stabilised patients (56.2 vs. 41.1 ng/ml; P=0.02). Although absolute values were slightly lower in the ELISA compared to the multiplex assay, statistical analysis revealed an excellent correlation between the two assays (Spearman's test; P<0.001). Interestingly, CCL18 levels of the total cohort at day 2 did not differ with the baseline levels (day 0), suggesting that CCL18 and CCL5 levels might be regulated via separate mechanisms. At 180 days, CCL18 levels were significantly down-regulated compared the day 2 values (48.4 vs. 34.5 ng/ml; P<0.001), suggestive of a role of CCL18 in cardiac ischemia-reperfusion related processes (FIG. 1C).

Soluble CD40 Ligand and CRP.

Levels of both sCD40L as well as CRP were significantly elevated at t=0 compared to t=180 (sCD40L 2.04 vs. 0.69 ng/ml; P<0.001, CRP 2.36 vs. 0.96 mg/l; P<0.001) (FIG. 1D, E). However, sCD40L levels started to decline already at t=2 (1.35 ng/ml; P<0.05) indicating that elevated levels at baseline reflect a platelet activation related acute phase response. As soluble CD40L t=0 and t=2 levels at correlated significantly with CCL5 t=0 and t=2 levels (t=0 R=0.40; P<0.01, t=2 R=0.35; P=0.01), elevated CCL5 levels may be primarily caused by platelet activation as well. sCD40L however showed a significant negative correlation with CCL18 levels at t=0 (R=−0.36; P=0.01), suggesting that latter represent a feedback response to platelet activation. CRP levels were even further increased at t=2 (6.43 mg/l; P<0.001) which is in keeping with previous reports, and presumably indicative of an enhanced post-ischemic systemic inflammatory status in these patients two days after ischemia and/or coronary intervention. CRP levels showed no correlations with CCL5 or CCL18 levels. Quartile levels of sCD40L as well as CRP did not have any potential to predict refractory ischemic symptoms (R=0.043 and R=−0.034; N.S) (FIG. 2A: for quartile distribution, see Table 4B).

TABLE 4B

CRP and sCD40L quartile levels at baseline.

| Quartiles | CRP mg/L | sCD40L ng/ml |
|---|---|---|
| 1 | <1.2 | <14.2 |
| 2 | >1.2 and <2.6 | >14.2 and <26.4 |
| 3 | >2.6 and <6.5 | >26.4 and <33.7 |
| 4 | >6.5 | >33.7 |

All values are in ng/ml

Inflammation and Clinical Follow-Up.

Figure 2D:
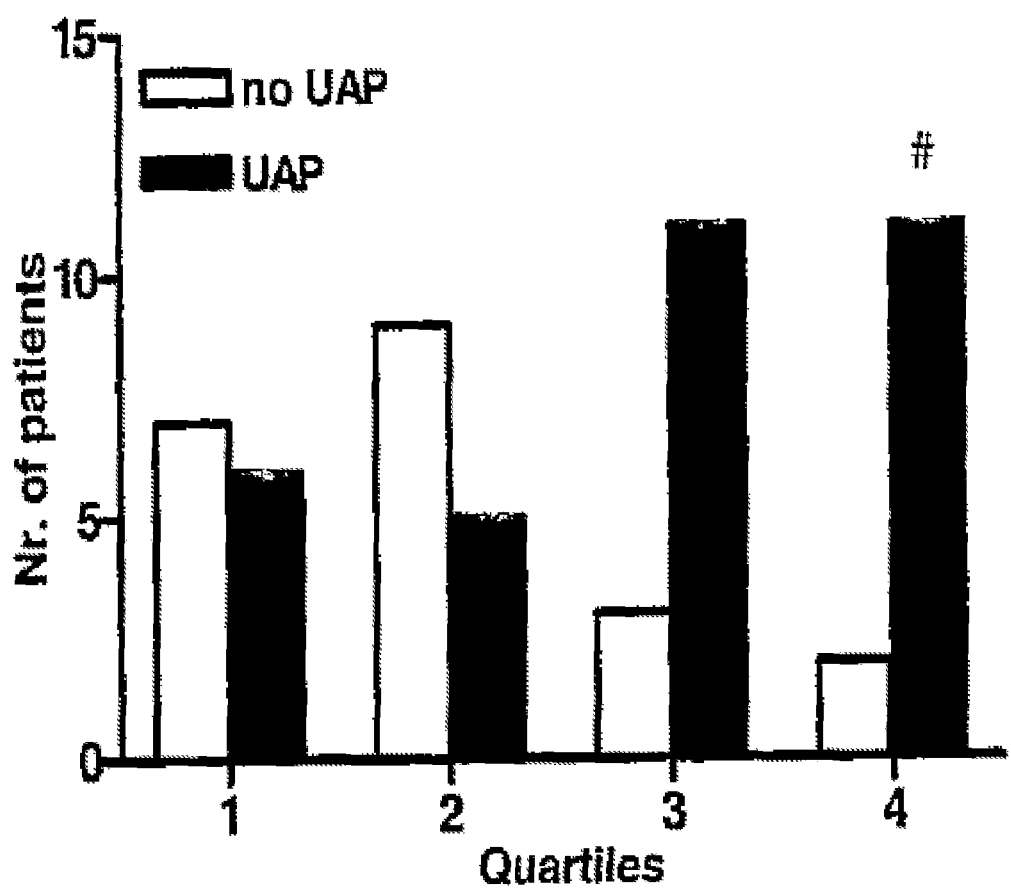
Figure 3A:
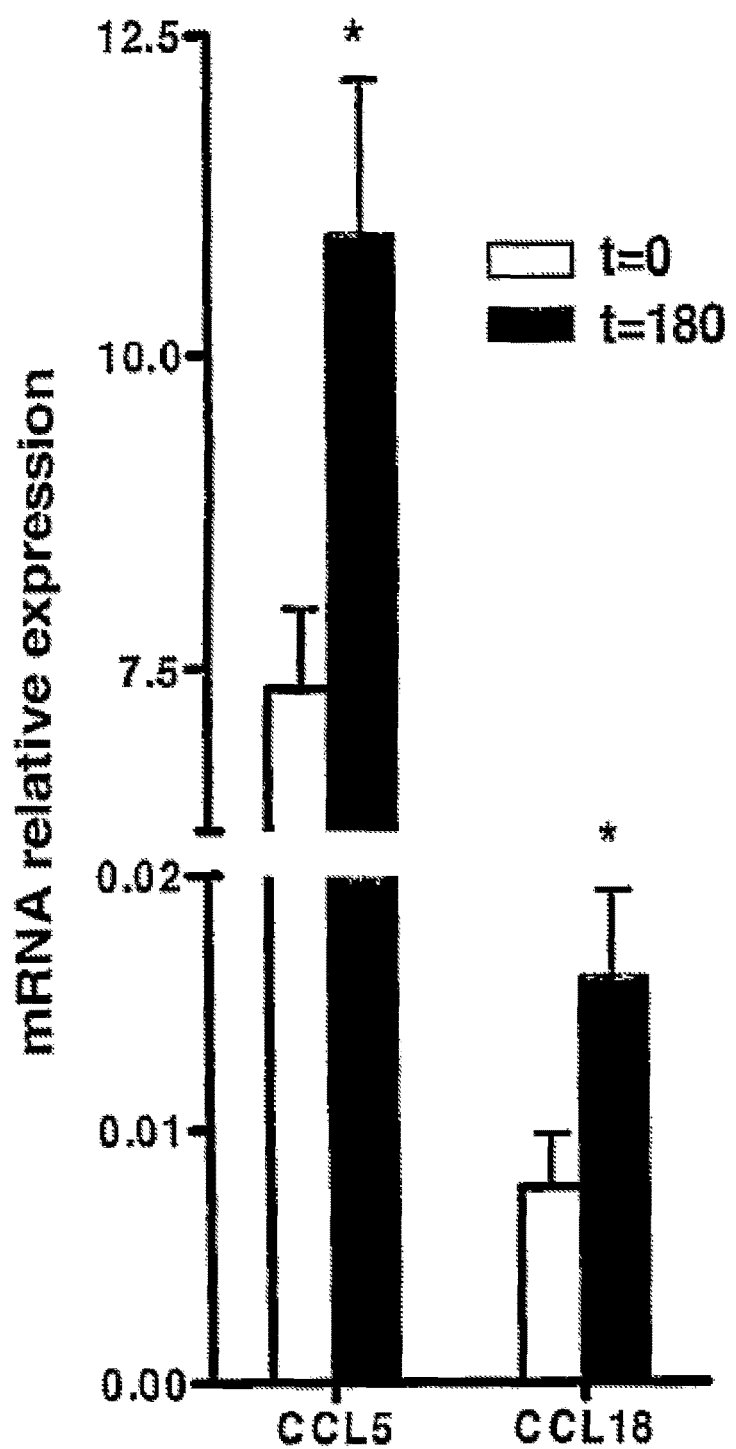
FIG. 3 depicts PCR analysis of CCL5 and CCL18 expression. Quantitative PCR analysis showed a markedly down-regulated expression of CCL5 and CCL18 in non-stimulated PBMCs of patients with ischemic symptoms at t=0 compared to PBMCs at t=180 (A). In contrast with chemokine receptor surface protein expression in PBMCs, mRNA expression of the CCL5 and CCL18 receptors CCR1, CCR3, CCR4 and CCR5 was also approximately at least 2-fold down-regulated at baseline (B). Values represent mean±SEM, *P<0.05 and **P<0.001.
Figure 3B:
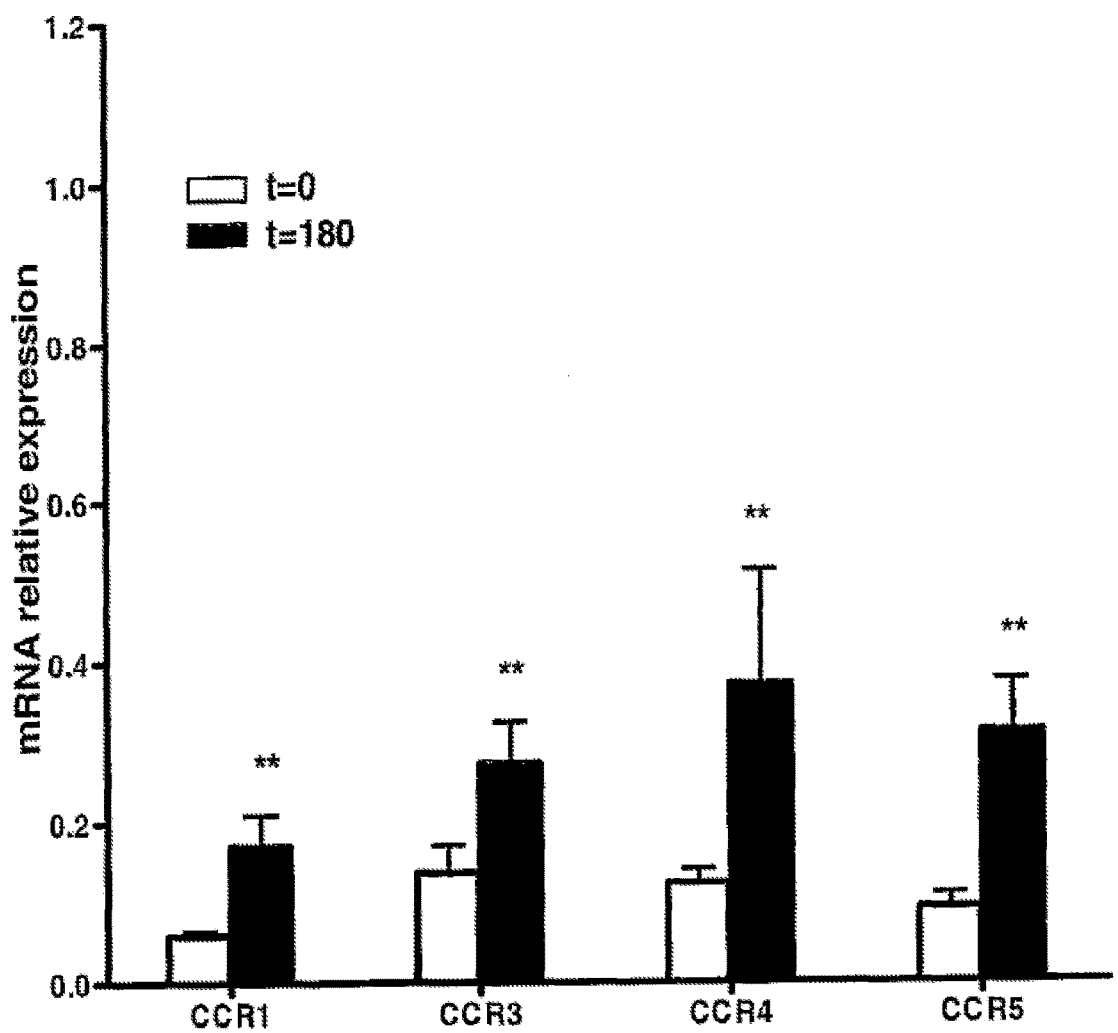

Correlation analysis for all chemokines with systemic inflammatory parameters fibrinogen, IL-6, PAI-1 and ESR revealed no association, except for a weak correlation between CXCL10 and IL-6 levels (R=0.29; P=0.02, other data not shown). Importantly, the baseline upper quartile levels of CCL5 as determined by multiplex were seen to correlate with the need for revascularization procedures within the next 18 months (R=0.35; P=0.01). Furthermore, baseline upper quartile levels of CCL18 correlated with the re-occurrence of unstable angina pectoris (UAP) during hospitalisation (R=0.36; P=0.007) as well as with the occurrence of an acute coronary syndrome (ACS) during the 18-month period of follow-up (R=0.31; P=0.02) (FIGS. 2B-D). Baseline levels of sCD40L and CRP did not correlate with any of the follow-up parameters (data not shown).

PBMC Chemokine and Chemokine Receptor Expression Analysis.

Figure 4:
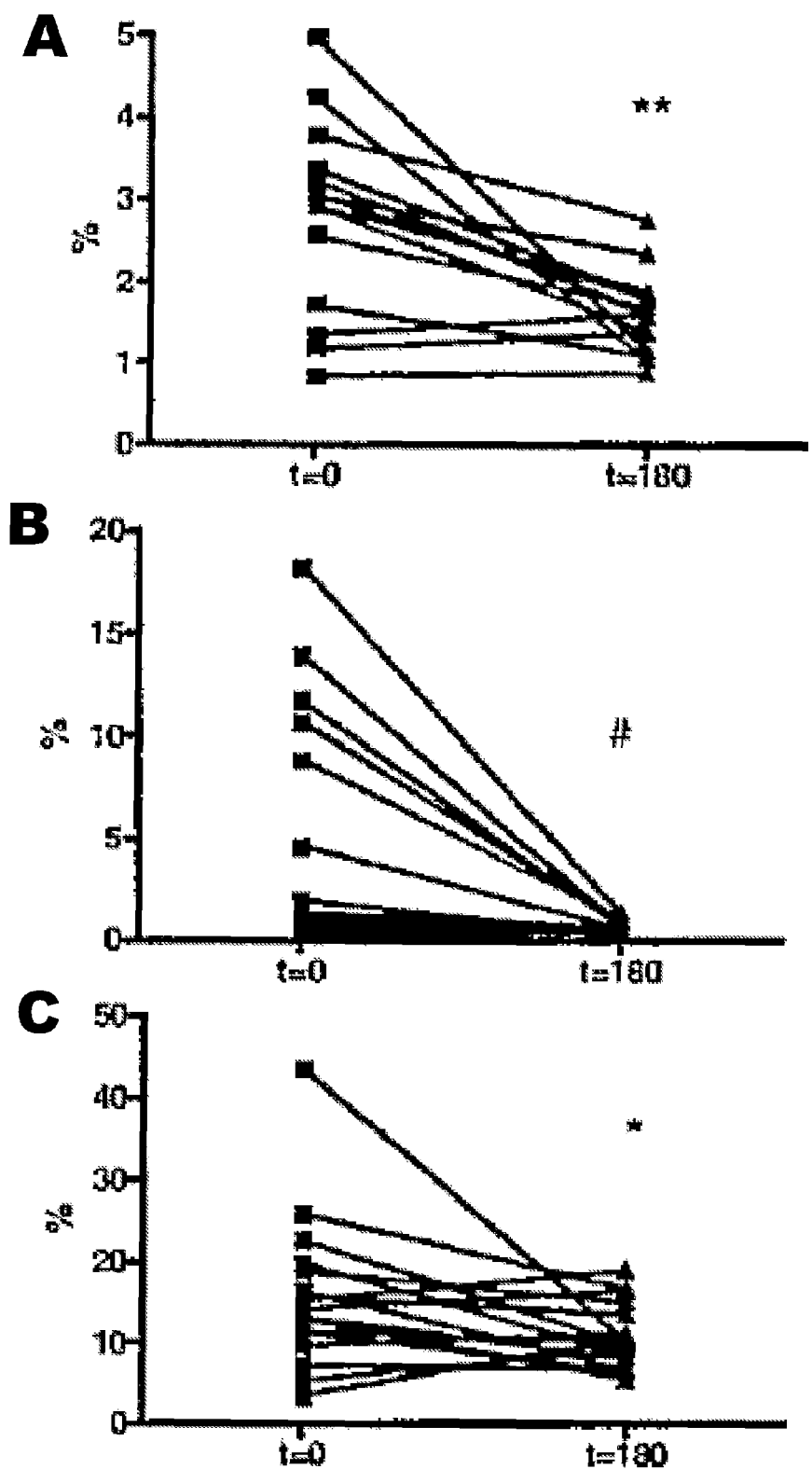
FIG. 4 depicts protein expression in PBMCs of CCR3 and CCR5. Protein expression in PBMCs of CCR3 and CCR5 showed a clear up-regulation of both receptors in $CD14^+$ cells (A,B) and CD330 cells (C,D) at baseline. Triple gating for CD14, CD3 and CCR3/5 revealed the same trend, although $CD14^+$ cells displayed more prominent up-regulation of CCR3 and CCR5 expression than $CD3^+$ cells (E,F).
Figure 4:
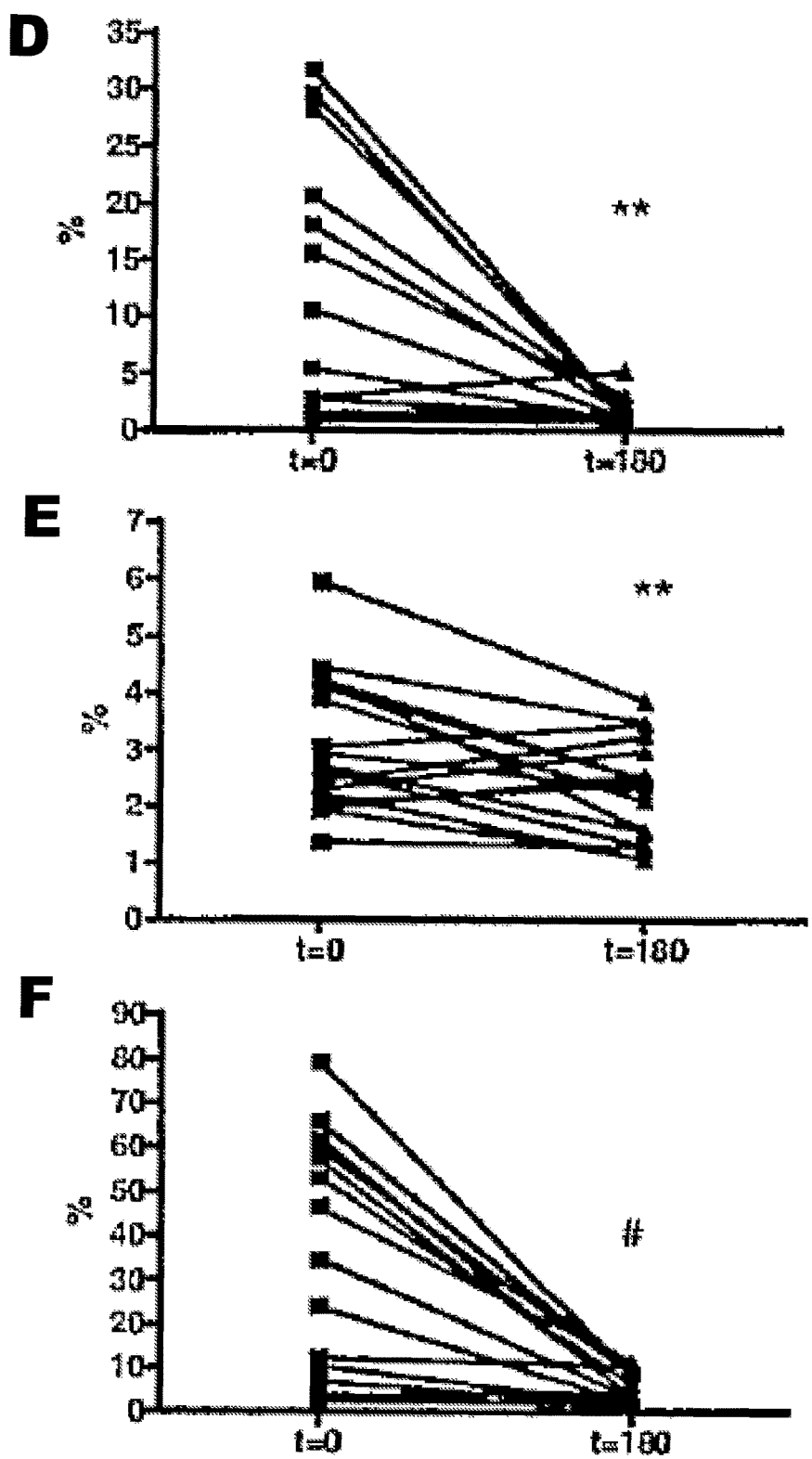
Figure 4:
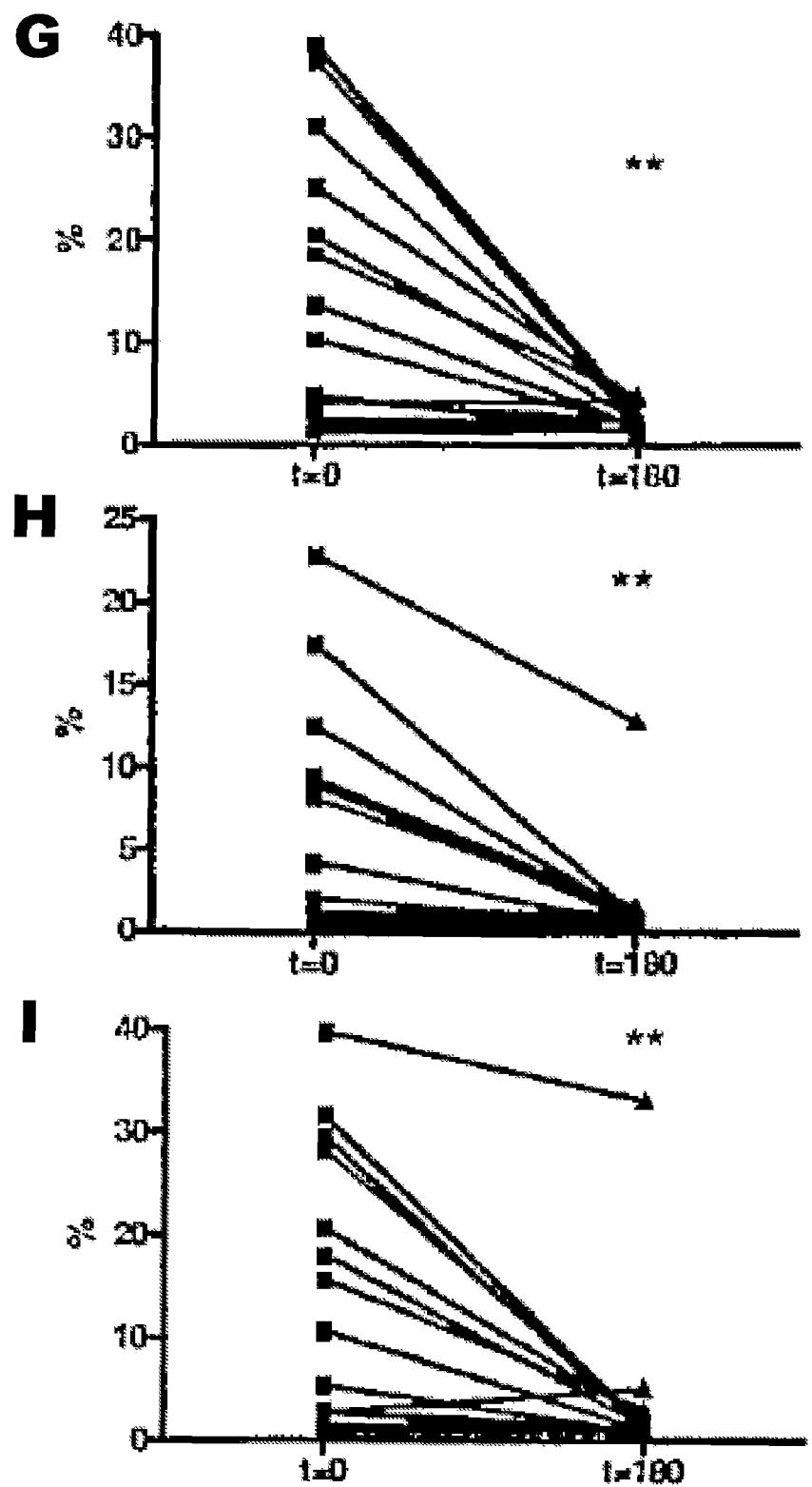

While the interaction of CCL5 with CCR1, CCR3, CCR4 and CCR5 is well described, the actual receptor for CCL18 is as yet unknown, which makes CCL18 currently an orphan ligand 17. However, CCL18 has been reported to be a competitive inhibitor of CCL11 (eotaxin) binding to CCR318. Therefore, mRNA expression of chemokine receptors CCR1, CCR3, CCR4 and CCR5 was examined as well as that of CCL5 and CCL18 in PBMCs. A remarkable highly significant down-regulation of all four involved chemokine receptors at baseline (t=0) was observed compared to PBMCs at t=180 (FIG. 24B). A similar temporal pattern was seen for CCL5 and CCL18, with CCL5 being abundantly expressed in PBMCs and CCL18 at only minor levels (FIG. 24A). Subsequent FACS analysis to detect CCR3 and CCR5 expression on $CD3^+$ T-cells and $CD14^+$ monocytes to our surprise revealed a significant elevated protein expression of CCR3 and CCR5 in both $CD3^+$ and $CD14^+$ cells at t=0 compared with t=180 (FIG. 4A-D). Triple staining for CD3 or CD14 with CCR3 and CCR5 showed an increased chemokine receptor expression in the $CD3^+$ population (3.1% triple positive cells at t=0 vs. 2.3% at t=180; P=0.007) and even more prominently so in the $CD14^+$ cells (32.1% vs. 5.1% at t=0 and t=180, respectively; P<0.001). An identical pattern was seen for the percentage of $CCR3^+$ and $CCR5^+$ cells as well as of the combined $CCR3^+/CCR5^+$ cells in the total PBMC population (FIG. 4G-I).

To assess whether the reduced gene expression pattern at baseline were caused by transient shifts in the leukocyte distribution profile, the total percentage of $CD14^+$ (monocytes) and $CD3^+$ cells (T-lymphocytes) in the PBMCs were monitored. Monocyte counts were not different between the two time points, whereas $CD3^+$ cells were slightly decreased at t=0 (54.2 vs. 66.6%; P=0.01)(FIG. 8A). A further study revealed no differences in the expression ratio of CCR2: CX3CR1, a measure of monocyte subset distribution, in PBMCs as well. We did however observe significantly elevated expression levels of HNP-3, a selective neutrophil marker, at t=0, pointing to an enhanced release of neutrophils during UAP (FIG. 8B). Conceivably, the observed changes in chemokine receptor expression at t=0 may at least partly be attributed to the increased neutrophil counts. In contrast to chemokine plasma levels, no differences in expression level were seen for chemokine receptors between stabilised and refractory patients at t=0 (data not shown).

PBMC Stimulation Assay.

In part however, the chemokine receptor down-regulation may reflect a feedback response on the immunomodulator burst after UAP. To verify if the observed expressional regulation of CCR1, CCR3, CCR4 and CCR5 in PBMCs is related to the elevated CCL5 and CCL18 levels during ischemic events, PBMCs were stimulated with rCCL5 and/ or sCCL18. After 6 hours of stimulation, no differential effect was observed on CCR1, CCR4 and CCR5 mRNA expression. In sharp contrast however, sCCL18 caused a dramatic down-regulation in CCR3 expression, and this effect was further amplified by co-incubation with rCCL5 (P<0.01, FIG. 5A-D). Therefore, the down-regulation of CCR3 mRNA in PBMCs observed in vivo could be caused by the increased levels of CCL18. The down-regulation of CCR1, CCR4 and CCR5 in vivo might well be regulated by ligands other than CCL5 and CCL18.

Discussion

Of all chemokines tested, only CCL5 and CCL18 levels were, independent of other inflammatory markers and sCD40L, seen to be transiently elevated in refractory versus stabilised patients at baseline and to decline within 6 months after onset of the UAP symptoms. These phenomena were accompanied by a sharp, probably CCL18 induced, decrease in mRNA expression of the cognate chemokine receptors CCR3 and CCR5 in PBMCs at day 0 versus day 180. Concomitantly CCR3 and CCR5 surface expression was found to be increased at baseline, possibly reflecting a rapid receptor exposure by PBMCs during ischemic symptoms. Both CCL5 and CCL18 also show predictive features regarding clinical outcome.

The multiplex panel contained various chemokines, which have previously been linked with atherosclerosis or cardiovascular disease, such as CCL2, CCL5, CCL11, CXCL8 and CXCL105. CCL5 and CCL18 were the only two chemokines that were differentially regulated at baseline between refractory and stabilised patients. Refractory patients had severe sustained ischemic complaints despite anti-anginal medication warranting coronary angiography with or without percutaneous coronary intervention. Therefore, while the levels of other chemokines that have been implicated in CVD were relatively unaltered and while refractory patients do not generally differ from stabilised in the extent of general systemic inflammation, CCL5 and CCL18 might be exclusive chemokine markers of ischemia severity in patients with UAP.

CCL5 and CCL18 were selected for further temporal analysis for a 180 days follow up. As previously mentioned, the role of CCL5 as an inflammatory mediator in cardiovascular disease is widely recognized, and CCL5 levels were indeed seen to be raised in patients with acute coronary syndromes. However, these studies examined CCL5 levels at hospitalization and, with one single exception, did not include a prospective study design. Only Nomura et al. showed a drop in CCL5 levels 30 days in UAP patients after PCI, to levels comparable with the 180 day levels in our study. Data in this example extend this observation, as they demonstrate that the decline in CCL5 levels is not a consequence of PCI, but an intrinsic feature of stabilized UAP patients. Although data on CCL5 reference levels are still lacking, CCL5 at 2 and 180 days post inclusion was very comparable to values reported in healthy controls by Parissis et al., suggesting that CCL5 levels had returned to baseline within 2 days after onset of the ischemic symptoms.

To gain further insight on the contribution of activated platelets to the CCL5 peak levels, a temporal assessment of sCD40L22 was performed. Significantly elevated levels of sCD40L at baseline were observed, which is in concordance with earlier studies and reflective of the enhanced platelet activation status in UAP. However, the observed progressive decline in sCD40L levels at t=2 and t=180 after UAP has never been documented in patients with UAP and may illustrate the rapid restoration of sCD40L homeostasis after UAP. Furthermore, t=0 and t=2 levels correlated with CCL5 levels, suggesting that activated platelets may, directly or indirectly, be a major source of CCL5. Apart from its massive secretion by activated platelets, elevated CCL5 levels during UAP could also arise from activated T-lymphocytes and as a result of altered homeostasis in the ischemic tissue distal to the occlusion. Since Rothenbacher et al. observed reduced CCL5 levels in patients with stable coronary heart disease compared to controls, acute inflammation per se can unlikely be held responsible for the transient increase in CCL5 during UAP27. This is underscored by findings in this example, as a down-regulation of CCL5 mRNA expression in PBMCs at baseline was observed, compared to 180 days after onset of the ischemia. Whether the increased response in refractory patients reflects a more extensive platelet (or T-cell) activation or a higher capacity of platelets and T-cells to elaborate CCL5 remains to be determined.

Interestingly, CCL18 has not yet been associated with cardiovascular disorders in patient cohorts. CCL18 is present at high levels in blood and it is produced by antigen presenting cells and by eosinophils. It is thought to act in the primary immune response functioning as an attractant for T-cells, B lymphocytes and monocytes 17. As previously mentioned however, its receptor has not been identified, albeit that CCL18 was reported to function as a neutral CCR3 antagonist. Evidence on a direct role of CCL18 in cardiovascular disease is not conclusive and is limited to two descriptive studies documenting CCL18 expression in atherosclerotic plaques and in particular at sites of reduced stability. It is shown in this example that CCL18 plasma levels are increased in UAP patients and even more so in patients with refractory symptoms. CCL18 elevation is sustained transient but levels are lowered after 180 days. The actual source of the persistent CCL18 increase after UAP is less clear. CCL18 expression was down-regulated in PBMCs at baseline, disqualifying abundant production by these cells as major source of plasma CCL18. Conceivably, plasma levels may reflect a release from CCL18 containing vulnerable plaques. CCL18 levels were negatively correlated with sCD40L levels, possibly pointing to a negative feedback response upon platelet activation. Further research will have to clarify its role in acute coronary syndromes.

It has been suggested that several chemokines can act in the pathogenesis of non-infarcted ischemic cardiomyopathy, as the prevailing reactive oxygen generation and hypoxia in the ischemic tissue will induce a chemokine response. Illustratively, MCP-1 was seen to be up-regulated in the myocardium at least 7 days after ischemia in mice and associated with interstitial fibrosis and left ventricular dysfunction in absence of myocardial infarction. CCL18 levels persisted at a high level for at least two days as well, and given its capacity to activate fibroblasts and increase collagen production, it is tempting to propose a similar role of CCL18 in injury healing. It may not only modulate the attraction of leukocyte subsets but, CCL18 may also play a facilatory role in bone-marrow haematopoietic stem cell function. Therefore, elevated CCL18 levels could contribute in the inflammatory response but also in progenitor cell mobilisation towards areas of myocardial ischemia in anticipation of the myocardial repair process.

To further stress the role of CCL5 and CCL 18 in the pathophysiology of myocardial ischemia, a significant increase in surface exposure of CCR3 and CCR5 by $CD3^+$ T-cells and $CD14^+$ monocytes and a paradoxical mRNA down-regulation of CCR1, CCR3, CCR4 and CCR5 at baseline was observed. This is an intriguing and counterintuitive observation, albeit that this was not the first observation of such a discrepancy between protein and mRNA chemokine receptor expression in PBMCs from UAP patients. In fact a similar but opposite effect for CXCR4 was previously reported, i.e. down-regulation at the protein but up-regulation at the mRNA level in UAP compared with healthy control subjects, while levels of its ligand CXCL12 were lowered in patients with UAP compared to controls. The rapid increase in surface protein exposure may result from acute mobilisation of intracellular receptors in response to enhanced plasma levels of the cognate ligands or of other actors that are released in unstable angina. The relative mRNA down-regulation of chemokine receptors in PBMCs may partly reflect a shifted leukocyte profile in UAP with a rapid mobilisation of $HNP-3^+$ neutrophils as judged from the enhanced HNP-3 expression in PBMC mRNA at t=0, and a minor decrease in $CD3^+$ cells, while total $CD14^+$ levels remained unaffected. Partly however it may also be attributable to a negative feedback response to normalize exposed receptor levels as appears from our in vitro CCL18 regulation studies (FIG. 5). The transcriptional feedback may be effected in direct response to exposure of the surface receptors to CCL18, as CCR3 mRNA levels were dramatically decreased after exposure to sCCL18, thus identifying a new modulatory role of CCL18 in cardiac ischemia.

Examination of CCL5 and CCL18 quartile distribution shows a clearcut relation with the occurrence of refractory symptoms. Furthermore, upper quartile levels also correlated with future cardiovascular events and revascularisation procedures, whereas sCD40L and CRP, which have been shown to have strong prognostic power in other studies, did not at this cohort size. Given the major cellular sources of CCL5 and CCL18, activated platelets and ischemic tissue, the increased levels in refractory UAP may reflect a more pronounced thrombosis and ischemia related induction in these patients. Whether or not it is causal in the refractory disease progression still remains to be clarified. Regarding the prognostic capacities of CCL5 and CCL18, the sensitivity and specificity of the upper quartile levels of the chemokines separately did not exceed 80%. Combining the upper two quartiles of both chemokines yielded a viable specificity of 90.3%, which thereby quite effectively rules out refractory symptoms for low CCL5 and CCL18 levels. However, although CCL5 and CCL18 may have potential as independent prospective biomarkers for disease, the correlations observed between these chemokines and clinical severity of the symptoms as well as various follow-up parameters, albeit very significant, are currently not strong enough on its own. Therefore, the determination of plasma CCL5 and CCL18 levels, in combination with other clinical diagnostic parameters, could add prognostic features to the evaluation of patients with UAP.

A few issues and limitations of this study should be noted. First, the set up principally precluded studying control levels of these chemokines before UAP. Nevertheless it is believed that, as prospective analysis were performed in the same patients, conclusions on the temporal profile of CCL5 and CCL18 are justified. As all patients are largely symptom free at 180 days post UAP, it may be safely assumed that the latter values will approach the pre UAP levels of CAD patients. Second, it has recently been shown that statins can influence chemokine serum levels as well as chemokine receptor expression on PBMCs. As it was a fortunate circumstance that cohort sampling had taken place when statin therapy just began to emerge, only 8.2% of the patients of this cohort was on statin therapy. Since the data were corrected for this minor statin use, it is believed that the results in this example are not biased by statin therapy. Finally, the multiplex panel also comprised chemokines which have previously been linked to atherosclerosis or myocardial ischemia, including CCL2, CCL3, CXCL8 and CXCL1021, 39, 40. In this study, refractory unstable angina patients did not show significant differences for these chemokines nor for the other immunomodulators that had been assayed. These cytokines have thus not been selected for further temporal analysis but it cannot, a priori be ruled out that these cytokines may affect unstable angina pectoris and myocardial ischemia.

Furthermore, preliminary data in atherosclerosis prone $ApoE^{-/-}$ mice that already had developed collar induced carotid artery plaques showed that a 3 week intraperitoneal administration regimen of recombinant CCL18 aggravated lesion progression by a significant 50% (FIG. 9), suggesting that CCL18 may not only be a promising marker of cardiovascular disease but also a valid candidate for therapeutic intervention in cardiovascular disease.

To conclude, CCL5 and particularly CCL18 were identified as relevant chemokines in UAP. Whether they play a causative role in the pathogenesis or are more indirectly involved via other mechanisms, if these markers harbour any further diagnostic potential and if they are suitable therapeutic targets, needs to be addressed in future studies.

Example 3: CCL3 (MIP-1α) Levels are Elevated During Acute Coronary Syndromes and Show Strong Prognostic Power for Future Ischemic Events Methods Patient Cohorts Mission.

Study populations were compiled from the MISSION! intervention study 12. The AMI patient group consisted of 44 patients (54.5% male; mean age 61.8±11.6 years) diagnosed with AMI on the basis of ECG and clinical chemical parameters (elevated troponin and creatine kinase levels). The control group represented 22 non-symptomatic age and sex matched subjects (54.5% male; mean age 61.7±12.8), not suffering from manifest coronary artery disease (Table 5). Baseline blood samples of AMI patients were taken within 2 hours after hospitalization and within 6 hours upon onset of AMI. Patients suffering from autoimmune disease, malignancies, chronic inflammatory diseases as rheumatoid arthritis or receiving immunosuppressant or chemotherapy were excluded from the study. This study was approved by the local ethics committee and all patients and healthy volunteers gave informed consent before being recruited. The investigation conformed to the principles outlined in the Helsinki Declaration.

APRAIS.

Plasma samples of patients with unstable angina, derived from the well defined APRAIS (Acute Phase Reaction and Ischemic Syndromes) study, were used to determine circulating CCL3 levels 13. In brief, 54 patients who were admitted to the emergency department of the Leiden University Medical Center between March and September 1995 with unstable angina pectoris Braunwald class IIIB were included and followed for up to 18 months. Venous blood samples were obtained on admission (t=0) after 2 (t=2) and 180 days after admission (t=180), centrifuged and plasma aliquots were stored at −80° C. until further analysis. All patients had received standard medical therapy, i.e. aspirin 300 mg orally, nitro-glycerine intravenously and heparin infusion based titrated to the activated partial thromboplastin time. All subjects gave written informed consent and the study protocol was approved by the Ethics Committee of the Leiden University Medical Center.

Multiplex Chemokine Assay.

Circulating chemokines levels of CCL2, CCL3, CCL5, CCL11, CCL17, CCL18, CCL22, CXCL8, CXCL9, and CXCL10 as well as four reference cytokines were determined in the MISSION! cohort, as well as CCL3 levels in the APRAIS cohort, by using a highly sensitive fluorescent microsphere based readout as described. Briefly, plasma samples were filtered and subsequently diluted with 10% normal rat and mouse serum (Rockland, Gilvertsville, Pa.) to block residual non-specific antibody binding. 1000 microspheres were added per chemokine (10 µl/well) in a total volume of 60 µl, together with standard and blank samples, and the suspension incubated for 1 hour in a 96 well filter plate at room temperature (RT). Then, 10 µl of biotinylated antibody mix (16.5 µg/ml) was added and incubated for 1 hour at RT. After washing with PBS-1% BSA-0.5% TWEEN® 20 [polyethylene glycol sorbitan monolaurate], beads were incubated with 50 ng/well streptavidin R-phycoerythrin (BD Biosciences, San Diego, Calif.) for 10 minutes. Finally, beads were washed again with PBS-1% BSA-0.5% TWEEN® 20 [polyethylene glycol sorbitan monolaurate], and the fluorescence intensity was measured in a final volume of 100 µl high-performance ELISA buffer (Sanquin, Amsterdam, the Netherlands). Measurements and data analysis were performed with the Bio-Plex Suspension Array system in combination with the Bio-Plex Manager software version 3.0 (Bio-Rad laboratories, Hercules, Calif.).

Murine Myocardial Infarction.

Mice were anaesthetized and artificially ventilated with a mixture of oxygen and N2O [1:2 (vol/vol)] using a rodent ventilator (Harvard Apparatus, Holliston, Mass.) to which 2-2.5% isoflurane (Abbott Laboratories, Hoofddorp, the Netherlands) was added for anesthesia. Myocardial infarction was induced by permanent ligation of the proximal left anterior descending coronary artery with a sterile 7/0 silk suture (Ethicon, Johnson & Johnson, Amersfoort, the Netherlands). Three hours after ligation the mice were sacrificed, PBMCs and spleens were isolated for flow cytometric analysis and plasma was harvested for chemokine detection. All animal procedures were approved by the Animal Ethics Committee of Leiden University.

ELISA and Other Assays.

Human as well as murine CCL3 levels (Biosource, Carlsbad, Calif.), murine CXCL10 (R&D systems, Minneapolis, Minn.) and murine IL-6 (eBioscience, San Diego, Calif.) were determined by sandwich Elisa assays as described by the manufacturers protocol. Baseline inflammatory parameters in the APRAIS cohort, such as C-reactive protein, fibrinogen and erythrocyte sedimentation rate (ESR), were determined as described previously 13. Soluble CD40 ligand (sCD40L) was determined via a highly sensitive immunoassay (Quantakine HS, R&D Systems, Minneapolis, Minn.).

Flow Cytometry.

PBMCs were isolated from whole blood by ablation of the erythrocytes. Splenocytes were isolated by squeezing spleens through a 70 µm cell strainer (BD falcon, BD Biosciences, San Jose, Calif.). After collection total blood cells and splenocytes were incubated with erythrocytes lysis buffer for 5 minutes on ice. Cells were centrifuged for 5 minutes and resuspended in lysis buffer. Residual erythrocytes were lysed by 5 minute incubation on ice. Cells were washed twice with PBS and counted. Consequently cells were stained for CD4, CCR3, CCR5 (BD Biosciences), CD8, F4/80 (eBioscience) and CXCR3 (US biological, Swampscott, Mass.) surface markers by adding 0.25 µg antibody per sample. After 45 minutes incubation on ice, cells were washed with PBS and subsequently analyzed by flow cytometry (FACScalibur, BD biosciences).

Statistical Methods.

Statistical analysis was performed using SPSS version 13.0 (SPSS, Chicago, Ill.) All values are expressed as mean E standard error of mean. Differences in risk factor distribution between the control and the AMI group were analyzed with a Fishers Exact probability test. Chemokine data were tested for normal distribution by use of a Kolmogorov-Smirnov analysis. Non-Gaussian distributed data were analyzed by a Mann-Whitney U test, whereas normally distributed variables were analyzed by Student's t-test. Correlation analysis with inflammatory parameters was performed by Spearman's rank correlation test. Covariate adjustment for risk factors was performed by a univariate linear regression test. Quartile distribution of CCL3 was assessed and used for Chi-Square testing to associate elevated levels of CCL3 with future cardiovascular events. A P-value<0.05 was considered significant.

Results

Mission Patient Statistics.

Two sub-cohorts were compiled at a 2:1 ratio as a pilot study revealed that the standard deviation in cytokine levels in the AMI population was on average 1.5 fold higher than that of the control subjects. AMI and control sub-cohorts were matched for gender, age and risk factors known to be associated with inflammatory status (type 2 diabetes mellitus, hypertension and hyperlipidemia). The AMI cohort encompassed a higher fraction of smokers and ex-smokers than the control cohort (56.8% in AMI compared to 22.7% in controls; P=0.01; Table 5). Therefore, all chemokine values were adjusted for smoking by univariate analysis. All proteins were all well within detectable range of the used assay.

TABLE 5

MISSION! Patient Characteristics

|  | Controls | Acute Myocardial Infarction | P-value |
|---|---|---|---|
| Age (years) | 61.7 ± 2.6 | 61.8 ± 1.8 | 0.96 |
| Male/Female | 12/10 | 24/20 | 1.00 |
| Diabetes Mellitus | 3 (13.6%) | 6 (13.6%) | 1.00 |
| Hypertension | 8 (36.3%) | 11 (25%) | 0.39 |
| Total Cholesterol | 5.6 ± 0.3 mmol/L | 6.0 ± 0.1 mmol/L | 0.14 |
| Smoking | 5 (22.7%) | 25 (56.8%)*; | 0.01 |
|  | 4 (18.1%) ex-smokers | 4 (9.1%) ex-smokers |  |

TABLE 6

APRAIS CCL3 t = 0 quartile levels as determined by multiplex

| Quartiles | CCL3 (pg/ml) |
|---|---|
| 1 | <41 |
| 2 | >41 and <53 |
| 3 | >53 and <83 |
| 4 | >83 |

Chemokines.

Plasma levels of the CC chemokines CCL3 (39.8 pg/ml, 21.3-50.3 IQR in controls compared to 47.8 pg/ml, 39.6-67.2 IQR in AMI; P=0.01: FIG. 13A) and CCL5 (13.4 ng/ml, 6.4-29.2 IQR in controls compared to 33.3 ng/ml, 19.1-45.3 in AMI; P=0.001: FIG. 14B) were significantly up-regulated in AMI compared to control patients (Table 7). After correction for cardiovascular risk factors CCL3 and CCL5 remained significantly elevated during AMI (P=0.025 and P=0.006 respectively). Of the CXC chemokines only CXCL8 (4.2±0.50 pg/ml in controls compared to 6.8±0.56 in AMI; P=0.01; FIG. 13C) was significantly up-regulated, while CXCL10 (255.1±47.2 pg/ml in control vs. 162.6±20.3 in AMI; P=0.002: FIG. 13D) was down-regulated in AMI compared to controls. After covariate adjustment both CXCL8 and CXCL10 remained 'significantly changed (P=0.02 and P=0.04 respectively). All other measured chemokines were not differentially regulated during AMI (Table 7).

TABLE 7

Mean Cytokine and Chemokine values

|  | Control | AMI |  | P | P* |
|---|---|---|---|---|---|
| IL-2 | 0.07 ± 0.06 pg/ml | 0.65 ± 0.28 pg/ml | ↑ | 0.003 | 0.047 |
| IL-6 | 9.8 ± 4.1 pg/ml | 23.8 ± 8.0 pg/ml | ↑ | 0.04 | 0.07 |
| TNFα | 0.6 pg/ml, (0-1.6) | 1.4 pg/ml, (0.5-2.4) | ↑ | 0.03 | 0.01 |
| sICAM-1 | 476 ± 80.7 ng/ml | 714 ± 50.0 ng/ml | ↑ | 0.045 | <0.001 |
| CCL2 | 305 ± 81 pg/ml | 522 ± 77 pg/ml | = | 0.08 | 0.14 |
| CCL3 | 49.8 pg/ml (21.3-50.6) | 47.7 pg/ml, (39.6-67.2) | ↑ | 0.02 | 0.025 |
| CCL5 | 13.4 ng/ml (6.4-29.2) | 33.3 ng/ml, (19.8-45.3) | ↑ | 0.001 | 0.006 |
| CCL11 | 15.9 pg/ml, (12.7-22.0) | 21.2 pg/ml, (13.6-29.8) | = | 0.27 | 0.33 |
| CCL17 | 16.4 pg/ml, (10.5-21.4) | 16.6 pg/ml, (8.6-28.9) | = | 0.46 | 0.26 |
| CCL18 | 555 ± 186 ng/ml | 681 ± 160 ng/ml | = | 0.18 | 0.85 |
| CCL22 | 356 pg/ml, (264-409) | 371 pg/ml, (296-549) | = | 0.11 | 0.08 |
| CXCL8 | 3.5 pg/ml, (1.9-4.3) | 5.1 pg/ml, (3.5-7.4) | ↑ | 0.004 | 0.02 |
| CXCL9 | 163 ± 51 pg/ml | 155 ± 25 pg/ml | = | 0.16 | 0.87 |
| CXCL10 | 255 ± 47.4 pg/ml | 120 ± 20.3 pg/ml | ↓ | 0.001 | 0.004 |

Reference Panel.

As a control for the validity of the multiplex assay a panel of reference cytokines and cell adhesion markers was included in the analysis. In compliance with previous findings plasma levels of IL-2 (0.07±0.06 pg/ml in controls vs. 0.65±0.28 in AMI; P=0.003), TNF-α (1.05±0.32 pg/ml in controls vs. 2.4±0.72 in AMI; P=0.03), sICAM-1 (476.1±80.7 ng/ml in controls vs. 713.0±49.9 in AMI; P=0.04) and IL-6 (9.8±4.1 in controls compared to 23.7±8.0 pg/ml in AMI; P=0.04) were significantly elevated in AMI patients (Table 6). Other general inflammation markers as IL-1α, IFN-γ and sVCAM-1 remained unchanged (data not shown), thereby showing that the AMI patient cohort was not enriched in subjects with a general hyperinflammatory status.

Reference (IL-2, IL-6, TNF-α and sICAM-1) and chemokine panel of measured parameters containing P value and corrected P value (P*) after adjustment for smoking. Values are expressed as mean±SEM or median with IQR when appropriate.

APRAIS.

To verify this observation CCL3 levels of the MISSION! cohort were compared with those of the APRAIS cohort as described earlier refer to Example 2. Inter-study analysis showed that patients with UAP also displayed similar increased CCL3 plasma levels compared to the MISSION! AMI patients (FIG. 11A). Next, a temporal analysis of circulating CCL3 levels was performed in the APRAIS cohort of patients with unstable angina pectoris. Plasma samples from baseline (t=0), t=2 and t=180, as analyzed by ELISA, revealed a significant decrease of CCL3 levels at t=180 compared with t=0 as well as t=2 (t=0 7.57 pg/ml; t=2 6.49 pg/ml; t=180 4.31 pg/ml, P<0.001) (FIG. 11B). Although absolute CCL3 plasma levels detected by ELISA were lower, comparison of both techniques revealed a highly significant correlation (R=0.92, P<0.001). Next, it was sought to assess if CCL3 plasma levels had any potential to predict clinical outcome. Given the cohort size, multiplex CCL3 t=0 plasma levels were therefore categorized into quartiles and analyzed for correlation with the occurrence of ischemic symptoms during or immediately after hospitalisation and/or acute coronary syndromes (for quartile distribution, see Table 6). Upper quartile levels of CCL3 were highly predictive for the occurrence of acute coronary syndromes during follow-up (Likelihood ratio 11.52; P<0.01) and recurrent unstable angina pectoris during hospitalisation (Likelihood ratio 14.63; P<0.01) (FIG. 12A, B). Cardiac death during follow-up also showed a significant association, although less strong (Likelihood ratio 7.92; P<0.05) (data not shown). Finally, CCL3 did not correlate with any of the inflammatory parameters (data not shown). However, sCD40L levels revealed a significant negative correlation with CCL3 levels (R=-0.44; P=0.001), suggestive of a feedback response upon platelet activation.

Unlike CCL5 and CCL18, CCL3 levels was not predictive of a refractory nature of UAP (early stage) but highly significantly so of more mid term events occurring within 180 days after UAP.

Murine Myocardial Infarction.

Figure 14C:
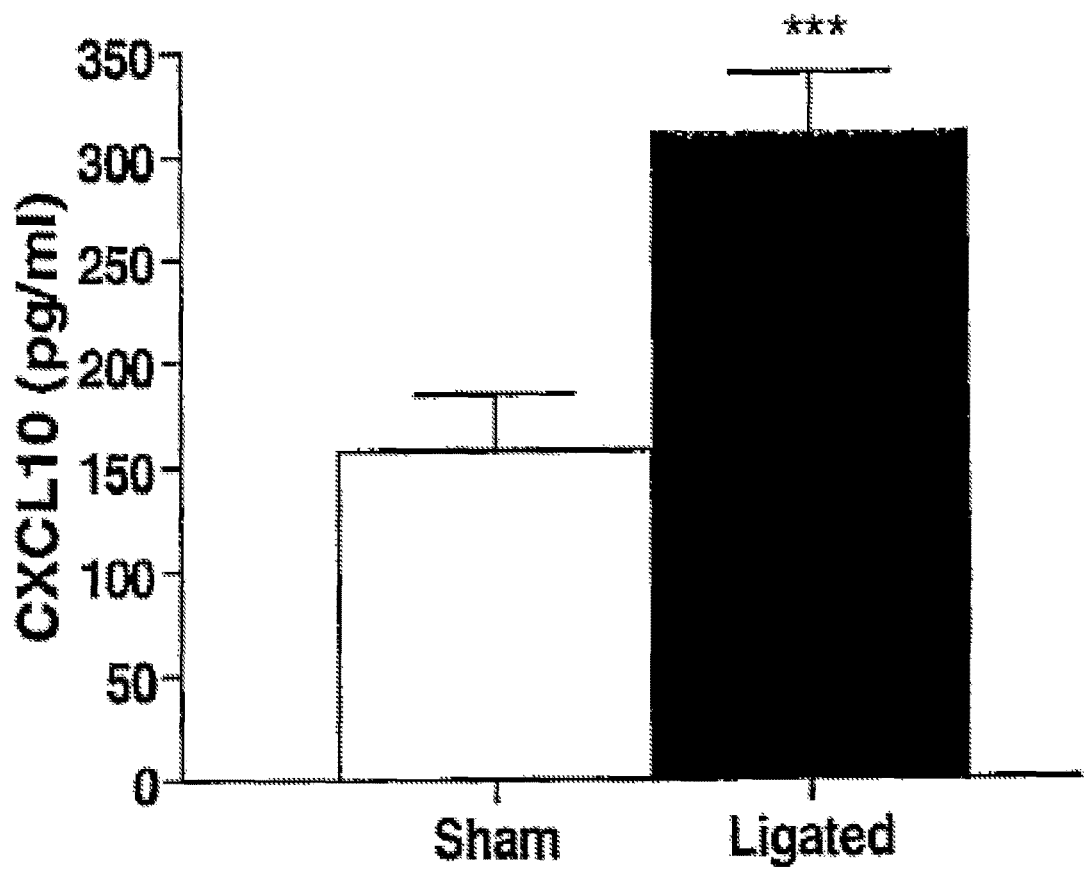

The obtained results in humans suggest an important role for CCL3 in ischemic myocardial injury. To ascertain whether the enhanced chemokines were ischemia related myocardial infarction experiments in mice were performed. Since the chemokines CCL5 and CXCL8 have been extensively studied regarding atherothrombosis and AMI CCL3 and CXCL10 were further investigated. To induce acute myocardial infarction the left anterior descending coronary artery was ligated in C57B16 mice. CCL3 levels were, in concurrence with the earlier MISSION! findings, significantly elevated after AMI (33.2±1.5 vs. 76.4±37.4 pg/ml in ligated animals; P=0.02) (FIG. 14B). As a control for the AMI model, levels of the ischemia related cytokine IL-6 were measured 16, 17. IL-6 levels were significantly up-regulated after ligation (0.67±0.26 in sham vs. 1.34±0.46 ng/ml in ligated animals; P=0.007, FIG. 14A). Surprisingly the levels of CXCL10 were, opposed to the MISSION! findings, significantly enhanced after AMI (157.3±64.8 in sham operated compared to 310.6±86.6 pg/ml in ligated animals; P=0.03) (FIG. 14C). In addition PBMCs were harvested and analyzed for chemokine receptor expression on different cell subsets. As expected, the total T-cell population was enhanced in the circulation after ligation (14.1±3.8% in controls vs. 32.8±14.4% in ligated mice; P=0.038) while no effects were seen on splenic T-cells (P=0.9, FIGS. 15A and D respectively). Moreover the number of both circulating as well as splenic macrophages was not regulated by ischemic injury (data not shown). More extensive analysis of the T-cell population revealed a specific enrichment of CCR5$^+$ T-cells (8.0±2.0% in controls compared to 11.4±1.4% in ligated animals; P=0.02) (FIG. 15B). The enrichment in circulatory CCR5$^+$ T-cells was accompanied by a reduction in splenic CCR5$^+$ T-cells (19.95±0.5% vs. 14.1±3.1%; P=0.004) (FIG. 15E). CCR3 is the known receptor for the CCL3 related chemokine CCL4. As CCL3 and CCL4 are usually co-regulated PBMCs and splenocytes were also analyzed for CCR3 expression. The numbers of circulating CCR3$^+$ T-cells was very low. Analysis showed a slight, albeit not significant (P=0.24), increase in circulating CCR3$^+$ T-cells (data not shown). No differences in splenic CCR3$^+$ T-cells were evident (data not shown). Taken together these data suggest a CCL3 specific migration of T-cells from the secondary lymphoid organs towards the site of ischemic injury. In addition expression of the CXC chemokine receptor CXCR3 was determined on the circulating T-cells as well. In concurrence with the enhanced CXCL10 levels, the number of circulating CXCR3$^+$ T-cells was significantly increased after LAD ligation (29.1±1.9% vs. 43.5±5.7%; P=0.04) (FIG. 15C). However no effects on CXCR3$^+$ splenic T-cells were apparent (P=0.78) (FIG. 15F).

Preliminary data suggest that CCL3 levels not only are predictive of the risk of future cardiovascular events, but may also be causally implicated in disease development as atherosclerotic plaque growth in the aortic sinus of hyperlipidemic LDL receptor knockout mice with a leukocyte deficiency in CCL3 is significantly lower (-60%) than that in mice with normal leukocyte production of CCL3 (FIG. 10).

Example 4: Causal Role for Neutrophils in the Development of Atherosclerosis

Materials and Methods

Animals.

LDLr$^{-/-}$ mice were obtained from the local animal breeding facility. Mice were maintained on sterilized regular chow (RM3; Special Diet Services, Essex, U.K.). Drinking water was supplied with antibiotics (83 mg/L ciprofloxacin and 67 mg/L polymyxin B sulfate) and 6.5 g/L sucrose and was provided ad libitum. Animal experiments were performed at the animal facilities of the Gorlaeus laboratories of the Leiden University. All experimental protocols were approved by the ethics committee for animal experiments of Leiden University.

Temporal Expression Profile.

Male LDLr$^{-/-}$ mice were fed a Western type diet containing 0.25% cholesterol and 15% cacaobutter (Special Diet Services, Sussex, UK) two weeks prior to surgery and throughout the experiment. To determine gene expression levels in (n=20) mouse plaques, atherosclerotic carotid artery lesions were induced by perivascular collar placement as described previously 1. Mice were anaesthetized by subcutaneous injection of ketamine (60 mg/kg, Eurovet Animal Health, Bladel, The Netherlands), fentanyl citrate and fluanisone (1.26 mg/kg and 2 mg/kg respectively, Janssen Animal Health, Sauderton, UK). From 0 to 8 weeks after collar placement every two weeks a subset of 4 mice was sacrificed. The animals were anaesthetized as described above and perfused through the left cardiac ventricle with PBS and exsanguinated by femoral artery transsection. Subsequently, both common carotid arteries were removed and snap-frozen in liquid nitrogen for optimal RNA preservation. The specimens were stored at −80° C. until further use.

RNA Isolation.

Two or three carotids were pooled per sample and homogenized by grounding in liquid nitrogen with a pestle. Total RNA was extracted from the tissue using Trizol reagent according to manufacturer's instructions (Invitrogen, Breda, The Netherlands). RNA was reverse transcribed using M-MuLV reverse transcriptase (RevertAid, MBI Fermentas, Leon-Roth) and used for quantitative analysis of gene expression with an ABI PRISM 7700 Taqman apparatus (Applied Biosystems, Foster City, Calif.) as described previously, using murine hypoxanthine phosphoribosyltransferase (HPRT) and cyclophilin A (CypA) as standard housekeeping genes (Table 8).

Bone Marrow Transplantation.

To induce bone marrow aplasia, male LDLr$^{-/-}$ recipient mice were exposed to a single dose of 9 Gy (0.19 Gy/min, 200 kV, 4 mA) total body irradiation using an Andrex Smart 225 Röntgen source (YXLON International) with a 6-mm aluminum filter 1 day before transplantation. Bone marrow was isolated from male CCL3$^{-/-}$ or littermates by flushing the femurs and tibias. Irradiated recipients received 0.5×10$^7$ bone marrow cells by tail vein injection and were allowed to recover for 6 weeks. Animals were placed on a western type diet containing 0.25% cholesterol and 15% cacao butter (SDS) diet for 12 weeks and subsequently sacrificed. Twenty four hours prior to sacrifice a subset of animals were injected intraperitoneally with lipopolysaccharide (LPS) (*Salmonella minnesota* R595 (Re) (List Biological Laboratories Inc., Campbell, Calif.)). Plasma levels of CCL3 were determined by sandwich Elisa (Biosource, Carlsbad, Calif., according to the manufacturer's protocol) to confirm impaired CCL3 production from leukocytes.

Histological Analysis.

Cryostat sections of the aortic root (10 μm) were collected and stained with Oil-red-O. Lesion size was determined in 5 sections of the aortic valve leaflet area. Corresponding sections on separate slides were stained immunohistochemically with an antibody directed against a macrophage specific antigen (MOMA-2, monoclonal rat IgG2b, dilution 1:50; Serotec, Oxford, UK). Goat anti-rat IgG-AP (dilution 1:100; Sigma, St. Louis, Mo.) was used as secondary antibody and NBT-BCIP (Dako, Glostrup, Denmark) as enzyme substrates. Masson's trichrome staining (Sigma, St. Louis, Mo.) was used to visualize collagen (blue staining). Neutrophils were visualized by Naphtol AS-D Chloroacetate Esterase stain according to the manufacturer's protocol (Sigma).

Macrophage Stimulation.

Serum deprived RAW264.7 macrophages were stimulated with 10 μg/ml ox-LDL or 1 ng/ml LPS for 24 hours. Total RNA was isolated for real time PCR to assess CCL3 expression. Serum deprived RAW 264.7 macrophages were stimulated with recombinant CCL3 (10 or 100 ng/ml) for 24 hours. Subsequently [3H]-Thimidine (1 μCi/well, specific activity 24 Ci/mmol; Amersham Biosciences, The Netherlands) was added to each well and cells were allowed to proliferate for another 24 hours. Cells were rinsed twice with cold PBS and subsequently lysed with 0.1M NaOH. The amount of [3H]-thymidine incorporation was measured using a liquid scintillation analyzer (Tri-Garb 2900R).

Cyclophosphamide Induced Neutropenia.

Female CCL3$^{-/-}$ mice or WT control received an intraperitoneal (i.p) injection of cyclophosphamide (6 mg/mouse) to deplete blood neutrophils as described previously. Blood samples were taken via the tail vein regularly and blood cell differentiation was determined on a Sysmex cell differentiation apparatus (Goffin Meyvis, Etten-Leur, Nederland).

In Vivo Chemotaxis.

Female CCL3$^{-/-}$ mice or WT control received an i.p. injection of 500 ng recombinant KC (Peprotech, Rocky Hill, N.J.) or PBS. Two hours later blood and peritoneal cells were isolated and analyzed for neutrophil composition by flow cytometry.

Flow Cytometry.

Peritoneal leukocytes were harvested by peritoneal cavity lavage with PBS. Crude peripheral blood mononuclear cells (PBMC) and peritoneal leukocytes were incubated at 4° C. with erythrocyte lysis buffer (155 mM NH4CL in 10 mM Tris/HCL, pH 7.2) for 5 minutes. Cells were centrifuged for 5 minutes at 1500 rpm, resuspended in lysis buffer to remove residual erythrocytes. Cells were washed twice with PBS. Cell suspensions were incubated with 1% normal mouse serum in PBS and stained for the surface markers CD11b, GR1 and CD71 (eBioscience, San Diego, Calif.) at a concentration of 0.25 μg Ab/200,000 cells. Subsequently cells were subjected to flow cytometric analysis (FACSCalibur, BD Biosciences, San Diego, Calif.). FACS data were analyzed with CELLQuest software (BD Biosciences).

Statistical Analysis.

Data are expressed as mean±SEM. A 2-tailed Student's t-test was used to compare individual groups, while multiple groups were compared with a one-way ANOVA and a subsequent Student-Newman-Keuls multiple comparisons test. Non-parametric data were analyzed using a Mann-Whitney U test. A level of P<0.05 was considered significant.

Results

Temporal expression analysis of atherosclerotic lesions in LDLr$^{-/-}$ mice showed a clearcut, transient upregulation of CCL3 in initial plaques (2 weeks after collar placement). At more advanced stages of lesion progression CCL3 is returning to its original level. This expression is initially accompanied by increased expression of macrophage marker CD68 of which its levels remain high at later time points. The expression of CD36 is somewhat delayed as compared to CD68 and CCL3 (FIG. 16). The expression profiles suggest that CCL3 may be involved in the critical recruitment of inflammatory cells to atherosclerotic lesion sites. In vitro exposure of RAW 264.7 macrophages to ox-LDL leads to a moderate induction of CCL3 expression, while the TLR4 ligand LPS strongly induces MIP1α at mRNA level (FIG. 17).

Figure 17C:
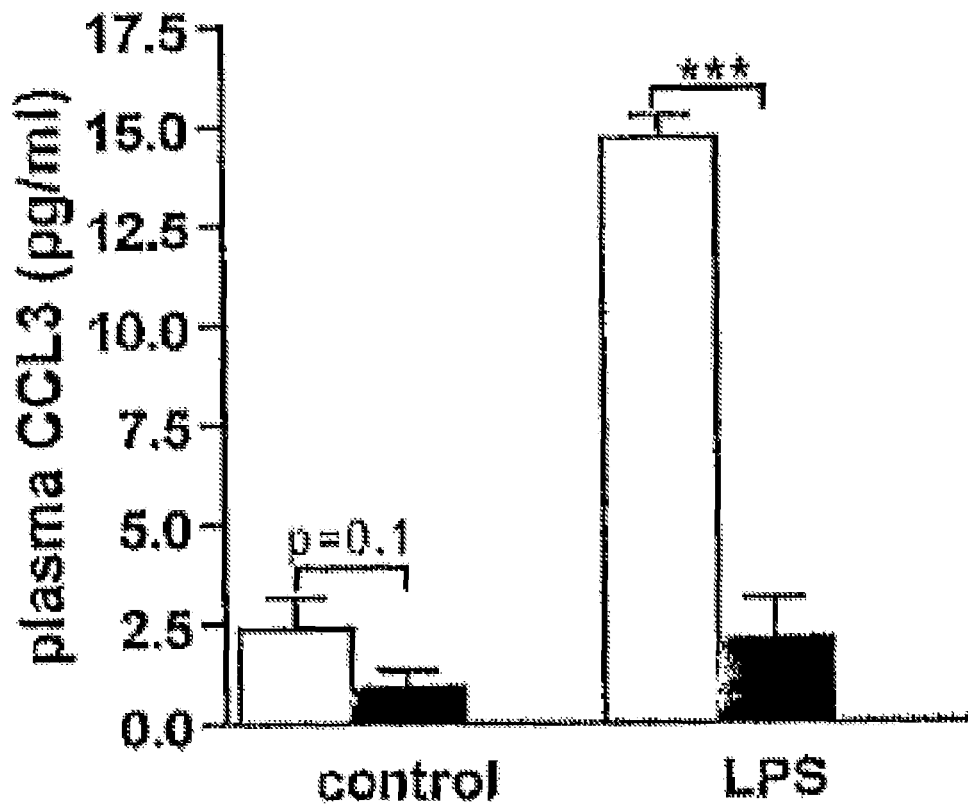

To assess effects of hematopoietic CCL3 deficiency on leukocyte migration and activation as well as on atherogenesis we reconstituted LDLr$^{-/-}$ mice with CCL3$^{-/-}$ bone marrow. CCL3 deficiency did not influence body weight or total cholesterol levels during the course of the experiment (data not shown). Plasma MIP1α levels were not significantly different between CCL3$^{-/-}$ chimeras and littermate controls (2.4±0.8 pg/ml in WT vs. 0.9±0.6 pg/ml in CCL3$^{-/-}$ chimeras; p=0.1, FIG. 17C). The CCL3 deficient phenotype was much more pronounced after in vivo treatment with LPS. Circulating MIP1α levels 24 h after LPS treatment were robustly increased in WT but not in CCL3$^{-/-}$ chimeras (14.7±0.4 pg/ml in control compared to 2.1±1.0 pg/ml in CCL3$^{-/-}$ chimeras; p=0.00005, FIG. 18A).

Figure 18F:
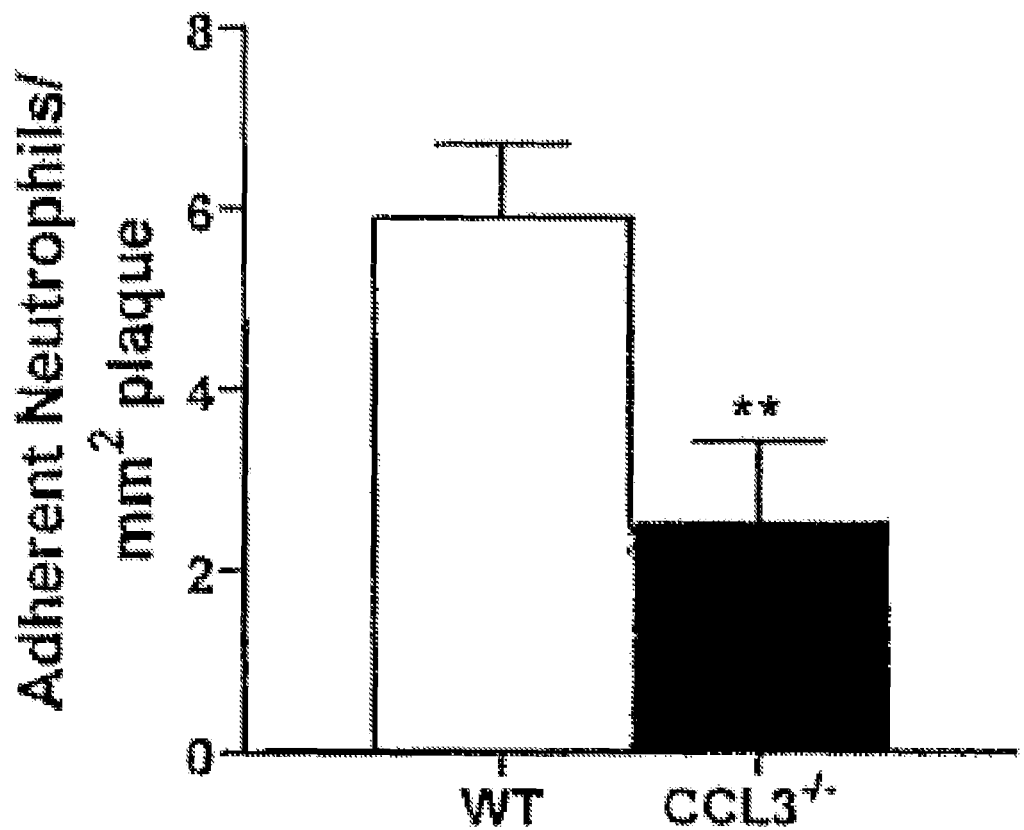

Lesion development in the aortic root of CCL3$^{-/-}$ chimeras was reduced by a significant 31% (135.1±76.5×103 μm2 in CCL3$^{-/-}$ compared to 198.4±51.4×103 μm2 in controls; P=0.04, FIG. 19A). The percentage of intimal MoMa-2$^+$ macrophages was not different between groups (19.3±2.6% in controls vs. 22.9±3.0% in CCL3$^{-/-}$, FIG. 18B), suggesting that CCL3 alone may not be very critical in macrophage accumulation and proliferation in the atherosclerotic plaque. CD3 T cell numbers were not influenced by CCL3 deficiency (2.9±1.2 T cells/mm$^2$ plaque in controls and 2.6±1.5 T cells/mm$^2$ plaque in CCL3$^{-/-}$, FIG. 18D). In contrast, the amount of plaque neutrophils (7.0±0.7 in WT compared to 2.9±0.8/mm$^2$ intimal tissue in CCL3$^{-/-}$ plaques; p=0.001, FIG. 18E), as well as neutrophil adherence were significantly reduced in CCL3$^{-/-}$ plaques (FIG. 18F). As measure of lesion progression stage intimal collagen deposition was determined. The percentage of collagen in CCL3$^{-/-}$ plaques was not influenced by CCL3 deficiency (7.5±1.4 in WT compared to 5.7±1.0% in CCL3$^{-/-}$ chimeras, FIG. 18C).

Figure 19C:
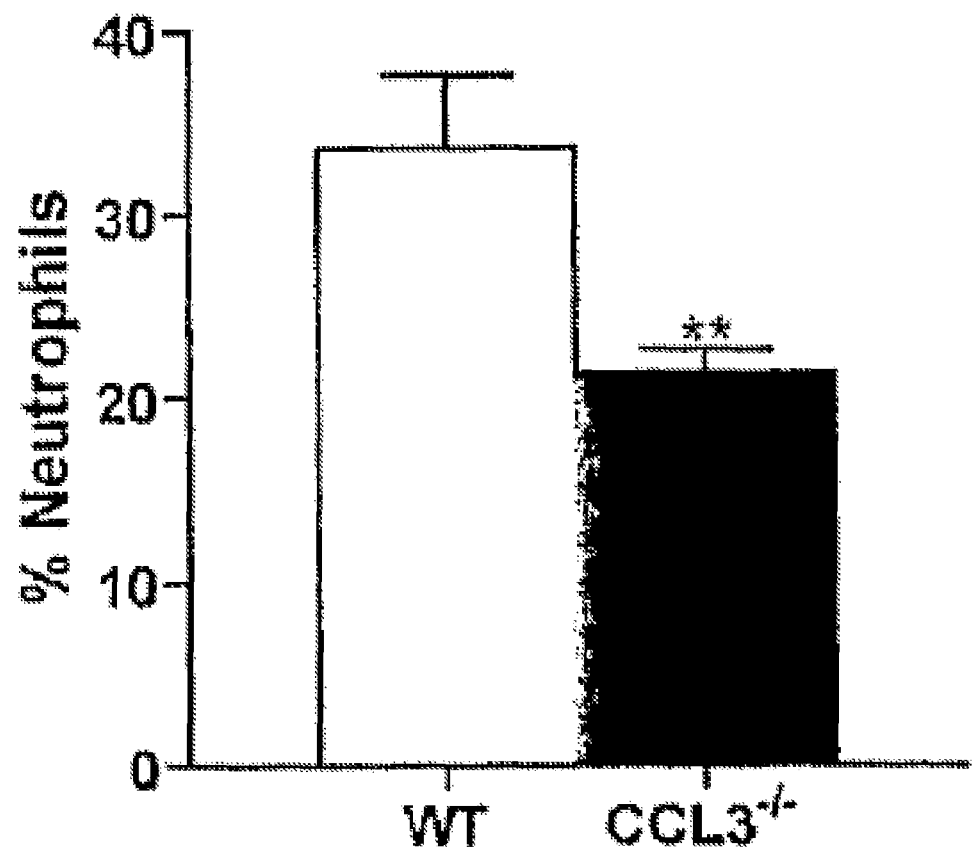

CCL3 deficiency did not influence the total number of circulating white blood cells in WT and CCL3$^{-/-}$ transplanted animals (4.4±0.7 in WT vs. 3.9±0.6×106 cells/ml in CCL3$^{-/-}$, FIG. 19A) and the number of circulating monocytes was not affected by CCL3 deficiency as well (7.7±1.1 in WT vs. 8.9±1.0% in CCL3$^{-/-}$ chimeras, FIG. 19B). Interestingly the percentage of circulating neutrophils was significantly decreased in CCL3$^{-/-}$ chimeras (35.3±3.9 in WT vs. 23.6±2.5% in CCL3$^{-/-}$ chimeras; p=0.02, FIG. 19C).

The decreased neutrophil numbers may result from a reduced half life or an impaired differentiation and stromal egress of neutrophils. To investigate this, animals were treated with a single injection of cyclophosphamide and the neutrophil elimination/repopulation kinetics was monitored for 10 days. Basal white blood cell number and cellular composition was not different between WT controls and CCL3$^{-/-}$ mice. CCL3 deficient cells were slightly more sensitive to cyclophosphamide treatment (FIG. 20A, B) as white blood cell half life was significantly enhanced in CCL3$^{-/-}$ mice compared to WT (1.09±0.07 days in WT compared to 0.89±0.06 days in CCL3$^{-/-}$; p=0.04, FIG. 20C) and appeared equally distributed over the neutrophil and lymphocyte subset (FIG. 20C). Thus CCL3 deficient mice show a decreased neutrophil half life which concurs with the reduced numbers of circulating and plaque neutrophils in this strain. Repopulation of cells initiated 5 days post injection and was similar between CCL3$^{-/-}$ and WT controls (FIG. 20D)

Next the chemotactic response of WT and CCL3$^{-/-}$ neutrophils was assessed towards a gradient of the major chemokine in neutrophil recruitment, KC. Two hours after i.p. injection of KC, WBCs and peritoneal leukocytes were isolated and analyzed for neutrophil content. Circulating neutrophil numbers were similar between WT and CCL3$^{-/-}$ animals (6.1±1.0 in WT compared to 5.3±1.0 in CCL3$^{-/-}$, FIG. 21A). Surprisingly, given the reduced circulating neutrophil numbers, CCL3$^{-/-}$ animals had slightly enhanced neutrophil numbers in the peritoneum under normal conditions (0.6±0.5% in WT compared to 1.4±0.07, p=0.2, data not shown). KC injections robustly induced neutrophil migration towards the peritoneum of control animals. Peritoneal neutrophil counts after KC injections in CCL3$^{-/-}$ animals were only marginally lower compared to WT animals (12.3±0.4 in controls compared to 10.2±1.9 in CCL3$^{-/-}$ animals, data not shown). However the induction of neutrophil influx was decreased in CCL3$^{-/-}$ animals (20× induction in WT compared to 7.5× induction in CCL3$^{-/-}$, p=0.003; FIG. 21C), suggestive of impaired chemotaxis of CCL3$^{-/-}$ neutrophils under conditions of inflammation.

Interestingly plaque formation was attenuated as a result of leukocyte specific absence of CCL3, which may be due to a decreased accumulation of neutrophils in the plaque. Collectively the data indicate that deficiency of CCL3 will translate in a reduced neutrophil half life and to a impaired CXCR2 dependent accumulation of neutrophils in the plaque, which subsequently will translate into attenuated plaque progression.

Discussion

Chemokine mediated migration of leukocytes into the vessel wall is an essential step in atherosclerotic lesion formation and progression. The CC chemokine CCL3 can interact with chemokine receptors CCR4, CCR1 and CCR5, of which the latter two have been implicated in atherogenesis. Combined with the upregulated aortic expression during atherogenesis 6, and its potent chemotactic effect on T cells, macrophages and neutrophils TNF-α, a role of this chemokine in atherogenesis is conceivable. Here we show that leukocytes are the prime source of CCL3 under conditions of inflammation and that leukocyte CCL3 deficiency attenuates plaque development by altering neutrophil half life and reducing neutrophil accumulation.

In vitro experiments clearly established that activated macrophages are a rich source of CCL3, which is in concurrence with earlier data. Moreover baseline levels of CCL3 in the circulation were seen to be only partly of leukocyte origin but almost exclusively produced by leukocytes during LPS elicited inflammatory responses. Expression profiles of atherosclerotic lesion development revealed that CCL3 is mainly upregulated during early lesion progression, suggesting that CCL3 is involved in plaque inflammation 6. Atherogenesis in CCL3$^{-/-}$ mice was significantly attenuated, but no effects on macrophage or T cell content were apparent. Interestingly, hematopoietic and systemic deficiency of one of the CCL3 receptors, CCR1, led to accelerated atherosclerosis. CCR1 deficient plaques contained more macrophages and T cells and CCR1$^{-/-}$ T cells produced more IFNγ. Conversely functional deficiency of CCR5, either in the hematopoietic lineage or systemically, was shown to reduce atherosclerotic lesion development and plaques contained less macrophages and T cells. Antagonism of CCR5 by use of Met-RANTES similarly attenuated atherosclerosis development, macrophage and T cell content. Furthermore Met-Rantes treatment resulted in lower expression levels of CCR5, but not of its ligand CCL313. CCL3 was shown to have a higher binding affinity for CCR5, suggestive that CCR5 mediated effects are primary during a chronic low rate inflammation, while acute substantial inflammation might correct these effects via CCR1 signalling. The phenotypic change seen in hematopoietic CCL3 deficiency seems to be more consistent with that of impaired CCR5 function, albeit that we did not see any noticeable effects on plaque macrophage content. This indicates that, although CCL3 might influence inflammatory cell migration, it is not crucial in monocyte or T cell migration towards the plaque.

Neutrophils were, until recently, not implicated in the pathogenesis of atherosclerosis. However more and more data are accumulating that support an active role of this subset of white blood cells in this disease. For instance, it was shown that plaque neutrophil infiltrates to be associated with acute coronary events. Experimental support showed the abundant presence of neutrophils in advanced mouse plaques, and from a collaborative expansion after blockage of CXCR4. Plaque neutrophils are potent inflammatory cells acting in a narrow time span. Neutrophils are associated with increased intimal apoptosis and a pro-inflammatory phenotype. Conceivably neutrophil accumulation in atherosclerotic lesions can induce plaque destabilization as a result of enhanced inflammation, necrotic core formation as a consequence of oxidative injury and matrix degradation by release of neutrophil elastases. CCL3 has been reported to be able to augment neutrophil chemotaxis induced by the pro-inflammatory cytokine TNFα in a CCR5 dependent manner. In concurrence with these findings attenuated neutrophil migration to and diapedesis into the plaque in hematopoietic CCL3 deficiency is shown in this example. Moreover in vivo neutrophil migration towards KC (murine IL8 analogue) was reduced in CCL3$^{-/-}$ mice. This indicates that IL-8, similar to TNFα, can induce CCL3 mediated neutrophil migration.

Another intriguing option is that CCL3 affects neutrophil homeostasis. During inflammation, circulating neutrophil numbers were significantly lower in CCL3$^{-/-}$ mice, which fits well with the notion that apoptosis of neutrophils is regarded as a protective measure to dampen acute inflammatory responses and prevent unwanted tissue damage. Terminally matured neutrophils therefore show a sharply reduced half life. Moreover, they have impaired migration and degranulation. A clear effect of CCL3$^{-/-}$ on neutrophil elimination kinetics was observed, as the half life of CCL3 deficient neutrophils was decreased. However repopulation of neutrophils was not influenced by CCL3 deficiency, showing that neutrophil maturation and stromal release per se are not influenced. These data suggest that CCL3$^{-/-}$ neutrophils are more sensitive to cyclophosphamide, and perhaps other pro-apoptotic signals leading to a reduced half life.

Taken together data in this example clearly establish a causal role for neutrophils in the development of atherosclerosis. Furthermore it is hypothesized that under conditions of inflammation leukocyte derived CCL3 can, possibly in concert with TNFα, alter neutrophil homeostasis and enhance neutrophil chemotaxis towards the atherosclerotic plaque to accelerate lesion formation.

What is claimed is:

1. A device for the detection of one or more analytes in a sample obtained from a subject, the device comprising:
   a) a surface to conduct at least one detection reaction, the surface comprising:
      a detection region comprising one or more epitope binding agents, wherein each epitope binding agent is configured to bind exclusively to one of the at least one analytes; and
      a reference region, wherein the detection region is separate from the reference region;
   b) one or more detection sensors to sense light associated with the detection region;
   c) one or more reference sensors to sense light associated with the reference region; and
   wherein the one or more detection sensors and the one or more reference sensors are operated using a balanced sensor method.

2. The device of claim 1, further comprising at least one light source to illuminate the detection region and the reference region, wherein the at least one light source is ambient light.

3. The device of claim 1, wherein the device utilizes ambient light only.

4. The device of claim 1, wherein the detection region comprises at least five epitope binding agents.

5. The device of claim 1, wherein the detection region comprises at least nine epitope binding agents.

6. The device of claim 1, wherein the detection region comprises at least thirteen epitope binding agents.

7. The device of claim 1, wherein the detection region comprises epitope binding agents specific for one or more of chemokine (C-C motif) ligand 3 (CCL3), chemokine (C-C motif) ligand 5 (CCL5), chemokine (C-C motif) ligand 18 (CCL8), high-sensitivity C-reactive protein (hsCRP), and cardiac Troponin I (TnI).

8. The device of claim 1, wherein the detection region comprises epitope binding agents specific one or more of CCL3, CCL5, CCL18, Heart-type fatty acid-binding protein (HFABP), Pregnancy-associated plasma protein A (PaPPa), hsCRP, cardiac Troponin I (hs cTnI), Placental growth factor (PIGF), brain natriuretic peptide (Nt-proBNP), Interferon gamma-induced protein 10 (IP-10), macrophage inhibitory cytokine 1 (MIC-1), cystatin C, lipoprotein-associated phospholipase A2 (LP PLA2).

9. A system for detecting one or more analytes in a sample and diagnosing a condition, the system comprising:
   a) a device comprising:
      a surface to conduct at least one detection reaction, the surface comprising a detection region and a reference region, wherein the detection region is separate from the reference region;
      one or more detection sensors to sense light associated with the detection region;
      one or more reference sensors to sense light associated with the reference region; and
      at least one light source to illuminate the detection region and the reference region;
   b) a computing device comprising one or more processors;
   c) a memory comprising:
      a calibration database comprising one or more calibration sets, each calibration set comprising a conversion between a combined sensor readout and a concentration of an analyte;
      a diagnostic database comprising one or more threshold values and one or more diagnostic rules;
      a CRM encoded with an analyte detection application comprising a plurality of modules executable by the one or more processors, the modules comprising:
         a control module to control the operation of the device and to coordinate the function of the plurality of modules;
         a balanced detection module to control the operation of the one or more sensors and/or light sources of the device;
         an analyte detection module to process combined output signals received from the balanced detection module;
         a post-processing module to further analyze the analyte concentrations calculated by the analyte detection module;
         a diagnostic module to compare the entries of the diagnostic array and to determine a condition of a patient according to one or more diagnostic rules defined within the diagnostic database stored in memory; and
         a GUI module to generate one or more forms to receive input to the system and/or display output from the system; and
   d) a display.

* * * * *